US009550984B2

(12) United States Patent
Puranen et al.

(10) Patent No.: US 9,550,984 B2
(45) Date of Patent: Jan. 24, 2017

(54) FUNGAL ENDOGLUCANASES, THEIR PRODUCTION AND USE

(71) Applicant: AB Enzymes Oy, Rajamäki (FI)

(72) Inventors: Terhi Puranen, Nurmijärvi (FI); Leena Valtakari, Rajamäki (FI); Marika Alapuranen, Rajamäki (FI); George Szakacs, Budapest (HU); Pentti Ojapalo, Tuusula (FI); Jari Vehmaanperä, Klaukkala (FI)

(73) Assignee: AB Enzymes Oy (FI)

( * ) Notice: Subject to any disclaimer, the term of this patent is extended or adjusted under 35 U.S.C. 154(b) by 0 days.

(21) Appl. No.: 14/057,401

(22) Filed: Oct. 18, 2013

(65) Prior Publication Data

US 2014/0099678 A1  Apr. 10, 2014

Related U.S. Application Data

(62) Division of application No. 13/142,630, filed as application No. PCT/FI2009/051042 on Dec. 28, 2009, now Pat. No. 8,592,195.

(30) Foreign Application Priority Data

Dec. 30, 2008 (FI) .................................... 20086250

(51) Int. Cl.
  C12N 9/24       (2006.01)
  C12P 19/14      (2006.01)
  D06M 16/00      (2006.01)
  D21C 5/00       (2006.01)
  C12P 19/02      (2006.01)
  C12N 9/42       (2006.01)

(52) U.S. Cl.
  CPC ........... *C12N 9/2437* (2013.01); *A23K 20/189* (2016.05); *C12P 19/02* (2013.01); *C12P 19/14* (2013.01); *C12Y 302/01004* (2013.01); *D06M 16/00* (2013.01); *D21C 5/005* (2013.01); *Y02P 20/52* (2015.11)

(58) Field of Classification Search
  None
  See application file for complete search history.

(56) References Cited

U.S. PATENT DOCUMENTS

| 5,475,101 A | 12/1995 | Ward et al. |
| 5,770,418 A | 6/1998 | Yaver et al. |
| 5,843,745 A | 12/1998 | Berka et al. |
| 2002/0165114 A1* | 11/2002 | Fowler et al. ............... 510/392 |
| 2007/0026420 A1 | 2/2007 | Bower et al. |

FOREIGN PATENT DOCUMENTS

| WO | 95/02043 A1 | 1/1995 |
| WO | 9533386 A1 | 12/1995 |
| WO | 9708325 A3 | 4/1997 |
| WO | WO 01/47956 * | 7/2001 |
| WO | 02/12465 A2 | 2/2002 |
| WO | 2007118935 A8 | 7/2009 |

OTHER PUBLICATIONS

Altschul SF, W Gish, W Miller, EW Myers and DJ Lipman. 1990. Basic local alignment search tool. J. Mol. Biol. 215:403-410.
Bailey M and Nevalainen H. 1981. Induction, isolation and testing of stable Trichoderma reesei mutants with improved production of solubilizing cellulase. Enzyme Microb. Technol. 3:153-157.
Bendtsen JD, H Nielsen, G von Heijne and S Brunak. 2004. Improved prediction of signal peptides: SignalP 3.0. J. Mol. Biol. 340:783-795.
Gasteiger E, A Gattiker, C Hoogland, I Ivanyi, RD Appel and A Bairoch. 2003. ExPASy: the proteiomics server for in-depth protein knowledge and analysis. Nucleic Acids Res. 31:3784-3788.
Haakana H, Miettinen-Oinonen A, Joutsjoki V, Mäntylä A, Suominen P and Vehmaanperä J. 2004. Cloning of cellulase genes from Melanocarpus albomyces and their efficient expression in Trichoderma reesei. Enzyme Microb. Technol. 34:159-167.
Henrissat B. (1991) A classification of glycosyl hydrolases based on amino acid sequence similarities. Biochem. J. 280: 309-316.
Henrissat B. and Bairoch A. (1993) New families in the classification of glycosyl hydrolases based on amino acid sequence similarities. Biochem. J. 293: 781-788.
Henrissat B. and Bairoch A. (1996).Updating the sequence-based classification of glycosyl hydrolases. Biochem. J. 316: 695-696.
Joutsjoki, VV, TK Torkkeli and KMH Nevalainen. 1993. Transformation of Trichoderma reesei with the Hormoconis resinae glucoamylase P (gamP) gene: production of a heterologous glucoamylase by Trichoderma reesei. Curr. Genet. 24:223-228.
Karhunen T, A Mäntylä, KMH Nevalainen and PL Suominen. 1993. High frequency one-step gene replacement in Trichoderma reesei. I. Endoglucanase I overproduction. Mol. Gen. Genet. 241:515-522.
Malardier L, Daboussi MJ , Julien J, Roussel F, Scazzocchio C and Brygoo Y. 1989. Cloning of the nitrate reductase gene (niaD) of Aspergillus nidulans and its use for transformation of Fusarium oxysporum. Gene 15:147-156.
Needleman S. and Wunsch C. (1970) A general method applicable to the search for similarities in the amino acid sequence of two proteins. Journal of Molecular Biology 48, 443-453.
Nielsen H, J Engelbrecht, S Brunak and G von Heijne. 1997. Identification of prokaryotic and eykaryotic signal peptides and prediction of thier cleavage sites. Protein Engineering 10:1-6.

(Continued)

*Primary Examiner* — Suzanne M Noakes
(74) *Attorney, Agent, or Firm* — Banner & Witcoff, Ltd.

(57) ABSTRACT

Novel fungal endoglucanases Cel5 and Cel12 are disclosed. The endoglucanases are conveniently produced by recombinant technology, and means for their production are described. The endoglucanases are used for treating cellulosic material, especially in textile industry, e.g. in biofinishing or biostoning. They may also be used in detergents, in animal feed and/or in pulp and paper industry, or in hydrolysis of lignocellulosic material for, e.g. bioethanol production.

13 Claims, 7 Drawing Sheets

(56) References Cited

OTHER PUBLICATIONS

Nierstrasz V.A. and Warmoeskerken M.M.C.G. (2003) Process engineering and industrial enzyme applications. In: Textile processing with enzymes. A.Cavaco-Paulo and G.M.Gübitz (eds.) Woodhead Publishing Ltd, Cambridge. pp. 120-157.

Paloheimo M, A Mäntylä, J Kallio, and P Suominen. 2003. High-yield production of a bacterial xylanase in the filamentous fungus Trichoderma reesei requires a carrier polypeptide with an intact domain structure. Appl. Env. Microbiol. 69:7073-7082.

Penttilä M, H Nevalainen, M Rättö, E Salminen and J Knowles. 1987. A versatile transformation system for the cellulolytic filamentous fungus Trichoderma reesei. Gene 61:155-164.

Raeder U and P Broda. 1985. Rapid preparation of DNA from filamentous fungi. Lett. Appl. Microbiol. 1:17-20.

Sambrook J, EF Fritsch and T Maniatis. 1989. Molecular cloning, a laboratory manual. Cold Spring Harbor Laboratory, New York, US.

Sambrook J and DW Russell. 2001. Molecular cloning, a laboratory manual. Cold Spring Harbor Laboratory, New York, US.

Rice P, Longden I and Bleasby A. (2000). EMBOSS: The European Molecular Biology Open Software Suite. Trends in Genetics 16:276-277.

Ward M, Wu S, Dauberman GW, Larenas E, Bower B, Rey M, Clarkson K and Bott R. 1992 Proceedings of the 2nd TRICEL symposium on Trichoderma reesei cellulases and other hybdrolases, Espoo, Finland, 1993 ed. Suominen P and Reinikainen T. Foundation for Biotechonological and industrual fermentation Research 8 (1993): 153-158.

Office Action issued for corresponding Indian Patent Application No. 2742/KOLNP/2011, dated Aug. 30, 2016.

Irwin, Nina, et al., "Molecular Cloning: A laboratory Manual," Cold Spring Harbor Laboratory Press, Cold Spring Harbor 2001.

Sandgren, Mats, et al. "Comparison of family 12 glycoside hydrolases and recruited substitutions important for thermal stability," Protein Science (2003), 12:848-860.

Xiao, Zhizhuang, et al., "Cold adaptation of a mesophilic cellulase, EG III from Trichoderma reesei, by directed evolution," Sci China C Life Sci. Aug. 2002;45(4):337-43.

\* cited by examiner

A)

B)

C)

D)

E)

F)

SEQUENCE LISTING

```
<160> NUMBER OF SEQ ID NOS: 82

<210> SEQ ID NO 1
<211> LENGTH: 18
<212> TYPE: DNA
<213> ORGANISM: artificial
<220> FEATURE:
<223> OTHER INFORMATION: primer
```

<400> SEQUENCE: 1
gagctctggg gtccgatt                                                 18

<210> SEQ ID NO 2
<211> LENGTH: 18
<212> TYPE: DNA
<213> ORGANISM: Artificial
<220> FEATURE:
<223> OTHER INFORMATION: primer

<400> SEQUENCE: 2
cgatgcagta tgcgccca                                                 18

<210> SEQ ID NO 3
<211> LENGTH: 18
<212> TYPE: DNA
<213> ORGANISM: Artificial
<220> FEATURE:
<223> OTHER INFORMATION: primer

<400> SEQUENCE: 3
atgaagttcc ttcaagtc                                                 18

<210> SEQ ID NO 4
<211> LENGTH: 17
<212> TYPE: DNA
<213> ORGANISM: Artificial
<220> FEATURE:
<223> OTHER INFORMATION: primer

<400> SEQUENCE: 4
ttagttgata gatgcgg                                                  17

<210> SEQ ID NO 5
<211> LENGTH: 9
<212> TYPE: PRT
<213> ORGANISM: Penicillium griseofulvum
<220> FEATURE:
<221> NAME/KEY: UNSURE
<222> LOCATION: (6)..(6)
<223> OTHER INFORMATION: glutamine or lysine
<220> FEATURE:
<221> NAME/KEY: UNSURE
<222> LOCATION: (8)..(8)
<223> OTHER INFORMATION: leucine or isoleucine
<220> FEATURE:
<221> NAME/KEY: UNSURE
<222> LOCATION: (9)..(9)
<223> OTHER INFORMATION: glutamine or lysine

<400> SEQUENCE: 5

Val Val Ala Ala Thr Xaa Trp Xaa Xaa
1               5

<210> SEQ ID NO 6
<211> LENGTH: 13
<212> TYPE: PRT
<213> ORGANISM: Penicillium griseofulvum
<220> FEATURE:
<221> NAME/KEY: UNSURE
<222> LOCATION: (1)..(1)
<223> OTHER INFORMATION: leucine or isoleucine
<220> FEATURE:
<221> NAME/KEY: UNSURE
<222> LOCATION: (2)..(2)
<223> OTHER INFORMATION: leucine or isoleucine
<220> FEATURE:
<221> NAME/KEY: UNSURE

```
<222> LOCATION: (13)..(13)
<223> OTHER INFORMATION: glutamine or lysine

<400> SEQUENCE: 6

Xaa Xaa Thr Ser Thr Thr Asp Phe Ala Ala Phe Trp Xaa
1               5                   10

<210> SEQ ID NO 7
<211> LENGTH: 13
<212> TYPE: PRT
<213> ORGANISM: Penicillium griseofulvum
<220> FEATURE:
<221> NAME/KEY: UNSURE
<222> LOCATION: (7)..(7)
<223> OTHER INFORMATION: leucine or isoleucine

<400> SEQUENCE: 7

Ser Gly Ala Tyr Ala Val Xaa Pro His Asn Phe Gly Arg
1               5                   10

<210> SEQ ID NO 8
<211> LENGTH: 7
<212> TYPE: PRT
<213> ORGANISM: Penicillium griseofulvum

<400> SEQUENCE: 8

Val Pro Phe Ala Met Glu Arg
1               5

<210> SEQ ID NO 9
<211> LENGTH: 13
<212> TYPE: PRT
<213> ORGANISM: Penicillium griseofulvum
<220> FEATURE:
<221> NAME/KEY: UNSURE
<222> LOCATION: (1)..(1)
<223> OTHER INFORMATION: leucine or isoleucine

<400> SEQUENCE: 9

Xaa Gly Glu Phe Ala Gly Pro Phe Glu Gly Glu Asn Lys
1               5                   10

<210> SEQ ID NO 10
<211> LENGTH: 20
<212> TYPE: DNA
<213> ORGANISM: artificial
<220> FEATURE:
<223> OTHER INFORMATION: primer

<400> SEQUENCE: 10
ccygtygght ggcartayyt                                           20

<210> SEQ ID NO 11
<211> LENGTH: 20
<212> TYPE: DNA
<213> ORGANISM: Artificial
<220> FEATURE:
<223> OTHER INFORMATION: primer

<400> SEQUENCE: 11
gghcctacwa aygcycartt                                           20

<210> SEQ ID NO 12
<211> LENGTH: 17
<212> TYPE: DNA
<213> ORGANISM: Artificial
<220> FEATURE:
```

<223> OTHER INFORMATION: primer

<400> SEQUENCE: 12
gayathcaya aytaygc                                              17

<210> SEQ ID NO 13
<211> LENGTH: 20
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (15)..(15)
<223> OTHER INFORMATION: n is a, c, g, or t

<400> SEQUENCE: 13
gtrccrgagt trtcngartc                                           20

<210> SEQ ID NO 14
<211> LENGTH: 17
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (6)..(6)
<223> OTHER INFORMATION: n is a, c, g, or t

<400> SEQUENCE: 14
swrtcnarrt ayttrtg                                              17

<210> SEQ ID NO 15
<211> LENGTH: 20
<212> TYPE: DNA
<213> ORGANISM: Artificial
<220> FEATURE:
<223> OTHER INFORMATION: primer

<400> SEQUENCE: 15
ggagactwyg arctyatgat                                           20

<210> SEQ ID NO 16
<211> LENGTH: 20
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 16
ggngaytwyg arytnatgat                                           20

<210> SEQ ID NO 17
<211> LENGTH: 20
<212> TYPE: DNA
<213> ORGANISM: Artificial
<220> FEATURE:
<223> OTHER INFORMATION: primer

<400> SEQUENCE: 17

-continued

```
gsctcrgtdc craaytggta                                              20

<210> SEQ ID NO 18
<211> LENGTH: 18
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t

<400> SEQUENCE: 18
ytcngtnccr aaytgrta                                                18

<210> SEQ ID NO 19
<211> LENGTH: 17
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (9)..(9)
<223> OTHER INFORMATION: n is a, c, g, or t

<400> SEQUENCE: 19
ttygayacna ayaayga                                                 17

<210> SEQ ID NO 20
<211> LENGTH: 17
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (15)..(15)
<223> OTHER INFORMATION: n is a, c, g, or t

<400> SEQUENCE: 20
atgcaycart ayctnga                                                 17

<210> SEQ ID NO 21
<211> LENGTH: 17
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (3)..(3)
<223> OTHER INFORMATION: n is a, c, g, or t

<400> SEQUENCE: 21
tcnagrtayt grtgcat                                                 17

<210> SEQ ID NO 22
<211> LENGTH: 24
<212> TYPE: DNA
<213> ORGANISM: Artificial
<220> FEATURE:
<223> OTHER INFORMATION: primer
```

<400> SEQUENCE: 22
ccaccasggs ccsgcsgccc acca                                           24

<210> SEQ ID NO 23
<211> LENGTH: 20
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 23
gtnccnttyg cnatggarcg                                                20

<210> SEQ ID NO 24
<211> LENGTH: 17
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (6)..(6)
<223> OTHER INFORMATION: n is a, c, g, or t

<400> SEQUENCE: 24
gayccncaya ayttygg                                                   17

<210> SEQ ID NO 25
<211> LENGTH: 17
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (12)..(12)
<223> OTHER INFORMATION: n is a, c, g, or t

<400> SEQUENCE: 25
ccraarttrt gnggrtc                                                   17

<210> SEQ ID NO 26
<211> LENGTH: 20
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 26
gayttygcng cnttytggaa                                                20

<210> SEQ ID NO 27
<211> LENGTH: 20
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 27
ttccaraang cngcraartc                                              20

<210> SEQ ID NO 28
<211> LENGTH: 20
<212> TYPE: DNA
<213> ORGANISM: Artificial
<220> FEATURE:
<223> OTHER INFORMATION: primer

<400> SEQUENCE: 28
tcraasggsc csgcraaytc                                              20

<210> SEQ ID NO 29
<211> LENGTH: 499
<212> TYPE: DNA
<213> ORGANISM: Trichoderma sp.

<400> SEQUENCE: 29
cccgtcggat ggcaatacct tgtgaacaac aacttgggtg gaactctaga tgcaaacaac     60
cttgccaaat acgaccagct cgttcagtct tgcctctctc taggtgtgta ctgcattatc    120
gatatacata actatgcacg ttggaatggt ggtattattg gccaaggtgg tcctacaaat    180
gctcagttca caagtctttg gtcacaatta gcaacaaaat acgcctctca gccaaaggtt    240
tggttcggaa tcatgaacga gccacacgat gtaaacatca atacctgggc cactactgtt    300
caagctgtcg ttactgcaat ccgtaatgct ggtgctactt cgcaatttat ttcgttacct    360
ggaaatgatt ggcaatccgc tggagctttt atttctgatg aagtgcagc agctttatct     420 cagatcaaga accctgatgg gtctacaacc aatctgattt cgacctaca caaatacctg     480 gactccgaca actcggcac                                                499

<210> SEQ ID NO 30
<211> LENGTH: 454
<212> TYPE: DNA
<213> ORGANISM: Trichoderma sp.

<400> SEQUENCE: 30
aaacgacggc cagtgaattg taatacgact cactataggg cgaattgaat ttagcggccg     60
cgaattcgcc cttgacatcc acaactacgc tcgctggaat ggcaaaatca ttggccaggg    120
aggtcctaca aacgctcaat ttactagtct ctggtcacaa atagcgacca agtatgcccc    180
agaaccgagg atatggtttg gcactatgaa tgaaccgcac gatcttaaca tcaccacctg    240
ggccggcact gtacaggctg ctgttactgc gatccgtaat gcaggtgcta cctcacagta    300
catctcacta ccgggcagtg actatcagtc tgccggacag atcatttctg atggtggtgc    360

```
agcggcttta agtgctatca ccaatccaga cggctcaaag actaacctca ttttcgatgt    420
gcacaagtac ttggactccg acaactccgg caca                                454

<210> SEQ ID NO 31
<211> LENGTH: 410
<212> TYPE: DNA
<213> ORGANISM: Trichoderma sp.

<400> SEQUENCE: 31
aattcgccct tggagacttt gagcttatga tctggcaagt cgtatagact gtctttgcca     60
atattttgac taatcagtaa ttccactttt aggctcgcaa agtatggaga tatcggcccc    120
attggatcct ctcaggggac agttaatgtc aatggtcaga gctggacgct ctactacggc    180
ttcaatggag ccatgcaagt ctatagcttt gttgccccca ccaataccac caattggagt    240
ggagatatca agaacttctt caactatcta cgagataaca aaggataccc ggcctcaagt    300
caatatctcc tcagtatgtg actctagttt tcgttttgtt acgaatatgc tttgcggtga    360
tactaatcag atgcttctta ggttaccaat ttggaaccga gccaagggcg              410

<210> SEQ ID NO 32
<211> LENGTH: 386
<212> TYPE: DNA
<213> ORGANISM: Trichoderma fertile

<400> SEQUENCE: 32
cattatcgat atacataatt atgctcgctg gaatggtggg attattggtc agggaggccc     60
aacaaatgct cagttcacta gtctttggtc gcaattggca tcgaagtacg catctcaacc    120
gaaggtgtgg ttcggaatca tgaatgagcc acacgatgtg aatattaaca cttgggctac    180
cactgtgcaa gccgttgtca ctgcaatccg aagcgcggga gctacctcgc agttcatttc    240
gctgcctgga aatgattggc agtctgctgg agctttcatc tctgatggca gtgcagccgc    300
tttatctcaa gtcaagaacc ccgatggctc aacaaccaat ctgattttcg acctgcataa    360
gtacctggac tccgacaatc cggcac                                        386

<210> SEQ ID NO 33
<211> LENGTH: 474
<212> TYPE: DNA
<213> ORGANISM: Trichoderma fertile

<400> SEQUENCE: 33
tttcccagtc acgacgttgt aaaacgacgg ccagtgaatt gtaatacgac tcactatagg     60
gcgaattgaa tttagcggcc gcgaattcgc ccttgacata cacaactacg ctcgctggaa    120
cggccaaatc attggccagg gcggtcctac aaacgcccaa ttcgttagtc tctggacaca    180
attggcgacc aagtatgcct cacagcccaa gatatggttt ggcattatga atgaaccaca    240
cgaccttaac gtcaccactt gggccgttac tgtgcaggct gttgttactg caatccgtaa    300
tgcgggtgct acctcgcagt atatctcact gccgggcagt gactatcagt ctgccggatc    360
tgtcatttcc gatggtagtg cagcggcttt aggtgctatc accaatccca acggctcaaa    420
gaccaacctc attttcgatg tgcataagta cttggactcc gacaactccg gcac          474

<210> SEQ ID NO 34
<211> LENGTH: 513
<212> TYPE: DNA
<213> ORGANISM: Trichoderma fertile

<400> SEQUENCE: 34
```

```
tggagacttt gagcttatga tctggtaaga tgaatggaga gctgattgtg atttcagctg    60
ctaatatgat taaacaggct tggcaagtat ggtgacattt accccattgg ttcatcccag   120
ggcaacgtca acgtcaatgg ccaagattgg cagctatact acggatggaa cggccagatg   180
caagtctaca gctttgttgc ttacacacct gtccagaatt ggaacggaga tatcaaacaa   240
ttctacagct ggttggcttc aaacagggga taccctattg cagccagta  ccttctgagt   300 aagtcgatta cttgccttgg tgaaagaaac ggaatattaa tcaacctta  ataggctacc   360 agttcggtac tgaggcaagg gcgaattcgc ggccgctaaa ttcaattcgc cctatagtga   420
gtcgtattac aattcactgg ccgtcgtttt acaacgtcgt gactgggaaa accctggcgt   480
tacccaactt aatcgccttg cagcacatcc ccc                                513

<210> SEQ ID NO 35
<211> LENGTH: 248
<212> TYPE: DNA
<213> ORGANISM: Penicillium spinulosum

<400> SEQUENCE: 35
atgcaccaat acctcgactc ggatggatcg ggtaccagct ccacctgtgt ctcgagcacg    60
attggtcagg agcgcgtgga agctgcgacg caatggctga tcgataacaa caaggttggt   120
gtgttgggtg aatttgccgg tggtatcaac actgtgtgtg aggaggcgat tgtgggaatg   180
ttggattata tggaggagaa ttcggcagtt tggaagggtg ctttgtggtg ggcggcgggc   240
cctggtgg                                                            248

<210> SEQ ID NO 36
<211> LENGTH: 248
<212> TYPE: DNA
<213> ORGANISM: Penicillium spinulosum

<400> SEQUENCE: 36
atgcaccagt acctcgactc ggatggatct ggcacttccg acacatgcgt cagcacgacc    60
atcggccagg agcgtgtaca gtcagcaaca gaatggttgc aaagcaatgg gaaactaggt   120
tttctgggcg agtttgctgg tggtgctaat acagtctgtc agagcgctgt gactggaatg   180
ctgagctact tgcaagagaa cagtgacgtc tggctcggag catcctggtg ggcggccggc   240
ccctggtg                                                            248

<210> SEQ ID NO 37
<211> LENGTH: 249
<212> TYPE: DNA
<213> ORGANISM: Fusarium cf. equiseti

<400> SEQUENCE: 37
tgcaccaata cttcgactcc gactcatccg gtacttcacc taactgtgtt tccacaacca    60
ttggtgttga gcgtctgcag gctgctacca agtggctccg tgacaacaag aaggtcggca   120
tgattggaga gtttgctggc ggtcctaacg agacttgcaa gaccgctgtt aagaacatgc   180
ttgactttat gaagaagaac actgatgtct ggaagggctt tacttggtgg gcggcggggc   240
ccgtggtgg                                                           249

<210> SEQ ID NO 38
<211> LENGTH: 250
<212> TYPE: DNA
<213> ORGANISM: Geomyces pannorum
```

```
<400> SEQUENCE: 38
atgcaccagt acctcgactc tgacggatct gggacgtcgg caaactgcgt ctcgtccact      60
attggcgtcg agcgcgtgac gagcgcgacg gcatggctgc gcgcaaatgg caagattggg     120
atcattggcg agtttgcggg aggtgccaac agccagtgca aggctgctgt tacggggctg     180
ctgcagcact tgaaggcgaa ttctgatgtg tggactggag ccttgtggtg ggccgccggc     240
cccctggtgg                                                            250

<210> SEQ ID NO 39
<211> LENGTH: 296
<212> TYPE: DNA
<213> ORGANISM: Penicillium griseofulvum

<400> SEQUENCE: 39
gtgccgttcg cgatggagcg attggttccc gggactctga ctgcgagtcc ggatgccacc      60
tacctagctg cattgaaaag tgtatgtgct atagccttt t gcacataaaa cattgatacc    120 aatacccca a cagactgtca actctatcac gtctagcggt gcatatgctg tgattgatcc    180
tcacaacttt ggaagatagt aagttccatt gccttacagg gaggattaat ctgaccatat    240
atatatagtt atggcaaaat catcacctcg actactgact tcgccgcctt ctggaa        296

<210> SEQ ID NO 40
<211> LENGTH: 140
<212> TYPE: DNA
<213> ORGANISM: Geomyces pannorum

<400> SEQUENCE: 40
gtgccgtttg cgatggagcg cctgatcccc gacacgctga ctggaacgcc tgacgcaacc      60
tacctcgctg accttaaaga gattgtcagc tacatcactg gcaagggagc atacgcggtt    120 atcgacccc c acaacttcgg                                                140

<210> SEQ ID NO 41
<211> LENGTH: 1257
<212> TYPE: DNA
<213> ORGANISM: Trichoderma gamsii

<400> SEQUENCE: 41
atgaataaac caatgggccc gttgctactc gctgccacgc ttatggcaag cggtgctgtc      60
gcacagacac aaagcgtttg gggacaatgt ggaggtacgg gctacagtgg cccaacgaac    120
tgtgcttctg gttctgcatg ctctacattg aatccctatt acgccagtg cattccaggc    180 gcaaccagct tcattacctc gactacctcg accaagtctc ctggttctgg gtcaagcaca    240
acctcttcag cttctcaacc aacaggctct gggcagacgc gatttgctgg tatcaacatt    300
gccgggttcg actttggctg cacaattgat ggaacctgtg ttacttcaca gatttacccg    360
ccactgaaga actttggtgg tactaataac cacccagatg gtgtcggcca gatgcagcac    420
tttgtcaacg atgataaatt aaacatcttc cgtctacctg ttggatggca gtatcttgtt    480
aacaacaacc tgggtggaac attggactcc accgctatta gcaactatga tcagcttgtt    540
caaggctgtt tagccactgg atcgtactgt atcgtcgata ccacaactac cgcccgttgg    600
aatggcgcaa tcattggcca aggtggccct acaaacgctc aatttgtcag cctttggacg    660
caattagcaa ctaaatatgc gtctcagtca aaagtctggt ttggcattgt gaacgagccg    720
catgatgtgg atattaacac ttgggggtcaa actgtgcaag ccgttgttac tgccatccgt    780
aacgccggtg ccacaacgca attcatttca ctgccaggaa ccgacttcca gtccgctgga    840
```

```
agcttcctct ccgatggcag ctctactgcc ctgtcccagg tgaagaatcc tgatggttcg      900
acgacaaact tgatctttga tttccataaa taccttgact ctgataactc tggtactcat      960
acagagtgtg tcaccaacaa catcgctacc gcgttccagc ctgtcgccac ctggcttcgc     1020
cagaacaagc gccaaggtat tttgacggaa actggtggcg gcaacactca gtcatgcctt     1080
acggacatgt gccaacagaa ccaatttctc aaccaaaact ccgacgtctt cctcggctac     1140
attggctggg gtgctggctc atttgacagc acttacgaat tgaccttgac accgacccaa     1200
aacggaaaca cttggactga cactgctctg gcagcagctt gctttctcg caaatag         1257
```

<210> SEQ ID NO 42
<211> LENGTH: 418
<212> TYPE: PRT
<213> ORGANISM: Trichoderma gamsii

<400> SEQUENCE: 42

```
Met Asn Lys Pro Met Gly Pro Leu Leu Ala Ala Thr Leu Met Ala
1               5                   10                  15

Ser Gly Ala Val Ala Gln Thr Gln Ser Val Trp Gly Gln Cys Gly Gly
            20                  25                  30

Thr Gly Tyr Ser Gly Pro Thr Asn Cys Ala Ser Gly Ser Ala Cys Ser
        35                  40                  45

Thr Leu Asn Pro Tyr Tyr Ala Gln Cys Ile Pro Gly Ala Thr Ser Phe
    50                  55                  60

Ile Thr Ser Thr Thr Ser Thr Lys Ser Pro Gly Ser Gly Ser Ser Thr
65                  70                  75                  80

Thr Ser Ser Ala Ser Gln Pro Thr Gly Ser Gly Gln Thr Arg Phe Ala
                85                  90                  95

Gly Ile Asn Ile Ala Gly Phe Asp Phe Gly Cys Thr Ile Asp Gly Thr
            100                 105                 110

Cys Val Thr Ser Gln Ile Tyr Pro Pro Leu Lys Asn Phe Gly Gly Thr
        115                 120                 125

Asn Asn His Pro Asp Gly Val Gly Gln Met Gln His Phe Val Asn Asp
    130                 135                 140

Asp Lys Leu Asn Ile Phe Arg Leu Pro Val Gly Trp Gln Tyr Leu Val
145                 150                 155                 160

Asn Asn Asn Leu Gly Gly Thr Leu Asp Ser Thr Ala Ile Ser Asn Tyr
                165                 170                 175

Asp Gln Leu Val Gln Gly Cys Leu Ala Thr Gly Ser Tyr Cys Ile Val
            180                 185                 190

Asp Ile His Asn Tyr Ala Arg Trp Asn Gly Ala Ile Ile Gly Gln Gly
        195                 200                 205

Gly Pro Thr Asn Ala Gln Phe Val Ser Leu Trp Thr Gln Leu Ala Thr
    210                 215                 220

Lys Tyr Ala Ser Gln Ser Lys Val Trp Phe Gly Ile Val Asn Glu Pro
225                 230                 235                 240

His Asp Val Asp Ile Asn Thr Trp Gly Gln Thr Val Gln Ala Val Val
                245                 250                 255

Thr Ala Ile Arg Asn Ala Gly Ala Thr Thr Gln Phe Ile Ser Leu Pro
            260                 265                 270

Gly Thr Asp Phe Gln Ser Ala Gly Ser Phe Leu Ser Asp Gly Ser Ser
        275                 280                 285

Thr Ala Leu Ser Gln Val Lys Asn Pro Asp Gly Ser Thr Thr Asn Leu
    290                 295                 300
```

Ile Phe Asp Phe His Lys Tyr Leu Asp Ser Asp Asn Ser Gly Thr His
305                 310                 315                 320

Thr Glu Cys Val Thr Asn Asn Ile Ala Thr Ala Phe Gln Pro Val Ala
            325                 330                 335

Thr Trp Leu Arg Gln Asn Lys Arg Gln Gly Ile Leu Thr Glu Thr Gly
        340                 345                 350

Gly Gly Asn Thr Gln Ser Cys Leu Thr Asp Met Cys Gln Gln Asn Gln
    355                 360                 365

Phe Leu Asn Gln Asn Ser Asp Val Phe Leu Gly Tyr Ile Gly Trp Gly
370                 375                 380

Ala Gly Ser Phe Asp Ser Thr Tyr Glu Leu Thr Leu Thr Pro Thr Gln
385                 390                 395                 400

Asn Gly Asn Thr Trp Thr Asp Thr Ala Leu Ala Ala Ala Cys Phe Ser
                405                 410                 415

Arg Lys

<210> SEQ ID NO 43
<211> LENGTH: 1269
<212> TYPE: DNA
<213> ORGANISM: Trichoderma gamsii

<400> SEQUENCE: 43
atgatcaaca acaaggctgc gctgctgttt gcagcctatg ctggagtgag tggtgttgcg        60
gcacagcaac agaccacctg gggacaatgt ggaggacaag gctattcagg cccgacaaat       120
tgtgtttctg gagcagcttg ctcaacaata aactcttact atgctcaatg tgtccctgct       180
accggcataa tcaccagcac caccaccaga gctacatcag ctacatcaac gctaaaatca       240
accacagcat cggcatcaac cacgcctccg ccatccaatg gctcaggtac tcagtttgcc       300
ggtatcaaca ttgcaggatt cgactttagt tgctccactg acggaacttg caatgtgagc       360
ggtgcctacc cgccgctgaa gaactacgat ggcgcaaaca actatccaga tggcgttggg       420
cagatgcagc atttcgtcaa agacgacgga ttcaacatct tccgtcttcc tgttggttgg       480
caatatttag tcaatggtac tcttggtgct actcttaacc ctacaaactt gggctattac       540
gatcaacttg ttcaaggatg cttggccacg ggtgcatact gcatcattga cattcacaac       600
tatgcccgct ggaacactgg aattattggc caaggcggtc ctacaaatgc ccagtttgtt       660 aaccttttgga cccaactagc taccaaatac gcttccgagt cgaagatttg gttcggtgtc       720
atgaatgagc acacgatgt taacatcacc acctgggccg ccaccgtgca acttgttgtt       780
actgcgattc gcaatgcggg cgctacctca cagtatattt cactccctgg tactgactgg       840
caatctgctg gaagcatcat ttctgatggt ggtgcggcgg ctctgggtgc catcaccaac       900
cctgatggct caaagaccaa cctcattttc gatgtgcaca gtacttgga ttccgataac       960 tctggcacta actcgatttg tgttacggac aatgtcgctt ccgcatttgc gccactggct      1020
acctggcttc gttcgaataa ccgcaaggcc atcttgactg agaccggtgg tgcaatact       1080 ccatcctgtg aacagtatct ttgccagcag atccagtacc tcaaccagaa tgccgatgtt      1140
tacctgggat acgttggctg ggctgcgggt tcgtttgatc ccggctaccc attggcagag      1200
acaccggtcc agaatgcaga cggcagctgg actgattcgg ctttggtggc actttgcctt      1260
gctcgatga                                                               1269

<210> SEQ ID NO 44
<211> LENGTH: 422

<212> TYPE: PRT
<213> ORGANISM: Trichoderma gamsii

<400> SEQUENCE: 44

```
Met Ile Asn Asn Lys Ala Ala Leu Leu Phe Ala Ala Tyr Ala Gly Val
1               5                   10                  15

Ser Gly Val Ala Ala Gln Gln Thr Thr Trp Gly Gln Cys Gly Gly
            20                  25                  30

Gln Gly Tyr Ser Gly Pro Thr Asn Cys Val Ser Gly Ala Ala Cys Ser
                35                  40                  45

Thr Ile Asn Ser Tyr Tyr Ala Gln Cys Val Pro Ala Thr Gly Ile Ile
            50                  55                  60

Thr Ser Thr Thr Thr Arg Ala Thr Ser Ala Thr Ser Thr Leu Lys Ser
65                  70                  75                  80

Thr Thr Ala Ser Ala Ser Thr Thr Pro Pro Ser Asn Gly Ser Gly
                85                  90                  95

Thr Gln Phe Ala Gly Ile Asn Ile Ala Gly Phe Asp Phe Ser Cys Ser
            100                 105                 110

Thr Asp Gly Thr Cys Asn Val Ser Gly Ala Tyr Pro Pro Leu Lys Asn
            115                 120                 125

Tyr Asp Gly Ala Asn Asn Tyr Pro Asp Gly Val Gly Gln Met Gln His
            130                 135                 140

Phe Val Lys Asp Asp Gly Phe Asn Ile Phe Arg Leu Pro Val Gly Trp
145                 150                 155                 160

Gln Tyr Leu Val Asn Gly Thr Leu Gly Ala Thr Leu Asn Pro Thr Asn
                165                 170                 175

Leu Gly Tyr Tyr Asp Gln Leu Val Gln Gly Cys Leu Ala Thr Gly Ala
            180                 185                 190

Tyr Cys Ile Ile Asp Ile His Asn Tyr Ala Arg Trp Asn Thr Gly Ile
            195                 200                 205

Ile Gly Gln Gly Gly Pro Thr Asn Ala Gln Phe Val Asn Leu Trp Thr
            210                 215                 220

Gln Leu Ala Thr Lys Tyr Ala Ser Glu Ser Lys Ile Trp Phe Gly Val
225                 230                 235                 240

Met Asn Glu Pro His Asp Val Asn Ile Thr Thr Trp Ala Ala Thr Val
                245                 250                 255

Gln Leu Val Val Thr Ala Ile Arg Asn Ala Gly Ala Thr Ser Gln Tyr
            260                 265                 270

Ile Ser Leu Pro Gly Thr Asp Trp Gln Ser Ala Gly Ser Ile Ile Ser
            275                 280                 285

Asp Gly Gly Ala Ala Ala Leu Gly Ala Ile Thr Asn Pro Asp Gly Ser
            290                 295                 300

Lys Thr Asn Leu Ile Phe Asp Val His Lys Tyr Leu Asp Ser Asp Asn
305                 310                 315                 320

Ser Gly Thr Asn Ser Ile Cys Val Thr Asp Asn Val Ala Ser Ala Phe
                325                 330                 335

Ala Pro Leu Ala Thr Trp Leu Arg Ser Asn Asn Arg Lys Ala Ile Leu
            340                 345                 350

Thr Glu Thr Gly Gly Gly Asn Thr Pro Ser Cys Glu Gln Tyr Leu Cys
            355                 360                 365

Gln Gln Ile Gln Tyr Leu Asn Gln Asn Ala Asp Val Tyr Leu Gly Tyr
            370                 375                 380

Val Gly Trp Ala Ala Gly Ser Phe Asp Pro Gly Tyr Pro Leu Ala Glu
385                 390                 395                 400
```

Thr Pro Val Gln Asn Ala Asp Gly Ser Trp Thr Asp Ser Ala Leu Val
            405                 410                 415

Ala Leu Cys Leu Ala Arg
            420

<210> SEQ ID NO 45
<211> LENGTH: 1257
<212> TYPE: DNA
<213> ORGANISM: Hypocrea rufa

<400> SEQUENCE: 45

```
atgaataagc ccatgggccc attgctgctc gctgccacgc ttatggcaag cggtgctatt      60
gcacagacac aaactgtttg gggccaatgt ggaggtacgg gctacagtgg tccaacgaac     120
tgtgcttctg gttctgcatg ctctacactt aacccgtatt acgcccagtg cattccaggt     180
gcaaccagct tcgttaccct gactacctcg accaagtctt ctggttctgg gtcaaccaca     240
acatcttcag cttcccaacc aaccggctct gggcaaacgc gattcgctgg tatcaacatt     300
gctggattcg actttggctg cacaactgat ggaacctgtg ttacttcaca gatttacccg     360
ccactgaaaa actttggtgg tacgaataac caccccgatg tgtcggcca gatgcagcac     420
tttgtcaaag atgataaatt aaacatcttc cgtctacctg ttggatggca atatcttgtt     480
aacaacaacc tgggtggaac attggactcc actgctatca gcaactatga ccagcttgtt     540
caaggctgtt tagccactgg agcatactgt attgtcgata tccacaacta tgcccgttgg     600
aacggcgcaa tcattggcca aggaggacct acaaatgctc aatttgttag tctttggacg     660
caattagcaa ctaaatatgc gtctcagtca aaagtctggt ttggcattgt gaatgagccg     720
catgatgtgg atattaacac ctggggtaca accgtacagg ctgttgttac cgccatccgt     780
aacgctggtg ccacgacgca gttcatttcc ctgccaggaa ctgactacca gtccgctgga     840
aacttcctta ccgatggcag ttctactgcc ttgtctctgg tgaagaatcc tgatggttcg     900
acaacaaatt tgatctttga tttccacaaa taccttgact ctgataactc tggtacccat     960
acagagtgtg tcaccaacaa catcgctacc gcattccagc tgtcgccac tggcttcgt    1020
cagaacaaac gccaaggtat tttgactgaa actggcggtg caacactca gtcttgcatt    1080
caggacgtat gccaacagaa ccagtttctc aaccaaaact ccgacgtctt tctcggctac    1140
cttggctggg ctgctggctc atttgatagc acttatgact tgaccttgac accgacccaa    1200
aacggaaaca cttggactga cactgctctg gcagcagctt gctttttctcg cgcatag     1257
```

<210> SEQ ID NO 46
<211> LENGTH: 418
<212> TYPE: PRT
<213> ORGANISM: Hypocrea rufa

<400> SEQUENCE: 46

Met Asn Lys Pro Met Gly Pro Leu Leu Leu Ala Ala Thr Leu Met Ala
1               5                   10                  15

Ser Gly Ala Ile Ala Gln Thr Gln Thr Val Trp Gly Gln Cys Gly Gly
            20                  25                  30

Thr Gly Tyr Ser Gly Pro Thr Asn Cys Ala Ser Gly Ser Ala Cys Ser
        35                  40                  45

Thr Leu Asn Pro Tyr Tyr Ala Gln Cys Ile Pro Gly Ala Thr Ser Phe
    50                  55                  60

Val Thr Ser Thr Thr Ser Thr Lys Ser Ser Gly Ser Gly Ser Thr Thr
65                  70                  75                  80

Thr Ser Ser Ala Ser Gln Pro Thr Gly Ser Gly Gln Thr Arg Phe Ala
            85                  90                  95

Gly Ile Asn Ile Ala Gly Phe Asp Phe Gly Cys Thr Thr Asp Gly Thr
        100                 105                 110

Cys Val Thr Ser Gln Ile Tyr Pro Pro Leu Lys Asn Phe Gly Gly Thr
    115                 120                 125

Asn Asn His Pro Asp Gly Val Gly Gln Met Gln His Phe Val Lys Asp
130                 135                 140

Asp Lys Leu Asn Ile Phe Arg Leu Pro Val Gly Trp Gln Tyr Leu Val
145                 150                 155                 160

Asn Asn Asn Leu Gly Gly Thr Leu Asp Ser Thr Ala Ile Ser Asn Tyr
                165                 170                 175

Asp Gln Leu Val Gln Gly Cys Leu Ala Thr Gly Ala Tyr Cys Ile Val
            180                 185                 190

Asp Ile His Asn Tyr Ala Arg Trp Asn Gly Ala Ile Ile Gly Gln Gly
        195                 200                 205

Gly Pro Thr Asn Ala Gln Phe Val Ser Leu Trp Thr Gln Leu Ala Thr
    210                 215                 220

Lys Tyr Ala Ser Gln Ser Lys Val Trp Phe Gly Ile Val Asn Glu Pro
225                 230                 235                 240

His Asp Val Asp Ile Asn Thr Trp Gly Thr Thr Val Gln Ala Val Val
                245                 250                 255

Thr Ala Ile Arg Asn Ala Gly Ala Thr Thr Gln Phe Ile Ser Leu Pro
            260                 265                 270

Gly Thr Asp Tyr Gln Ser Ala Gly Asn Phe Leu Thr Asp Gly Ser Ser
        275                 280                 285

Thr Ala Leu Ser Leu Val Lys Asn Pro Asp Gly Ser Thr Thr Asn Leu
    290                 295                 300

Ile Phe Asp Phe His Lys Tyr Leu Asp Ser Asp Asn Ser Gly Thr His
305                 310                 315                 320

Thr Glu Cys Val Thr Asn Asn Ile Ala Thr Ala Phe Gln Pro Val Ala
                325                 330                 335

Thr Trp Leu Arg Gln Asn Lys Arg Gln Gly Ile Leu Thr Glu Thr Gly
            340                 345                 350

Gly Gly Asn Thr Gln Ser Cys Ile Gln Asp Val Cys Gln Gln Asn Gln
        355                 360                 365

Phe Leu Asn Gln Asn Ser Asp Val Phe Leu Gly Tyr Leu Gly Trp Ala
    370                 375                 380

Ala Gly Ser Phe Asp Ser Thr Tyr Asp Leu Thr Leu Thr Pro Thr Gln
385                 390                 395                 400

Asn Gly Asn Thr Trp Thr Asp Thr Ala Leu Ala Ala Ala Cys Phe Ser
                405                 410                 415

Arg Ala

<210> SEQ ID NO 47
<211> LENGTH: 1269
<212> TYPE: DNA
<213> ORGANISM: Hypocrea atroviridis

<400> SEQUENCE: 47
atgatgaaca acaaggcggc gctgctgttt gcagcctatg ctggagtgag tggtgttgcg      60
gcacagcagc agaccaccctg gggacaatgt ggaggacaag gctattcagg cccgacaagt    120
tgtgtttctg gagcggccctg ctcaacaatt aatccttact atgcccagtg tataccctgct  180

```
accggcataa tcaccagcac caccaccaga gctacatcag ctacatcaac actaaaatca      240
accacagcct cggcatcaag tacgcctccg ccgtccaatg gctcaggcac ccagtttgcc      300
ggtatcaaca ttgcaggatt cgactttagt tgctccactg acggaacttg caatgtgtcc      360
ggtgcctacc caccgctgaa gaactacgac ggcgcaaaca actatccaga tggcgttggg      420
cagatgcagc atttcgtcaa agacgacgga ttcaacatct tccgtcttcc cgtcggctgg      480
cagtatttag tcaatgctac tcttggtgcc actctcaacc ctaccaatct gggttactat      540
gatcaacttg tccagggatg cctggacacg ggtgcatact gcatcattga cattcacaac      600
tatgcccgtt ggaacactgg aatcattggc caaggcggtc ctacaaacgc ccaattcgtt      660
aacctttgga cccaaatagc caccaaatac gcttcagagc cgaagatttg gtttggtgtc      720
atgaatgagc cgcacgatgt caacatcacc acctgggccg ccaccgtgca gcttgttgtt      780
accgcaatcc gcaatgcggg cgctacctca cagtacatct cacttcctgg tactgactgg      840
cagtctgctg gaagcatcat cactgatggc ggtgtcgcgg ctctgggtgc catcaccaac      900
cctgatggct caaagaccaa cctcattttc gatgtgcaca agtacttgga ttccgacaac      960
tctggcacca actcggtgtg tgttacggac aatgtcgatt ctgcatttgc gccactggct     1020
acctggctcc gttcgaataa ccgcaaggcc attttgactg agaccggtgg cggcaatact     1080
ccatcgtgtg aacagtatct ttgccagcag atccagtacc tcaaccagaa tgccgatgtc     1140
tacatgggat acgttggctg ggctgcgggt tcgtttgatc ccggctaccc attggcagag     1200
acgccggtcc agaatgccga tggcagctgg actgatcagc ctttggtatc gctttgcctt     1260
gctcgatga                                                            1269

<210> SEQ ID NO 48
<211> LENGTH: 422
<212> TYPE: PRT
<213> ORGANISM: Hypocrea atroviridis

<400> SEQUENCE: 48

Met Met Asn Asn Lys Ala Ala Leu Leu Phe Ala Ala Tyr Ala Gly Val
1               5                   10                  15

Ser Gly Val Ala Ala Gln Gln Gln Thr Thr Trp Gly Gln Cys Gly Gly
                20                  25                  30

Gln Gly Tyr Ser Gly Pro Thr Ser Cys Val Ser Gly Ala Ala Cys Ser
            35                  40                  45

Thr Ile Asn Pro Tyr Tyr Ala Gln Cys Ile Pro Ala Thr Gly Ile Ile
        50                  55                  60

Thr Ser Thr Thr Thr Arg Ala Thr Ser Ala Thr Ser Thr Leu Lys Ser
65                  70                  75                  80

Thr Thr Ala Ser Ala Ser Ser Thr Pro Pro Ser Asn Gly Ser Gly
                85                  90                  95

Thr Gln Phe Ala Gly Ile Asn Ile Ala Gly Phe Asp Phe Ser Cys Ser
            100                 105                 110

Thr Asp Gly Thr Cys Asn Val Ser Gly Ala Tyr Pro Pro Leu Lys Asn
        115                 120                 125

Tyr Asp Gly Ala Asn Asn Tyr Pro Asp Gly Val Gly Gln Met Gln His
    130                 135                 140

Phe Val Lys Asp Asp Gly Phe Asn Ile Phe Arg Leu Pro Val Gly Trp
145                 150                 155                 160

Gln Tyr Leu Val Asn Ala Thr Leu Gly Ala Thr Leu Asn Pro Thr Asn
                165                 170                 175
```

```
Leu Gly Tyr Tyr Asp Gln Leu Val Gln Gly Cys Leu Asp Thr Gly Ala
            180                 185                 190

Tyr Cys Ile Ile Asp Ile His Asn Tyr Ala Arg Trp Asn Thr Gly Ile
        195                 200                 205

Ile Gly Gln Gly Gly Pro Thr Asn Ala Gln Phe Val Asn Leu Trp Thr
    210                 215                 220

Gln Ile Ala Thr Lys Tyr Ala Ser Glu Pro Lys Ile Trp Phe Gly Val
225                 230                 235                 240

Met Asn Glu Pro His Asp Val Asn Ile Thr Thr Trp Ala Ala Thr Val
            245                 250                 255

Gln Leu Val Val Thr Ala Ile Arg Asn Ala Gly Ala Thr Ser Gln Tyr
            260                 265                 270

Ile Ser Leu Pro Gly Thr Asp Trp Gln Ser Ala Gly Ser Ile Ile Thr
        275                 280                 285

Asp Gly Gly Val Ala Ala Leu Gly Ala Ile Thr Asn Pro Asp Gly Ser
    290                 295                 300

Lys Thr Asn Leu Ile Phe Asp Val His Lys Tyr Leu Asp Ser Asp Asn
305                 310                 315                 320

Ser Gly Thr Asn Ser Val Cys Val Thr Asp Asn Val Asp Ser Ala Phe
            325                 330                 335

Ala Pro Leu Ala Thr Trp Leu Arg Ser Asn Asn Arg Lys Ala Ile Leu
            340                 345                 350

Thr Glu Thr Gly Gly Gly Asn Thr Pro Ser Cys Glu Gln Tyr Leu Cys
        355                 360                 365

Gln Gln Ile Gln Tyr Leu Asn Gln Asn Ala Asp Val Tyr Met Gly Tyr
    370                 375                 380

Val Gly Trp Ala Ala Gly Ser Phe Asp Pro Gly Tyr Pro Leu Ala Glu
385                 390                 395                 400

Thr Pro Val Gln Asn Ala Asp Gly Ser Trp Thr Asp Gln Pro Leu Val
            405                 410                 415

Ser Leu Cys Leu Ala Arg
            420

<210> SEQ ID NO 49
<211> LENGTH: 1278
<212> TYPE: DNA
<213> ORGANISM: Trichoderma harzianum

<400> SEQUENCE: 49
atgaaaaaca acaaggcttc acggctgctc gcagcctatc tatatctcgg agcaactggt      60
gtcgtagcac agcaacagac cacctggggg caatgcggag gaataggcta cagtggtcca     120
acgagctgta cttcggggac gagctgctca acattgaact catattacgc ccaatgtatc     180
cctgctactg gcattatcac aagcactcgg accactcttg catcaacatc agcaacaaca     240
actacatcag catcaagaac cacctcagca acttcaattc ccccgcctag ctcgggcgtc     300
cggtttgcag gtatcaacat tgctgggttc gacttcagtt gctcaaccga tggaacttgc     360
aatgtatctg gtgcctatcc gccactcaag aattatgatg cgcaaacaa ctatccagat     420 ggtgttggtc agatgcaaca ctttgtgaag acgatggtt tcaatatttt ccgcttgccc     480
gtcagctggc agtatctggt gaatgccaac cttggcggca ccttggacgc accaatctg     540 ggctattatg atcaactcgt ccagggatgt cttgcaacgg tgcatactg catcatcgac     600 atccacaact atgctcgctg gaatggcaag atcattggcc agggaggccc tacaaacgct     660
```

```
caatttgtta gcctttggac ccaaatagcg accaagtatg cctcggaacc caggatatgg      720
tttggtacta tgaatgagcc gcacgatgtt aacatcacca cctgggcggg taccgtacag      780
gctgttgtta ctgcaatccg taatgcgggt gctgcctcac aatacatctc acttccgggc      840
actgactatc aatccgctgg acaaatcata tctgatggtg gtgcagcggc tctatctatc      900
atcaagaacc cagacggctc aacaaccaac ctgatcttcg atgttcacaa gtacctggac      960
tcggataact ctggtaccaa ctcgatctgt gttacggaca atgtcgacag tgcattcgcg     1020
ccattggcta cctggcttcg tacgaacaag cgtcaagcta ttctgaccga gactggtggt     1080
ggcaatactc cgtcgtgcga acagtacatg tgccagcaga tccaataccT caaccagaac     1140
gccgatgttt atatgggata tgttggatgg gctgcgggct cgttcgatcc aggatacccg     1200
ctggctgaga ctccggttca ggcttcaagc ggtgcctgga ctgatcagcc tctggtgtcg     1260
atgtgccttg cccgttga                                                   1278
```

<210> SEQ ID NO 50
<211> LENGTH: 425
<212> TYPE: PRT
<213> ORGANISM: Trichoderma harzianum

<400> SEQUENCE: 50

```
Met Lys Asn Asn Lys Ala Ser Arg Leu Leu Ala Ala Tyr Leu Tyr Leu
1               5                   10                  15

Gly Ala Thr Gly Val Val Ala Gln Gln Thr Thr Trp Gly Gln Cys
            20                  25                  30

Gly Gly Ile Gly Tyr Ser Gly Pro Thr Ser Cys Thr Ser Gly Thr Ser
        35                  40                  45

Cys Ser Thr Leu Asn Ser Tyr Tyr Ala Gln Cys Ile Pro Ala Thr Gly
    50                  55                  60

Ile Ile Thr Ser Thr Arg Thr Thr Leu Ala Ser Thr Ser Ala Thr Thr
65                  70                  75                  80

Thr Thr Ser Ala Ser Arg Thr Thr Ser Ala Thr Ser Ile Pro Pro Pro
                85                  90                  95

Ser Ser Gly Val Arg Phe Ala Gly Ile Asn Ile Ala Gly Phe Asp Phe
            100                 105                 110

Ser Cys Ser Thr Asp Gly Thr Cys Asn Val Ser Gly Ala Tyr Pro Pro
        115                 120                 125

Leu Lys Asn Tyr Asp Gly Ala Asn Asn Tyr Pro Asp Gly Val Gly Gln
    130                 135                 140

Met Gln His Phe Val Lys Asp Asp Gly Phe Asn Ile Phe Arg Leu Pro
145                 150                 155                 160

Val Ser Trp Gln Tyr Leu Val Asn Ala Asn Leu Gly Gly Thr Leu Asp
                165                 170                 175

Ala Thr Asn Leu Gly Tyr Tyr Asp Gln Leu Val Gln Gly Cys Leu Ala
            180                 185                 190

Thr Gly Ala Tyr Cys Ile Ile Asp Ile His Asn Tyr Ala Arg Trp Asn
        195                 200                 205

Gly Lys Ile Ile Gly Gln Gly Gly Pro Thr Asn Ala Gln Phe Val Ser
    210                 215                 220

Leu Trp Thr Gln Ile Ala Thr Lys Tyr Ala Ser Glu Pro Arg Ile Trp
225                 230                 235                 240

Phe Gly Thr Met Asn Glu Pro His Asp Val Asn Ile Thr Thr Trp Ala
                245                 250                 255

Gly Thr Val Gln Ala Val Val Thr Ala Ile Arg Asn Ala Gly Ala Ala
```

```
              260                 265                 270
Ser Gln Tyr Ile Ser Leu Pro Gly Thr Asp Tyr Gln Ser Ala Gly Gln
            275                 280                 285

Ile Ile Ser Asp Gly Gly Ala Ala Leu Ser Ile Ile Lys Asn Pro
        290                 295                 300

Asp Gly Ser Thr Thr Asn Leu Ile Phe Asp Val His Lys Tyr Leu Asp
305                 310                 315                 320

Ser Asp Asn Ser Gly Thr Asn Ser Ile Cys Val Thr Asp Asn Val Asp
                325                 330                 335

Ser Ala Phe Ala Pro Leu Ala Thr Trp Leu Arg Thr Asn Lys Arg Gln
            340                 345                 350

Ala Ile Leu Thr Glu Thr Gly Gly Gly Asn Thr Pro Ser Cys Glu Gln
                355                 360                 365

Tyr Met Cys Gln Gln Ile Gln Tyr Leu Asn Gln Asn Ala Asp Val Tyr
        370                 375                 380

Met Gly Tyr Val Gly Trp Ala Ala Gly Ser Phe Asp Pro Gly Tyr Pro
385                 390                 395                 400

Leu Ala Glu Thr Pro Val Gln Ala Ser Ser Gly Ala Trp Thr Asp Gln
                405                 410                 415

Pro Leu Val Ser Met Cys Leu Ala Arg
            420                 425

<210> SEQ ID NO 51
<211> LENGTH: 1257
<212> TYPE: DNA
<213> ORGANISM: Hypocrea koningiopsis

<400> SEQUENCE: 51
atgaataagc ccatgggccc gttgctgctc gctgccacgc ttttggcaag cggtgctatt     60
gcacaaacac aaagtgtttg gggacaatgt ggaggtaatg ctacagtggg cccaacgaac    120
tgtgcttctg gttctgcatg ctctacacag aaccccatt acgcccagtg cgttccaggt    180
```
aacggaaaca cttggactga cacctctctg gcagcagctt gcttctctcg cgcatag      1257

<210> SEQ ID NO 52
<211> LENGTH: 418
<212> TYPE: PRT
<213> ORGANISM: Hypocrea koningiopsis

<400> SEQUENCE: 52

```
Met Asn Lys Pro Met Gly Pro Leu Leu Leu Ala Ala Thr Leu Leu Ala
1               5                   10                  15

Ser Gly Ala Ile Ala Gln Thr Gln Ser Val Trp Gly Gln Cys Gly Gly
            20                  25                  30

Asn Gly Tyr Ser Gly Pro Thr Asn Cys Ala Ser Gly Ser Ala Cys Ser
        35                  40                  45

Thr Gln Asn Pro Tyr Tyr Ala Gln Cys Val Pro Gly Ala Thr Ser Phe
    50                  55                  60

His Thr Ser Thr Thr Ser Thr Lys Ser Pro Gly Ser Gly Ser Ser Thr
65                  70                  75                  80

Thr Ser Ser Ala Ser Gln Pro Thr Gly Ser Gly Gln Thr Arg Phe Ala
                85                  90                  95

Gly Ile Asn Ile Ala Gly Phe Asp Phe Gly Cys Thr Thr Asp Gly Thr
            100                 105                 110

Cys Val Thr Ser Gln Val Tyr Pro Pro Leu Lys Asn Phe Asp Gly Ala
        115                 120                 125

Asn Asn Tyr Pro Asp Gly Val Gly Gln Met Gln His Phe Val Lys Asp
    130                 135                 140

Asp Lys Leu Asn Ile Phe Arg Leu Pro Val Gly Trp Gln Tyr Leu Val
145                 150                 155                 160

Asn Asn Asn Leu Gly Gly Thr Leu Asp Ser Thr Asn Leu Gly Tyr Tyr
                165                 170                 175

Asp Gln Leu Val Gln Gly Cys Leu Ala Thr Gly Ala Tyr Cys Ile Val
            180                 185                 190

Asp Val His Asn Tyr Ala Arg Trp Asn Gly Ala Ile Ile Gly Gln Gly
        195                 200                 205

Gly Pro Thr Asn Ala Gln Phe Thr Asn Leu Trp Thr Gln Ile Ala Thr
    210                 215                 220

Lys Tyr Ala Ser Gln Ser Lys Ile Trp Phe Gly Ile Met Asn Glu Pro
225                 230                 235                 240

His Asp Val Asn Ile Asn Thr Trp Gly Gln Thr Val Gln Ala Val Val
                245                 250                 255

Thr Ala Ile Arg Asn Ala Gly Ala Thr Thr Gln Phe Ile Ser Leu Pro
            260                 265                 270

Gly Thr Asp Tyr Gln Ser Ala Gly Ser Phe Leu Ser Asp Gly Ser Ser
        275                 280                 285

Thr Ala Leu Ser Gln Val Lys Asn Pro Asp Gly Ser Thr Thr Asn Leu
    290                 295                 300

Ile Phe Asp Val His Lys Tyr Leu Asp Ser Asp Asn Ser Gly Thr His
305                 310                 315                 320

Thr Glu Cys Val Thr Asn Asn Ile Ala Thr Ala Phe Gln Pro Leu Ala
                325                 330                 335

Thr Trp Leu Arg Gln Asn Asn Arg Gln Ala Ile Leu Thr Glu Thr Gly
            340                 345                 350

Gly Gly Asn Val Ala Ser Cys Ile Thr Asp Val Cys Gln Gln Asn Gln
        355                 360                 365
```

```
Phe Leu Asn Gln Asn Ser Asp Val Phe Leu Gly Tyr Val Gly Trp Gly
    370                 375                 380

Ala Gly Ser Phe Asp Asn Thr Tyr Ala Leu Thr Leu Thr Pro Thr Gln
385                 390                 395                 400

Asn Gly Asn Thr Trp Thr Asp Thr Ser Leu Ala Ala Cys Phe Ser
                405                 410                 415

Arg Ala

<210> SEQ ID NO 53
<211> LENGTH: 1260
<212> TYPE: DNA
<213> ORGANISM: Trichoderma sp.

<400> SEQUENCE: 53
atgagcaagc ctatgggttc attgctgctt gcagccgctc tgctcgccag cggctccatt      60
gcacagcaaa ctgtttgggg gcagtgtgga ggaataggat atagcggccc caccgactgc     120
gccgctggat cggcctgctc aactctcaac ccctattatg ctcaatgtat cccgggtgcc     180
accaccatgt caacctcaac caagccgacc tctgttccag catcaacgac tagggcaagt     240
tcaacatcgt cagctactcc accagctggt tctggcctaa ctcgatttgc tggagtcaac     300
attgccggat tcgattttgg ctgtggaact gatggaacct gcgtcacctc gaaagtatac     360
ccgccactga gaactatgc tggcacaaac aactaccctg acggtgttgg tcagatgcaa     420
cactttgtca cgatgataa attgacaatt ttccgtctac ctgttgggtg caatacctt     480 gtgaacaaca acttgggtgg aactctagat gcaaacaacc ttgccaaata cgaccagctc     540
gttcagtctt gcctctctct aggtgtgtac tgcattatcg atatacataa ctatgcacgt     600
tggaatggtg gtattattgg ccaaggtggt cctacaaatg ctcagttcac aagtctttgg     660
tcacaattag caacaaaata cgcctctcag ccaaaggttt ggttcggaat catgaatgag     720
ccacacgatg taaacatcaa tacctgggcc actactgttc aagctgtcgt tactgcaatc     780
cgtaatgctg gtgctacttc gcaatttatt tcgttacctg gaaatgattg gcaatccgct     840 ggagcttta tttctgatgg aagtgcagca gctttatctc agatcaagaa ccctgatggg     900
tctacaacca atctgatttt cgacctacac aaataccctg gactcggaca ctctggaact     960
cacgccgact gtgtcacaaa caatatcaat gatgccttct cacctgtcgc cacttggctc    1020
cgtcaaaaca tcgccaggc tatcctaact gagactggtg gtggtaacac tcagtcatgc    1080
attcaatata tctgccaaca gttccaatat ctaaaccaaa attccgacgt ctaccttggc    1140
tacgttggat ggggtgcggg ctcatttgat agcacttata tcctgacgga gacgccaact    1200
ggtagcggaa gctcttggac tgatacatca cttgtaagct catgcatcgc tcggaaataa    1260

<210> SEQ ID NO 54
<211> LENGTH: 419
<212> TYPE: PRT
<213> ORGANISM: Trichoderma sp.

<400> SEQUENCE: 54

Met Ser Lys Pro Met Gly Ser Leu Leu Leu Ala Ala Leu Leu Ala
1               5                   10                  15

Ser Gly Ser Ile Ala Gln Gln Thr Val Trp Gly Gln Cys Gly Gly Ile
                20                  25                  30

Gly Tyr Ser Gly Pro Thr Asp Cys Ala Ala Gly Ser Ala Cys Ser Thr
            35                  40                  45
```

```
Leu Asn Pro Tyr Tyr Ala Gln Cys Ile Pro Gly Ala Thr Thr Met Ser
 50                  55                  60
Thr Ser Thr Lys Pro Thr Ser Val Pro Ala Ser Thr Thr Arg Ala Ser
 65                  70                  75                  80
Ser Thr Ser Ser Ala Thr Pro Pro Ala Gly Ser Gly Leu Thr Arg Phe
                 85                  90                  95
Ala Gly Val Asn Ile Ala Gly Phe Asp Phe Gly Cys Gly Thr Asp Gly
                100                 105                 110
Thr Cys Val Thr Ser Lys Val Tyr Pro Pro Leu Lys Asn Tyr Ala Gly
                115                 120                 125
Thr Asn Asn Tyr Pro Asp Gly Val Gly Gln Met Gln His Phe Val Asn
130                 135                 140
Asp Asp Lys Leu Thr Ile Phe Arg Leu Pro Val Gly Trp Gln Tyr Leu
145                 150                 155                 160
Val Asn Asn Asn Leu Gly Gly Thr Leu Asp Ala Asn Asn Leu Ala Lys
                165                 170                 175
Tyr Asp Gln Leu Val Gln Ser Cys Leu Ser Leu Gly Val Tyr Cys Ile
                180                 185                 190
Ile Asp Ile His Asn Tyr Ala Arg Trp Asn Gly Gly Ile Ile Gly Gln
                195                 200                 205
Gly Gly Pro Thr Asn Ala Gln Phe Thr Ser Leu Trp Ser Gln Leu Ala
            210                 215                 220
Thr Lys Tyr Ala Ser Gln Pro Lys Val Trp Phe Gly Ile Met Asn Glu
225                 230                 235                 240
Pro His Asp Val Asn Ile Asn Thr Trp Ala Thr Thr Val Gln Ala Val
                245                 250                 255
Val Thr Ala Ile Arg Asn Ala Gly Ala Thr Ser Gln Phe Ile Ser Leu
                260                 265                 270
Pro Gly Asn Asp Trp Gln Ser Ala Gly Ala Phe Ile Ser Asp Gly Ser
            275                 280                 285
Ala Ala Ala Leu Ser Gln Ile Lys Asn Pro Asp Gly Ser Thr Thr Asn
            290                 295                 300
Leu Ile Phe Asp Leu His Lys Tyr Leu Asp Ser Asp Asn Ser Gly Thr
305                 310                 315                 320
His Ala Asp Cys Val Thr Asn Asn Ile Asn Asp Ala Phe Ser Pro Val
                325                 330                 335
Ala Thr Trp Leu Arg Gln Asn Asn Arg Gln Ala Ile Leu Thr Glu Thr
                340                 345                 350
Gly Gly Gly Asn Thr Gln Ser Cys Ile Gln Tyr Ile Cys Gln Gln Phe
            355                 360                 365
Gln Tyr Leu Asn Gln Asn Ser Asp Val Tyr Leu Gly Tyr Val Gly Trp
            370                 375                 380
Gly Ala Gly Ser Phe Asp Ser Thr Tyr Ile Leu Thr Glu Thr Pro Thr
385                 390                 395                 400
Gly Ser Gly Ser Ser Trp Thr Asp Thr Ser Leu Val Ser Ser Cys Ile
                405                 410                 415
Ala Arg Lys

<210> SEQ ID NO 55
<211> LENGTH: 1275
<212> TYPE: DNA
<213> ORGANISM: Trichoderma sp.

<400> SEQUENCE: 55
```

| | |
|---|---|
| atgaccaaca ataaggctac acggctgctt gcagcttctc tatgtcttgg agcgagtggt | 60 |
| gtcgtagcac aacaacagac ttcttgggga caatgcggag gaataggcta cggtggcccg | 120 |
| acgagttgta cttctgggac aagctgctca acgctgaatt cgtattatgc tcaatgtatc | 180 |
| cctgctaccg gcataatcac gagcacccgc accactcttg cgtcaacatc ggcatcaaca | 240 |
| acaagagcat cagcaacaac ttcggcaagc tctcttccac cacccacctc aggggttcgg | 300 |
| tttgctggta tcaatattgc tggattcgac tttagttgct cgactgacgg aacctgcaac | 360 |
| gtatctggcg cctatccgcc actgaagaac tatgacggcg caaataacta tccggatggc | 420 |
| gttgggcaaa tgcaacattt tgtgaacgac gaccatttca atattttccg cttgcctgtc | 480 |
| agttggcagt atctagtgaa tgccaacctt ggcggcaccc tggatgcaac caatctgggc | 540 |
| tattatgatc aactcgttca gggatgcctg ccacagggg catactgtat catcgacatc | 600 |
| cacaactatg ctcgctggaa tggcaaaatc attggccagg aggtcctac aaacgctcaa | 660 |
| tttactagtc tctggtcaca aatagcgacc aagtatgcct cagaaccgag gatatggttt | 720 |
| ggcactatga atgaaccgca cgatcttaac atcacccct gggccggcac tgtacaggct | 780 |
| gctgttactg cgatccgtaa tgcaggtgct acctcacagt acatctcact accgggcagt | 840 |
| gactatcagt ctgccggaca gatcatttct gatggtggtg cagcggcttt aagtgctatc | 900 |
| accaatccag acggctcaaa gactaacctc attttcgatg tgcacaagta cttggactca | 960 |
| gataattctg gtaccaactc aatctgtgtt acggacaacg tggatagcgc attcgcgccg | 1020 |
| ctagctacct ggctccgtac aaacaaacgc ctggctattc tgactgagag tggtggtggc | 1080 |
| aatactgcat cttgtgaaca gtacatgtgc cagcagatcc agtatctcaa ccagaactcc | 1140 |
| gatgtttata tgggatatgt tggatgggct gcaggctcat tcgatcccgg ttacccatta | 1200 |
| gcggagacac ctgttcaagg ttcaaacggt gcctggacag accagcccct ggtgcagctt | 1260 |
| tgccttgccc gttga | 1275 |

<210> SEQ ID NO 56
<211> LENGTH: 424
<212> TYPE: PRT
<213> ORGANISM: Trichoderma sp.

<400> SEQUENCE: 56

```
Met Thr Asn Asn Lys Ala Thr Arg Leu Leu Ala Ala Ser Leu Cys Leu
1               5                   10                  15

Gly Ala Ser Gly Val Val Ala Gln Gln Gln Thr Ser Trp Gly Gln Cys
            20                  25                  30

Gly Gly Ile Gly Tyr Gly Gly Pro Thr Ser Cys Thr Ser Gly Thr Ser
        35                  40                  45

Cys Ser Thr Leu Asn Ser Tyr Tyr Ala Gln Cys Ile Pro Ala Thr Gly
    50                  55                  60

Ile Ile Thr Ser Thr Arg Thr Thr Leu Ala Ser Thr Ala Ser Thr
65                  70                  75                  80

Thr Arg Ala Ser Ala Thr Thr Ser Ala Ser Leu Pro Pro Thr
                85                  90                  95

Ser Gly Val Arg Phe Ala Gly Ile Asn Ile Ala Gly Phe Asp Phe Ser
            100                 105                 110

Cys Ser Thr Asp Gly Thr Cys Asn Val Ser Gly Ala Tyr Pro Pro Leu
        115                 120                 125

Lys Asn Tyr Asp Gly Ala Asn Asn Tyr Pro Asp Gly Val Gly Gln Met
    130                 135                 140
```

```
Gln His Phe Val Asn Asp Asp His Phe Asn Ile Phe Arg Leu Pro Val
145                 150                 155                 160

Ser Trp Gln Tyr Leu Val Asn Ala Asn Leu Gly Gly Thr Leu Asp Ala
                165                 170                 175

Thr Asn Leu Gly Tyr Tyr Asp Gln Leu Val Gln Gly Cys Leu Ala Thr
            180                 185                 190

Gly Ala Tyr Cys Ile Ile Asp Ile His Asn Tyr Ala Arg Trp Asn Gly
        195                 200                 205

Lys Ile Ile Gly Gln Gly Gly Pro Thr Asn Ala Gln Phe Thr Ser Leu
    210                 215                 220

Trp Ser Gln Ile Ala Thr Lys Tyr Ala Ser Glu Pro Arg Ile Trp Phe
225                 230                 235                 240

Gly Thr Met Asn Glu Pro His Asp Leu Asn Ile Thr Thr Trp Ala Gly
                245                 250                 255

Thr Val Gln Ala Ala Val Thr Ala Ile Arg Asn Ala Gly Ala Thr Ser
            260                 265                 270

Gln Tyr Ile Ser Leu Pro Gly Ser Asp Tyr Gln Ser Ala Gly Gln Ile
        275                 280                 285

Ile Ser Asp Gly Gly Ala Ala Ala Leu Ser Ala Ile Thr Asn Pro Asp
    290                 295                 300

Gly Ser Lys Thr Asn Leu Ile Phe Asp Val His Lys Tyr Leu Asp Ser
305                 310                 315                 320

Asp Asn Ser Gly Thr Asn Ser Ile Cys Val Thr Asp Asn Val Asp Ser
                325                 330                 335

Ala Phe Ala Pro Leu Ala Thr Trp Leu Arg Thr Asn Lys Arg Leu Ala
            340                 345                 350

Ile Leu Thr Glu Ser Gly Gly Gly Asn Thr Ala Ser Cys Glu Gln Tyr
        355                 360                 365

Met Cys Gln Gln Ile Gln Tyr Leu Asn Gln Asn Ser Asp Val Tyr Met
    370                 375                 380

Gly Tyr Val Gly Trp Ala Ala Gly Ser Phe Asp Pro Gly Tyr Pro Leu
385                 390                 395                 400

Ala Glu Thr Pro Val Gln Gly Ser Asn Gly Ala Trp Thr Asp Gln Pro
                405                 410                 415

Leu Val Gln Leu Cys Leu Ala Arg
                420

<210> SEQ ID NO 57
<211> LENGTH: 1311
<212> TYPE: DNA
<213> ORGANISM: Trichoderma fertile

<400> SEQUENCE: 57
atggctccat tgctgcttgc agctgcattc atggtcagcg gcgccgtagc gcagcagacc      60
acttggggac agtgtggagg tataggttac agtggcccga ccaactgtgt ccctggaact     120
gcttgctcaa ccctcaaccc ctattatgcc caatgcatcc aggtgccac caccatgtcc      180 acctctacca gcccccaac ctctggtcca caacaacaa caacaacaac aacaacaaca      240
acaacaacaa caacaacaac aacaacaaca acaacaacca caggtcaac atcaacatcc      300 tcagctgctc cacctactgg ctctggtctg acgcaatttg gtggaattaa cattgccggc      360
ttcgattttg gttgtggcac agatggaacc tgcgtcacat cgaagatata cccgcctcta      420
aagaacttca cttctgcaaa caactaccct gatggtattg gtcagatgca gcatttcgtt      480
aatgacgata aattgagcat tttccgccta cctgtaggat ggcagtacct tgtgaacaat      540
```

-continued

```
aatttgggtg aaccttgga tgcaaacaac cttgccaagt acgaccagct cgttcaggga    600
tgcctgtctc taggtgtaca ctgcattatc gatatacata attatgctcg ctggaatggt    660
gggattattg gtcagggagg cccaacaaat gctcagttca ctagtctttg gtcgcaattg    720
gcatcgaagt acgcatctca accgaaggtg tggttcggaa tcatgaatga gccacacgat    780
gtgaatatta acacttgggc taccactgtg caagccgttg tcactgcaat ccgaagcgcg    840
ggagctacct cgcagttcat ttcgctgcct ggaaatgatt ggcagtctgc tggagctttc    900
atctctgatg gcagtgcagc cgctttatct caagtcaaga ccccgatggc ctcaacaacc    960
aatctgattt tcgacctgca taagtacctg gattcagaca actctggcac tcacgccgaa   1020
tgcactacaa acaacattaa cgatgcgttc tcacctgtcg ccacctggct ccgacagaac   1080
aaccgccagg ctatcctaac cgagactggc ggtggtaaca ctcagtcatg cattcagtat   1140
gtgtgccaac agattcaata tctcaaccaa aactccgacg tctaccttgg ctacgttggg   1200
tggggtgcag gctcatttga cagtacttat atattgacgg agacaccaac tggtagcgga   1260
acctcttgga ccgacacgtc tcttgtaagc tcttgtctct ctcggaaata g           1311
```

<210> SEQ ID NO 58
<211> LENGTH: 436
<212> TYPE: PRT
<213> ORGANISM: Trichoderma fertile

<400> SEQUENCE: 58

```
Met Ala Pro Leu Leu Ala Ala Ala Phe Met Val Ser Gly Ala Val
1               5                   10                  15

Ala Gln Gln Thr Thr Trp Gly Gln Cys Gly Gly Ile Gly Tyr Ser Gly
            20                  25                  30

Pro Thr Asn Cys Val Pro Gly Thr Ala Cys Ser Thr Leu Asn Pro Tyr
        35                  40                  45

Tyr Ala Gln Cys Ile Pro Gly Ala Thr Thr Met Ser Thr Ser Thr Lys
    50                  55                  60

Pro Pro Thr Ser Gly Pro Thr Thr Thr Thr Thr Thr Thr Thr Thr Thr
65                  70                  75                  80

Thr Thr Thr Thr Thr Thr Thr Thr Thr Thr Thr Thr Thr Arg Ser
                85                  90                  95

Thr Ser Thr Ser Ser Ala Ala Pro Pro Thr Gly Ser Gly Leu Thr Gln
            100                 105                 110

Phe Gly Gly Ile Asn Ile Ala Gly Phe Asp Phe Gly Cys Gly Thr Asp
        115                 120                 125

Gly Thr Cys Val Thr Ser Lys Ile Tyr Pro Pro Leu Lys Asn Phe Thr
    130                 135                 140

Ser Ala Asn Asn Tyr Pro Asp Gly Ile Gly Gln Met Gln His Phe Val
145                 150                 155                 160

Asn Asp Asp Lys Leu Ser Ile Phe Arg Leu Pro Val Gly Trp Gln Tyr
                165                 170                 175

Leu Val Asn Asn Asn Leu Gly Gly Thr Leu Asp Ala Asn Asn Leu Ala
            180                 185                 190

Lys Tyr Asp Gln Leu Val Gln Gly Cys Leu Ser Leu Gly Val His Cys
        195                 200                 205

Ile Ile Asp Ile His Asn Tyr Ala Arg Trp Asn Gly Gly Ile Ile Gly
    210                 215                 220

Gln Gly Gly Pro Thr Asn Ala Gln Phe Thr Ser Leu Trp Ser Gln Leu
225                 230                 235                 240
```

```
Ala Ser Lys Tyr Ala Ser Gln Pro Lys Val Trp Phe Gly Ile Met Asn
            245                 250                 255

Glu Pro His Asp Val Asn Ile Asn Thr Trp Ala Thr Thr Val Gln Ala
        260                 265                 270

Val Val Thr Ala Ile Arg Ser Ala Gly Ala Thr Ser Gln Phe Ile Ser
    275                 280                 285

Leu Pro Gly Asn Asp Trp Gln Ser Ala Gly Ala Phe Ile Ser Asp Gly
290                 295                 300

Ser Ala Ala Leu Ser Gln Val Lys Asn Pro Asp Gly Ser Thr Thr
305                 310                 315                 320

Asn Leu Ile Phe Asp Leu His Lys Tyr Leu Asp Ser Asp Asn Ser Gly
                325                 330                 335

Thr His Ala Glu Cys Thr Thr Asn Asn Ile Asn Asp Ala Phe Ser Pro
            340                 345                 350

Val Ala Thr Trp Leu Arg Gln Asn Asn Arg Gln Ala Ile Leu Thr Glu
        355                 360                 365

Thr Gly Gly Gly Asn Thr Gln Ser Cys Ile Gln Tyr Val Cys Gln Gln
    370                 375                 380

Ile Gln Tyr Leu Asn Gln Asn Ser Asp Val Tyr Leu Gly Tyr Val Gly
385                 390                 395                 400

Trp Gly Ala Gly Ser Phe Asp Ser Thr Tyr Ile Leu Thr Glu Thr Pro
                405                 410                 415

Thr Gly Ser Gly Thr Ser Trp Thr Asp Thr Ser Leu Val Ser Ser Cys
            420                 425                 430

Leu Ser Arg Lys
        435

<210> SEQ ID NO 59
<211> LENGTH: 1272
<212> TYPE: DNA
<213> ORGANISM: Trichoderma fertile

<400> SEQUENCE: 59
atggccaaca ccaaggctgc actgctgctt gcagcctatg ttgcagcgag tggtgtcgtg      60
gcacaacaga ctacctgggg acaatgcgga gggataggct atggtggccc gtcgagttgt     120
gtttctgggg cggcgtgctc aacacagaat tcatattatg cccagtgtgt ccctgctacc     180
ggcttgacca ccagcaccaa acctgcgaca gcatcgacaa cagcgacaac aacgacaaca     240
tcgaaaacaa cgacaacctc ggcaggctcg tctccaccgc ccaccggcac ggggacccag     300
tttgccggta ttaacattgc tggattcgac tttggctgtt cgactgacgg aacctgcaac     360
gtgcccgctg tctatccgcc actgaagaat ttcgatggcg caaacaacta tccagatggc     420
gttgggcaga tgcaacattt tgtgaatgat gacaaactca atattttccg cctacctgtg     480
ggttggcagt atctagtgaa caacaacctt ggtggcacca tcaacgcgac caatttggcc     540
gtgtatgatc aactggtcca gggatgccta gccacaggtt catactgtat cgtcgacatc     600
cacaactatg ctcgctggaa cggccaaatc attggccagg cggtcctac aaacgcccaa      660 ttcgttagtc tctggacaca attggcgacc aagtatgcct cacagcccaa gatatggttt     720
ggcattatga atgaaccaca cgaccttaac gtcaccactt gggccgttac tgtgcaggct     780
gttgttactg caatccgtaa tgcgggtgct acctcgcagt atatctcact gccgggcagt     840
gactatcagt ctgccggatc tgtcatttcc gatggtagtg cagcggcttt aggtgctatc     900
accaatccca acggctcaaa gaccaacctc attttcgatg tgcataagta cttggactcg     960
```

```
gataactctg gtactagctc agactgtgtt acgaacaaca ttgcaactgc attctcgccg   1020
ctagctacct ggctccgttc caacaatcgc caggctattc tgactgagac tggtggtggc   1080
aacacttcat cttgtgaaca gtacctttgc cagcagatcc agtatctcaa ccagaactcc   1140
gatgtctatc ttggatatgt tggatgggct gcgggctcct tcgatcccgg ctacccattg   1200
gctgagaccc cggttgacaa tggaagcgcc tggactgatc aaccctggt gaagctttgc    1260 cttgcccgtt ga                                                       1272
```

<210> SEQ ID NO 60
<211> LENGTH: 423
<212> TYPE: PRT
<213> ORGANISM: Trichoderma fertile

<400> SEQUENCE: 60

```
Met Ala Asn Thr Lys Ala Ala Leu Leu Ala Ala Tyr Val Ala Ala
1               5                   10                  15

Ser Gly Val Val Ala Gln Gln Thr Thr Trp Gly Gln Cys Gly Gly Ile
                20                  25                  30

Gly Tyr Gly Gly Pro Ser Ser Cys Val Ser Gly Ala Ala Cys Ser Thr
            35                  40                  45

Gln Asn Ser Tyr Tyr Ala Gln Cys Val Pro Ala Thr Gly Leu Thr Thr
        50                  55                  60

Ser Thr Lys Pro Ala Thr Ala Ser Thr Thr Ala Thr Thr Thr Thr Thr
65                  70                  75                  80

Ser Lys Thr Thr Thr Thr Ser Ala Gly Ser Ser Pro Pro Thr Gly
                85                  90                  95

Thr Gly Thr Gln Phe Ala Gly Ile Asn Ile Ala Gly Phe Asp Phe Gly
            100                 105                 110

Cys Ser Thr Asp Gly Thr Cys Asn Val Pro Ala Val Tyr Pro Pro Leu
        115                 120                 125

Lys Asn Phe Asp Gly Ala Asn Asn Tyr Pro Asp Gly Val Gly Gln Met
    130                 135                 140

Gln His Phe Val Asn Asp Asp Lys Leu Asn Ile Phe Arg Leu Pro Val
145                 150                 155                 160

Gly Trp Gln Tyr Leu Val Asn Asn Asn Leu Gly Gly Thr Ile Asn Ala
                165                 170                 175

Thr Asn Leu Ala Val Tyr Asp Gln Leu Val Gln Gly Cys Leu Ala Thr
            180                 185                 190

Gly Ser Tyr Cys Ile Val Asp Ile His Asn Tyr Ala Arg Trp Asn Gly
        195                 200                 205

Gln Ile Ile Gly Gln Gly Gly Pro Thr Asn Ala Gln Phe Val Ser Leu
    210                 215                 220

Trp Thr Gln Leu Ala Thr Lys Tyr Ala Ser Gln Pro Lys Ile Trp Phe
225                 230                 235                 240

Gly Ile Met Asn Glu Pro His Asp Leu Asn Val Thr Trp Ala Val
                245                 250                 255

Thr Val Gln Ala Val Val Thr Ala Ile Arg Asn Ala Gly Ala Thr Ser
            260                 265                 270

Gln Tyr Ile Ser Leu Pro Gly Ser Asp Tyr Gln Ser Ala Gly Ser Val
        275                 280                 285

Ile Ser Asp Gly Ser Ala Ala Leu Gly Ala Ile Thr Asn Pro Asn
    290                 295                 300

Gly Ser Lys Thr Asn Leu Ile Phe Asp Val His Lys Tyr Leu Asp Ser
```

```
            305                 310                 315                 320
Asp Asn Ser Gly Thr Ser Ser Asp Cys Val Thr Asn Asn Ile Ala Thr
                325                 330                 335

Ala Phe Ser Pro Leu Ala Thr Trp Leu Arg Ser Asn Asn Arg Gln Ala
                340                 345                 350

Ile Leu Thr Glu Thr Gly Gly Gly Asn Thr Ser Ser Cys Glu Gln Tyr
                355                 360                 365

Leu Cys Gln Gln Ile Gln Tyr Leu Asn Gln Asn Ser Asp Val Tyr Leu
                370                 375                 380

Gly Tyr Val Gly Trp Ala Ala Gly Ser Phe Asp Pro Gly Tyr Pro Leu
385                 390                 395                 400

Ala Glu Thr Pro Val Asp Asn Gly Ser Ala Trp Thr Asp Gln Pro Leu
                    405                 410                 415

Val Lys Leu Cys Leu Ala Arg
                420

<210> SEQ ID NO 61
<211> LENGTH: 825
<212> TYPE: DNA
<213> ORGANISM: Trichoderma gamsii
<220> FEATURE:
<221> NAME/KEY: Intron
<222> LOCATION: (408)..(465)
<220> FEATURE:
<221> NAME/KEY: Intron
<222> LOCATION: (687)..(751)

<400> SEQUENCE: 61
atgaagttcc ttcagattgc gcctacacta ttgccagtgg ctctcgccca agctcctgt       60 agccaatacg caacgttctc tggcggcaac tatgcactga gcaacaacct ctggggacaa    120
accgccggca ctggttctgg ctgtatcacc gatgtatcct gggcggctc cgccgtgtgg      180 tcaacgacct ggaactggtc tggaggccag aacaacgtca agggatacccc caacattgca   240 ctcaacatcc caaataaacg acttgtcagc agtatctcaa gcatgccac cactgcccag     300 tggagctaca ctggcagcag cattcgcgca gatgtggcct atgatctctt tactgcgtca    360
aatcccaacc atgtgaccta ttctggagac tatgaactca tgatttggta agtcagcgag    420
atcactgctc atgacttgta ggctaaacag caattctatt tgcaggctcg gaaaatacgg    480
agatgtccag cccattggat cctctcaggg aacggttaac atcggtggca cgagctggaa    540
tctctggtac ggctacaatg gcgccatgca agtatacagc ttcgtggcac cgggcaacct    600
caccaactgg agtggagatg tcaagaactt ttacacgtat ctgcagaaca caagggtta    660 tcctgcctca agccaatatg tcctcagtat gtcattccag cattgatcac gcgaactacc    720
tatggtttat aactaactgg ctgcttaaca ggttaccaat ttggcactga ggccttcact    780
ggaagcggaa cattgaataa cacttggaca gcgtctatta actaa                    825

<210> SEQ ID NO 62
<211> LENGTH: 233
<212> TYPE: PRT
<213> ORGANISM: Trichoderma gamsii

<400> SEQUENCE: 62

Met Lys Phe Leu Gln Ile Ala Pro Thr Leu Leu Pro Val Ala Leu Ala
1               5                   10                  15

Gln Ser Ser Cys Ser Gly Tyr Ala Thr Phe Ser Gly Gly Asn Tyr Ala
                20                  25                  30
```

Leu Ser Asn Asn Leu Trp Gly Gln Thr Ala Gly Thr Gly Ser Gly Cys
    35                  40                  45

Ile Thr Asp Val Ser Leu Gly Gly Ser Ala Val Trp Ser Thr Thr Trp
50                  55                  60

Asn Trp Ser Gly Gly Gln Asn Val Lys Gly Tyr Pro Asn Ile Ala
65                  70                  75                  80

Leu Asn Ile Pro Asn Lys Arg Leu Val Ser Ile Ser Ser Met Pro
                85                  90                  95

Thr Thr Ala Gln Trp Ser Tyr Thr Gly Ser Ser Ile Arg Ala Asp Val
            100                 105                 110

Ala Tyr Asp Leu Phe Thr Ala Ser Asn Pro Asn His Val Thr Tyr Ser
            115                 120                 125

Gly Asp Tyr Glu Leu Met Ile Trp Leu Gly Lys Tyr Gly Asp Val Gln
130                 135                 140

Pro Ile Gly Ser Ser Gln Gly Thr Val Asn Ile Gly Gly Thr Ser Trp
145                 150                 155                 160

Asn Leu Trp Tyr Gly Tyr Asn Gly Ala Met Gln Val Tyr Ser Phe Val
            165                 170                 175

Ala Pro Gly Asn Leu Thr Asn Trp Ser Gly Asp Val Lys Asn Phe Tyr
            180                 185                 190

Thr Tyr Leu Gln Asn Asn Lys Gly Tyr Pro Ala Ser Ser Gln Tyr Val
            195                 200                 205

Leu Ser Tyr Gln Phe Gly Thr Glu Ala Phe Thr Gly Ser Gly Thr Leu
            210                 215                 220

Asn Asn Thr Trp Thr Ala Ser Ile Asn
225                 230

<210> SEQ ID NO 63
<211> LENGTH: 820
<212> TYPE: DNA
<213> ORGANISM: Trichoderma harzianum
<220> FEATURE:
<221> NAME/KEY: Intron
<222> LOCATION: (414)..(466)
<220> FEATURE:
<221> NAME/KEY: Intron
<222> LOCATION: (688)..(740)

<400> SEQUENCE: 63

| | | | | | |
|---|---|---|---|---|---|
| atgaaggcct | tttcattttt | ggctgcgttg | ctgccagccg | tagctgcgca | aactctttgc | 60 |
| gaccagtact | cgaccatctc | ggccaacggt | ttcaccatca | gtaacaatct | ctggggcgag | 120 |
| tcatctgcag | atgctggagg | attcggttgt | atcacgaatg | actggatcac | tgatgccacg | 180 |
| gcgtggcacg | ctgactggcg | atggtctggc | agcccctcca | atgtcaagtc | attcccaaac | 240 |
| gtgcaaagaa | atatcggagc | aaagcagttg | gtcagcagca | tcaacagcat | gcccaccggt | 300 |
| gccgtatgga | actataccgg | aaacaacttg | cgcgctgatg | tcgcctacga | cttgttcact | 360 |
| gcctccgacc | ctaaccaccc | aacttactat | ggagactttg | agcttatgat | ctggtaagat | 420 |
| ggaaaaagag | ccgattgtgt | tttcagttac | taatatgatg | aaacaggctt | ggcagatatg | 480 |
| gtgacatcta | ccccattggt | caatcacagg | gcaatgtcaa | cgtcaacggc | caagattggc | 540 |
| agctgtacta | cggctggaat | ggccagatgc | aagtctacag | ctttgttgct | acaaccagg | 600 |
| ttcagaactg | gaacggcgat | gtcaaggcat | tctacaactg | gatggctaca | aaccgaggat | 660 |
| accccattgg | cagccagtac | cttctcagta | agtcgattac | ttgccttggc | gaaagaaacg | 720 |
| gaacattaat | ttctttgaag | gctaccagtt | cggaactgag | ccattctctg | gcgatggcaa | 780 | caccttctgg gtctactact ggaaaggaga tatccaataa                                820

<210> SEQ ID NO 64
<211> LENGTH: 237
<212> TYPE: PRT
<213> ORGANISM: Trichoderma harzianum

<400> SEQUENCE: 64

Met Lys Ala Phe Ser Phe Leu Ala Ala Leu Leu Pro Ala Val Ala Ala
1               5                   10                  15

Gln Thr Leu Cys Asp Gln Tyr Ser Thr Ile Ser Ala Asn Gly Phe Thr
            20                  25                  30

Ile Ser Asn Asn Leu Trp Gly Glu Ser Ser Ala Asp Ala Gly Gly Phe
        35                  40                  45

Gly Cys Ile Thr Asn Asp Trp Ile Thr Asp Ala Thr Ala Trp His Ala
    50                  55                  60

Asp Trp Arg Trp Ser Gly Ser Pro Ser Asn Val Lys Ser Phe Pro Asn
65                  70                  75                  80

Val Gln Arg Asn Ile Gly Ala Lys Gln Leu Val Ser Ser Ile Asn Ser
                85                  90                  95

Met Pro Thr Gly Ala Val Trp Asn Tyr Thr Gly Asn Asn Leu Arg Ala
            100                 105                 110

Asp Val Ala Tyr Asp Leu Phe Thr Ala Ser Asp Pro Asn His Pro Thr
        115                 120                 125

Tyr Tyr Gly Asp Phe Glu Leu Met Ile Trp Leu Gly Arg Tyr Gly Asp
    130                 135                 140

Ile Tyr Pro Ile Gly Gln Ser Gln Gly Asn Val Asn Val Asn Gly Gln
145                 150                 155                 160

Asp Trp Gln Leu Tyr Tyr Gly Trp Asn Gly Gln Met Gln Val Tyr Ser
                165                 170                 175

Phe Val Ala Tyr Asn Gln Val Gln Asn Trp Asn Gly Asp Val Lys Ala
            180                 185                 190

Phe Tyr Asn Trp Met Ala Thr Asn Arg Gly Tyr Pro Ile Gly Ser Gln
        195                 200                 205

Tyr Leu Leu Ser Tyr Gln Phe Gly Thr Glu Pro Phe Ser Gly Asp Gly
    210                 215                 220

Asn Thr Phe Trp Val Tyr Tyr Trp Lys Gly Asp Ile Gln
225                 230                 235

<210> SEQ ID NO 65
<211> LENGTH: 831
<212> TYPE: DNA
<213> ORGANISM: Trichoderma harzianum
<220> FEATURE:
<221> NAME/KEY: Intron
<222> LOCATION: (411)..(466)
<220> FEATURE:
<221> NAME/KEY: Intron
<222> LOCATION: (688)..(754)

<400> SEQUENCE: 65
atgaagttca ttcaaatctt acctgttatc ttgccagtgg ccgtagctca aaccagctgc    60
gaacagtatg cagtgttctc tggtggcaat ggctattcag tcagcaacaa tctctggggg   120
caatctgccg gtagtggctt cggctgcatc actgtaaact cactcaactc agctgcctcg   180
tggcatgcgg actggcagtg gtctggtggc aaaacaacg tcaagtccta tcccaatgtt   240
caaatcgcta ttcctcaaaa gagaattgtc aacagcatcg gcagcatgcc caccactgct   300

```
agctggagct acacggggag caaccttcgc gccgatgtag cttatgatct cttcactgca    360
tcaaatccca accatgtcac ttattccgga gactacgagc tcatgatctg gcaagtctta    420
gaagccacct ttcccgatat ttgactaacc acaaattcat ttttaggctg gcaagatacg    480
gagacattgg ccccattggg tcttctcagg gtacagtgaa catcaatggt cagagctgga    540
cgctctacta cggcttcaac ggagccatgc aagtgtatag ctttgtggct cccagcactg    600
tcaccaattg gagtggagat gtgaagaact tcttcaacta ccttcgagac aacaaaggat    660
acccggcatc aagccaatat gtcctcagta tgtggccttc atatttagtt cactcaaaga    720
tgctttacgt tcgtactaac catgcgcctc ataggttacc aatttggtac tgagcctttt    780
acaggaagtg gaacgctgaa tgtaaattcc tggaccgcat ctatcaactg a             831
```

<210> SEQ ID NO 66
<211> LENGTH: 235
<212> TYPE: PRT
<213> ORGANISM: Trichoderma harzianum

<400> SEQUENCE: 66

```
Met Lys Phe Ile Gln Ile Leu Pro Val Ile Leu Pro Val Ala Val Ala
1               5                  10                  15

Gln Thr Ser Cys Glu Gln Tyr Ala Val Phe Ser Gly Gly Asn Gly Tyr
            20                  25                  30

Ser Val Ser Asn Asn Leu Trp Gly Gln Ser Ala Gly Ser Gly Phe Gly
        35                  40                  45

Cys Ile Thr Val Asn Ser Leu Asn Ser Ala Ala Ser Trp His Ala Asp
    50                  55                  60

Trp Gln Trp Ser Gly Gly Gln Asn Asn Val Lys Ser Tyr Pro Asn Val
65                  70                  75                  80

Gln Ile Ala Ile Pro Gln Lys Arg Ile Val Asn Ser Ile Gly Ser Met
                85                  90                  95

Pro Thr Thr Ala Ser Trp Ser Tyr Thr Gly Ser Asn Leu Arg Ala Asp
            100                 105                 110

Val Ala Tyr Asp Leu Phe Thr Ala Ser Asn Pro Asn His Val Thr Tyr
        115                 120                 125

Ser Gly Asp Tyr Glu Leu Met Ile Trp Leu Ala Arg Tyr Gly Asp Ile
    130                 135                 140

Gly Pro Ile Gly Ser Ser Gln Gly Thr Val Asn Ile Asn Gly Gln Ser
145                 150                 155                 160

Trp Thr Leu Tyr Tyr Gly Phe Asn Gly Ala Met Gln Val Tyr Ser Phe
                165                 170                 175

Val Ala Pro Ser Thr Val Thr Asn Trp Ser Gly Asp Val Lys Asn Phe
            180                 185                 190

Phe Asn Tyr Leu Arg Asp Asn Lys Gly Tyr Pro Ala Ser Ser Gln Tyr
        195                 200                 205

Val Leu Ser Tyr Gln Phe Gly Thr Glu Pro Phe Thr Gly Ser Gly Thr
    210                 215                 220

Leu Asn Val Asn Ser Trp Thr Ala Ser Ile Asn
225                 230                 235
```

<210> SEQ ID NO 67
<211> LENGTH: 834
<212> TYPE: DNA
<213> ORGANISM: Trichoderma sp.
<220> FEATURE:
<221> NAME/KEY: Intron
<222> LOCATION: (411)..(468)

```
<220> FEATURE:
<221> NAME/KEY: Intron
<222> LOCATION: (690)..(757)

<400> SEQUENCE: 67
atgaagctgc ttcaggtttt accagctatc ttgccagtag ctctggccca aaccagctgc    60
gaacagtacg cggtgttctc tggtggtagc ggatatacag tcagcaacaa tctctgggc    120 caatctgccg gtagtggctt tggctgcatc accgtgaact ccctcaactc agctgcctcc   180
tggcatgcag actggcagtg gtctggtggc caaaataatg tcaagtccta tcccaacgtc   240
caggtcggcc ttcccacaaa gagaatcgtc aacagcatca gcagattgcc cactacagtc   300
agctggagct acactggaag caaccttcgc gccgatgtag cttatgatct cttcactgcg   360
tcaaatccca accatgtgac ttattctgga gactacgagc tgatgatctg gcaagtcgta   420
tagactgtct ttgccaatat tttgactaat cagtaattcc actttaggc tcgcaaagta    480 tggagatatc ggccccattg gatcctctca ggggacagtt aatgtcaatg gtcagagctg   540
gacgctctac tacggcttca atggagccat gcaagtctat agctttgttg cccccaccaa   600
taccaccaat tggagtggag atatcaagaa cttcttcaac tatctacgag ataacaaagg   660 ataccccggcc tcaagtcaat atctcctcag tatgtgactc tagttttcgt tttgttacga   720
atatgctttg cggtgatact aatcagatgc ttcttaggtt tccagtttgg tactgagccg    780
tttacaggca gtggaacact gaatgtggga tcttggactg catctatcaa ctaa          834

<210> SEQ ID NO 68
<211> LENGTH: 235
<212> TYPE: PRT
<213> ORGANISM: Trichoderma sp.

<400> SEQUENCE: 68

Met Lys Leu Leu Gln Val Leu Pro Ala Ile Leu Pro Val Ala Leu Ala
1               5                   10                  15

Gln Thr Ser Cys Glu Gln Tyr Ala Val Phe Ser Gly Gly Ser Gly Tyr
                20                  25                  30

Thr Val Ser Asn Asn Leu Trp Gly Gln Ser Ala Gly Ser Gly Phe Gly
            35                  40                  45

Cys Ile Thr Val Asn Ser Leu Asn Ser Ala Ala Ser Trp His Ala Asp
        50                  55                  60

Trp Gln Trp Ser Gly Gly Gln Asn Asn Val Lys Ser Tyr Pro Asn Val
65                  70                  75                  80

Gln Val Gly Leu Pro Thr Lys Arg Ile Val Asn Ser Ile Ser Arg Leu
                85                  90                  95

Pro Thr Thr Val Ser Trp Ser Tyr Thr Gly Ser Asn Leu Arg Ala Asp
            100                 105                 110

Val Ala Tyr Asp Leu Phe Thr Ala Ser Asn Pro Asn His Val Thr Tyr
        115                 120                 125

Ser Gly Asp Tyr Glu Leu Met Ile Trp Leu Ala Lys Tyr Gly Asp Ile
    130                 135                 140

Gly Pro Ile Gly Ser Ser Gln Gly Thr Val Asn Val Asn Gly Gln Ser
145                 150                 155                 160

Trp Thr Leu Tyr Tyr Gly Phe Asn Gly Ala Met Gln Val Tyr Ser Phe
                165                 170                 175

Val Ala Pro Thr Asn Thr Thr Asn Trp Ser Gly Asp Ile Lys Asn Phe
            180                 185                 190

Phe Asn Tyr Leu Arg Asp Asn Lys Gly Tyr Pro Ala Ser Ser Gln Tyr
```

```
                195                 200                 205
Leu Leu Ser Phe Gln Phe Gly Thr Glu Pro Phe Thr Gly Ser Gly Thr
    210                 215                 220

Leu Asn Val Gly Ser Trp Thr Ala Ser Ile Asn
225                 230                 235

<210> SEQ ID NO 69
<211> LENGTH: 817
<212> TYPE: DNA
<213> ORGANISM: Trichoderma fertile
<220> FEATURE:
<221> NAME/KEY: Intron
<222> LOCATION: (408)..(460)
<220> FEATURE:
<221> NAME/KEY: Intron
<222> LOCATION: (682)..(737)

<400> SEQUENCE: 69
atgaaggcct tttcattttt cgctgcactg ctgccagctg tagctgcgca aactctttgc    60
gatcaatact caactatctc ggccaacggc tacaccatca gcaacaatct ctggggcgag   120
tcatctggaa ctggattcgg ttgtatcacg gaagagtgga tcactgatgc cacggcgtgg   180
cacgctgact ggcaatggtc tggcaatccg agcaacgtca agtcatatcc aaacgtgcaa   240
agaaatatag gagcaaagca gctggtcagc tccattaaca gcatgaccac tggcgccgta   300
tggaattaca ctggaaacaa tctgcgagct gatgtcgcct atgacttgtt cactgcttcg   360
gatcccaatc acccgactta ctatggagac tacgaggtta tgatctggta agatgaatgg   420
agagctgatt gtgatttcag ctgctaatat gattaaacag gcttggcaag tatggtgaca   480
tttaccccat tggttcatcc cagggcaacg tcaacgtcaa tggccaagat tggcagctat   540 actacgatg gaacggccag atgcaagtct acagctttgt tgcttacaca cctgtccaga    600
attggaacgg agatatcaaa caattctaca gctggttggc ttcaaacaga ggatacccta   660
ttggcagcca gtaccttctg agtaagtcga ttacttgcct tggtgaaaga aacgaatat    720 taatcaacct ttaataggct accagttcgg aactgagcca ttctctggcg atggaaacac   780
gttctgggtc tactactgga gaggagatat taactaa                            817

<210> SEQ ID NO 70
<211> LENGTH: 235
<212> TYPE: PRT
<213> ORGANISM: Trichoderma fertile

<400> SEQUENCE: 70

Met Lys Ala Phe Ser Phe Ala Ala Leu Leu Pro Ala Val Ala Ala
1               5                   10                  15

Gln Thr Leu Cys Asp Gln Tyr Ser Thr Ile Ser Ala Asn Gly Tyr Thr
            20                  25                  30

Ile Ser Asn Asn Leu Trp Gly Glu Ser Gly Thr Gly Phe Gly Cys
        35                  40                  45

Ile Thr Glu Glu Trp Ile Thr Asp Ala Thr Ala Trp His Ala Asp Trp
    50                  55                  60

Gln Trp Ser Gly Asn Pro Ser Asn Val Lys Ser Tyr Pro Asn Val Gln
65                  70                  75                  80

Arg Asn Ile Gly Ala Lys Gln Leu Val Ser Ser Ile Asn Ser Met Thr
                85                  90                  95

Thr Gly Ala Val Trp Asn Tyr Thr Gly Asn Asn Leu Arg Ala Asp Val
            100                 105                 110
```

```
Ala Tyr Asp Leu Phe Thr Ala Ser Asp Pro Asn His Pro Thr Tyr Tyr
            115                 120                 125

Gly Asp Tyr Glu Val Met Ile Trp Leu Gly Lys Tyr Gly Asp Ile Tyr
130                 135                 140

Pro Ile Gly Ser Ser Gln Gly Asn Val Asn Val Asn Gly Gln Asp Trp
145                 150                 155                 160

Gln Leu Tyr Tyr Gly Trp Asn Gly Gln Met Gln Val Tyr Ser Phe Val
                165                 170                 175

Ala Tyr Thr Pro Val Gln Asn Trp Asn Gly Asp Ile Lys Gln Phe Tyr
            180                 185                 190

Ser Trp Leu Ala Ser Asn Arg Gly Tyr Pro Ile Gly Ser Gln Tyr Leu
        195                 200                 205

Leu Ser Tyr Gln Phe Gly Thr Glu Pro Phe Ser Gly Asp Gly Asn Thr
210                 215                 220

Phe Trp Val Tyr Tyr Trp Arg Gly Asp Ile Asn
225                 230                 235

<210> SEQ ID NO 71
<211> LENGTH: 1283
<212> TYPE: DNA
<213> ORGANISM: Penicillium spinulosum
<220> FEATURE:
<221> NAME/KEY: Intron
<222> LOCATION: (92)..(146)
<220> FEATURE:
<221> NAME/KEY: Intron
<222> LOCATION: (206)..(267)
<220> FEATURE:
<221> NAME/KEY: Intron
<222> LOCATION: (421)..(477)
<220> FEATURE:
<221> NAME/KEY: Intron
<222> LOCATION: (543)..(606)
<220> FEATURE:
<221> NAME/KEY: Intron
<222> LOCATION: (704)..(753)

<400> SEQUENCE: 71
atgagattca gctactttgc tctcttggct gctgcgacat ccgtagcagc atctccactg      60
aaaaatgcga agaaatcttc ttcattcgag tgtgggtgtt cagtatacca taccaagagc    120
aattccaggg ctgataatct atgtagggtt tggagccagc gaatcctgtg ctgagtttgg    180
ttccggcaat attcctggcg tctatgtaag ttacccatgc atataccgag atacctgctg    240
attatcgatc atactcaacg ataacaggga accgactata ttttccccag cacaagcgcc    300
atccaaacct tgattgacga tggcatgaac atcttccgcg tgacgttcct catggagcga    360
ctagtcccca ctaccatggc aggatccttt gacgcggagt atctgagcaa cttgacatac    420
gtacgtggca acccaaagcc ctcgagcttc agttctatta gagattgact aagacaggtt    480
gtgaactata tcaccgaagc cggtgcgcac gcggttctgg acccgcataa ttatggtcga    540
tagtaagccc aacctcttta tttccgcacg caaaatcaag taccgccaag ctgacatctc    600
aacaagctac gactcgatca tcacaagcac atcggatttc agacattttt ggcaaaatgt    660
tgcgaaagaa ttcgcgtcaa attcgttggt aattttcgac accagtgagt gcctttacca    720
cagacatacg ggtacctatg ctcatactcg cagacaacga ataccacgat atggaccaaa    780
ccctcgtctt agacctcaac caggccgcaa tcaacggtat ccgtgcagca ggagcaacaa    840
gccaatacat cttcgtcgaa ggcaattcct ggacaggcgc ctggacctgg acagagtaca    900 acgataaacct ggtcaaccctt accgatcctg aaaacaagat tgtctacgag atgcaccagt    960
```

-continued

```
acctcgactc ggatggatcg ggtaccagct ccacctgtgt ctcgagcacg attggtcagg    1020
agcgcgtgga agctgcgacg caatggctga tcgataacaa caaggttggt gtgttgggtg    1080
aatttgccgg tggtatcaac actgtgtgtg aggaggcgat tgtgggaatg ttggattata    1140
tggaggagaa ttcggcagtt tggaagggtg ctttgtggtg ggctgcgggt ccatggtggg    1200
gctcttatat ctttagtatt gagccgccaa gtggtgtggc ttacacgggg atgatgtcga    1260
ccctggagcc gtattttgcg tag                                             1283
```

<210> SEQ ID NO 72
<211> LENGTH: 331
<212> TYPE: PRT
<213> ORGANISM: Penicillium spinulosum

<400> SEQUENCE: 72

```
Met Arg Phe Ser Tyr Phe Ala Leu Leu Ala Ala Thr Ser Val Ala
1               5                   10                  15

Ala Ser Pro Leu Lys Asn Ala Lys Lys Ser Ser Phe Glu Trp Phe
            20                  25                  30

Gly Ala Ser Glu Ser Cys Ala Glu Phe Gly Ser Gly Asn Ile Pro Gly
        35                  40                  45

Val Tyr Gly Thr Asp Tyr Ile Phe Pro Ser Thr Ser Ala Ile Gln Thr
    50                  55                  60

Leu Ile Asp Asp Gly Met Asn Ile Phe Arg Val Thr Phe Leu Met Glu
65                  70                  75                  80

Arg Leu Val Pro Thr Thr Met Ala Gly Ser Phe Asp Ala Glu Tyr Leu
                85                  90                  95

Ser Asn Leu Thr Tyr Val Val Asn Tyr Ile Thr Glu Ala Gly Ala His
            100                 105                 110

Ala Val Leu Asp Pro His Asn Tyr Gly Arg Tyr Tyr Asp Ser Ile Ile
        115                 120                 125

Thr Ser Thr Ser Asp Phe Gln Thr Phe Trp Gln Asn Val Ala Lys Glu
130                 135                 140

Phe Ala Ser Asn Ser Leu Val Ile Phe Asp Thr Asn Asn Glu Tyr His
145                 150                 155                 160

Asp Met Asp Gln Thr Leu Val Leu Asp Leu Asn Gln Ala Ala Ile Asn
                165                 170                 175

Gly Ile Arg Ala Ala Gly Ala Thr Ser Gln Tyr Ile Phe Val Glu Gly
            180                 185                 190

Asn Ser Trp Thr Gly Ala Trp Thr Trp Thr Glu Tyr Asn Asp Asn Leu
        195                 200                 205

Val Asn Leu Thr Asp Pro Glu Asn Lys Ile Val Tyr Glu Met His Gln
    210                 215                 220

Tyr Leu Asp Ser Asp Gly Ser Gly Thr Ser Ser Thr Cys Val Ser Ser
225                 230                 235                 240

Thr Ile Gly Gln Glu Arg Val Glu Ala Ala Thr Gln Trp Leu Ile Asp
                245                 250                 255

Asn Asn Lys Val Gly Val Leu Gly Glu Phe Ala Gly Gly Ile Asn Thr
            260                 265                 270

Val Cys Glu Glu Ala Ile Val Gly Met Leu Asp Tyr Met Glu Glu Asn
        275                 280                 285

Ser Ala Val Trp Lys Gly Ala Leu Trp Trp Ala Ala Gly Pro Trp Trp
    290                 295                 300

Gly Ser Tyr Ile Phe Ser Ile Glu Pro Pro Ser Gly Val Ala Tyr Thr
305                 310                 315                 320
```

```
Gly Met Met Ser Thr Leu Glu Pro Tyr Phe Ala
            325                 330
```

<210> SEQ ID NO 73
<211> LENGTH: 1444
<212> TYPE: DNA
<213> ORGANISM: Penicillium spinulosum
<220> FEATURE:
<221> NAME/KEY: Intron
<222> LOCATION: (89)..(138)
<220> FEATURE:
<221> NAME/KEY: Intron
<222> LOCATION: (351)..(397)
<220> FEATURE:
<221> NAME/KEY: Intron
<222> LOCATION: (463)..(516)
<220> FEATURE:
<221> NAME/KEY: Intron
<222> LOCATION: (615)..(665)

<400> SEQUENCE: 73

| | | | | | |
|---|---|---|---|---|---|
| atgagataca | ctttgctgct | cgcagccagc | gctgccctgg | ctctcgcgat | gcctcaaggc | 60 |
| cactccaagc | gagcctcgtc | ctttgtttgt | acgtgtagaa | cacaccgaaa | cctagccgaa | 120 |
| actgaccatt | catcgtaggg | tttggcgcaa | gtgagtccgg | agcggagttt | ggcagtggga | 180 |
| atattccggg | tgtactggga | accgactaca | tttggccaga | cacttcggcc | attcaaacgc | 240 |
| tacgcgacgc | gggtatgaac | atctttcggg | tgccgttctt | gatggagcga | ctggttccca | 300 |
| atacattaac | ctcgagtcca | aatgagtcct | atctacaaga | cctgaagagt | gtacgttgtc | 360 |
| cttgtctagt | gttccacccg | tgcttatcag | tttccagacg | gttgaataca | tcacgtctac | 420 |
| cgacgcgtat | gctatcgttg | atccacacaa | cttttgggcga | tagtcagttg | atagtctccg | 480 |
| ctttccaact | ggaaactcca | ctcactagtg | aactagctat | ggcaacatca | tcacctccac | 540 |
| gagtgacttt | gctgcatttt | ggacgaccgt | ggcaacgcag | tttgcatcga | atgacaaggt | 600 |
| catcttcgac | acgagtaagc | ctcaggctct | actagctccc | ttcatcttct | gactgacatc | 660 |
| tgcagacaac | gaatttaaca | cggaggacca | aacactggta | ctggacctca | accaggcggc | 720 |
| catcaacgca | attcgggctg | ctggagccac | ctcgcagtat | atcttcgtgg | aaggaaattc | 780 |
| atggagtggc | gcctggacgt | ggacatcagt | caatagcaat | ctagtcaatc | taacggaccc | 840 |
| caataacaag | atcgtctacg | agatgcacca | gtatctcgac | tcggatggat | ctggcacttc | 900 |
| cgacacatgc | gtcagcacga | ccatcggcca | ggagcgtgta | cagtcagcaa | cagaatggtt | 960 |
| gcaaagcaat | gggaaactag | gttttctggg | cgagtttgct | ggtggtgcta | atacagtctg | 1020 |
| tcagagcgct | gtgactggaa | tgctgagcta | cttgcaagag | aacagtgacg | tctggctcgg | 1080 |
| agcatcctgg | tgggccgcag | gaccatggtg | gggtacctat | atcttttcga | tggagccacc | 1140 |
| ctcagggact | gcatatactt | attaccttga | tatcttgtct | gcctactttc | cttccagttc | 1200 |
| gggcggttcg | ggcgattctg | cgaccacttc | cacaaccaca | cactctacat | cgacaaccac | 1260 |
| cacagcagcc | actaccacca | ctaaagccac | cacaacttca | accaccacca | gcgcagggtc | 1320 |
| taccagtact | gcaacagcct | cccactgggc | gcagtgtggc | ggcagtggct | ggacaggggc | 1380 |
| gacgacatgt | gccagcccat | atacctgcca | ggcgcagaat | gcatactatt | cgcaatgtct | 1440 |
| gtaa | | | | | | 1444 |

<210> SEQ ID NO 74
<211> LENGTH: 414
<212> TYPE: PRT
<213> ORGANISM: Penicillium spinulosum

```
<400> SEQUENCE: 74

Met Arg Tyr Thr Leu Leu Ala Ala Ser Ala Ala Leu Ala Leu Ala
1               5                   10                  15

Met Pro Gln Gly His Ser Lys Arg Ala Ser Ser Phe Val Cys Trp Phe
            20                  25                  30

Gly Ala Ser Glu Ser Gly Ala Glu Phe Gly Ser Gly Asn Ile Pro Gly
                35                  40                  45

Val Leu Gly Thr Asp Tyr Ile Trp Pro Asp Thr Ser Ala Ile Gln Thr
        50                  55                  60

Leu Arg Asp Ala Gly Met Asn Ile Phe Arg Val Pro Phe Leu Met Glu
65                  70                  75                  80

Arg Leu Val Pro Asn Thr Leu Thr Ser Ser Pro Asn Glu Ser Tyr Leu
                85                  90                  95

Gln Asp Leu Lys Ser Thr Val Glu Tyr Ile Thr Ser Thr Asp Ala Tyr
            100                 105                 110

Ala Ile Val Asp Pro His Asn Phe Gly Arg Tyr Gly Asn Ile Ile
            115                 120                 125

Thr Ser Thr Ser Asp Phe Ala Ala Phe Trp Thr Thr Val Ala Thr Gln
        130                 135                 140

Phe Ala Ser Asn Asp Lys Val Ile Phe Asp Thr Asn Asn Glu Phe Asn
145                 150                 155                 160

Thr Glu Asp Gln Thr Leu Val Leu Asp Leu Asn Gln Ala Ala Ile Asn
                165                 170                 175

Ala Ile Arg Ala Ala Gly Ala Thr Ser Gln Tyr Ile Phe Val Glu Gly
            180                 185                 190

Asn Ser Trp Ser Gly Ala Trp Thr Trp Thr Ser Val Asn Ser Asn Leu
        195                 200                 205

Val Asn Leu Thr Asp Pro Asn Asn Lys Ile Val Tyr Glu Met His Gln
210                 215                 220

Tyr Leu Asp Ser Asp Gly Ser Gly Thr Ser Asp Thr Cys Val Ser Thr
225                 230                 235                 240

Thr Ile Gly Gln Glu Arg Val Gln Ser Ala Thr Glu Trp Leu Gln Ser
                245                 250                 255

Asn Gly Lys Leu Gly Phe Leu Gly Glu Phe Ala Gly Gly Ala Asn Thr
            260                 265                 270

Val Cys Gln Ser Ala Val Thr Gly Met Leu Ser Tyr Leu Gln Glu Asn
        275                 280                 285

Ser Asp Val Trp Leu Gly Ala Ser Trp Trp Ala Ala Gly Pro Trp Trp
290                 295                 300

Gly Thr Tyr Ile Phe Ser Met Glu Pro Pro Ser Gly Thr Ala Tyr Thr
305                 310                 315                 320

Tyr Tyr Leu Asp Ile Leu Ser Ala Tyr Phe Pro Ser Ser Gly Gly
                325                 330                 335

Ser Gly Asp Ser Ala Thr Thr Ser Thr Thr His Ser Thr Ser
            340                 345                 350

Thr Thr Thr Ala Ala Thr Thr Thr Lys Ala Thr Thr Thr Ser Thr
        355                 360                 365

Thr Thr Ser Ala Gly Ser Thr Ser Thr Ala Thr Ser His Trp Ala
        370                 375                 380

Gln Cys Gly Gly Ser Gly Trp Thr Gly Ala Thr Thr Cys Ala Ser Pro
385                 390                 395                 400

Tyr Thr Cys Gln Ala Gln Asn Ala Tyr Tyr Ser Gln Cys Leu
```

<210> SEQ ID NO 75
<211> LENGTH: 1408
<212> TYPE: DNA
<213> ORGANISM: Penicillium griseofulvum
<220> FEATURE:
<221> NAME/KEY: Intron
<222> LOCATION: (98)..(152)
<220> FEATURE:
<221> NAME/KEY: Intron
<222> LOCATION: (365)..(416)
<220> FEATURE:
<221> NAME/KEY: Intron
<222> LOCATION: (482)..(531)
<220> FEATURE:
<221> NAME/KEY: Intron
<222> LOCATION: (630)..(677)

<400> SEQUENCE: 75

```
atgcgatata catctttact taccatggct ggtgtcactg gcctggtgct cgcagcacca      60
gggccatcta tatccaaaag gacaccttcg tttgtctgta tgaaatgcaa ctatcctggc     120
ttaaactagt tatctgacca ggtcttgaat agggttcggc gcaaacgaag ctggtgcgga     180
gtttgggagt ggaaatcttc caggagtact gggcacagat tatatctggc catcgacctc     240
agccatccaa actttgagga gtgcagggat gaatctattc cgtgttccct tcgcaatgga     300
gcgattggtt cccgggactc tgactgcgag tccggatgcc acctacctag ctgcattgaa     360
aagtgtatgt gctatagcct tttgcacata aaacattgat accaataccc caacagactg     420
tcaactctat cacgtctagc ggtgcatatg ctgtgattga tcctcacaac tttggaagat     480
agtaagttcc attgccttac agggaggatt aatctgacca tatatatata gttatggcaa     540
aatcatcacc tcgactactg actttgcagc attttggaag atgctcgcat cagaattcgc     600
gtcaaatgac aaggtcatct ttgacacaag tgagatacac tatttctctc ccggaaagcc     660
gtacactgac tttgtagaca atgaattcaa ttcggaagag cagaccctgg tgttggactt     720
gaaccaagca gccatcaatg ctatccgagc tgcaggagcc aaatcgcaat atatcttcgt     780
ggagggcaac tcgtggagtg gcgcatggac ctggccaact gtcaatgaca atatgaaagc     840
cttaacagat ccacaagact tgattgtcta tgagatgcac cagtatcttg actcggatgg     900
ttctgggaca tctgagacct gtgttagctc aaccattggc caagaacgag ttgtggctgc     960
cacacagtgg cttaaggaca atggcaagaa ggccttcttg ggtgaatttg ctggaggccc    1020
caattctgtc tgtaaaagtg ccgtgacagg tatgcttgat tatttacagg caaacagcga    1080
tgtctggctt ggtgcgtcgt ggtggtccgc tggcccatgg tggggaaact acatgtacag    1140
ctttgagcct ccttctggca ctgcctatac ttactacatg agtctcctga aaaattactt    1200
ccctggctcg ggtagtcctg ggacaaccac ctcagtcacc acttctacaa caaccgccgc    1260
tactaccaag accaccacaa cagggccaac catcactggt gcacctcact atgcgcaatg    1320
tggtggagat agctggaccg ggccgaccac ctgtgccagc ccatacacct gccagaagca    1380
gaatgactac tactcgcagt gtctgtag                                        1408
```

<210> SEQ ID NO 76
<211> LENGTH: 400
<212> TYPE: PRT
<213> ORGANISM: Penicillium griseofulvum

<400> SEQUENCE: 76

Met Arg Tyr Thr Ser Leu Leu Thr Met Ala Gly Val Thr Gly Leu Val

```
1               5                   10                  15
Leu Ala Ala Pro Gly Pro Ser Ile Ser Lys Arg Thr Pro Ser Phe Val
            20                  25                  30
Trp Phe Gly Ala Asn Glu Ala Gly Ala Glu Phe Gly Ser Gly Asn Leu
            35                  40                  45
Pro Gly Val Leu Gly Thr Asp Tyr Ile Trp Pro Ser Thr Ser Ala Ile
 50                  55                  60
Gln Thr Leu Arg Ser Ala Gly Met Asn Leu Phe Arg Val Pro Phe Ala
 65                  70                  75                  80
Met Glu Arg Leu Val Pro Gly Thr Leu Thr Ala Ser Pro Asp Ala Thr
            85                  90                  95
Tyr Leu Ala Ala Leu Lys Ser Thr Val Asn Ser Ile Thr Ser Ser Gly
            100                 105                 110
Ala Tyr Ala Val Ile Asp Pro His Asn Phe Gly Arg Ser Tyr Gly Lys
            115                 120                 125
Ile Ile Thr Ser Thr Thr Asp Phe Ala Ala Phe Trp Lys Met Leu Ala
 130                 135                 140
Ser Glu Phe Ala Ser Asn Asp Lys Val Ile Phe Asp Thr Asn Asn Glu
 145                 150                 155                 160
Phe Asn Ser Glu Glu Gln Thr Leu Val Leu Asp Leu Asn Gln Ala Ala
            165                 170                 175
Ile Asn Ala Ile Arg Ala Ala Gly Ala Lys Ser Gln Tyr Ile Phe Val
            180                 185                 190
Glu Gly Asn Ser Trp Ser Gly Ala Trp Thr Trp Pro Thr Val Asn Asp
            195                 200                 205
Asn Met Lys Ala Leu Thr Asp Pro Gln Asp Leu Ile Val Tyr Glu Met
 210                 215                 220
His Gln Tyr Leu Asp Ser Asp Gly Ser Gly Thr Ser Glu Thr Cys Val
 225                 230                 235                 240
Ser Ser Thr Ile Gly Gln Glu Arg Val Val Ala Ala Thr Gln Trp Leu
            245                 250                 255
Lys Asp Asn Gly Lys Lys Ala Phe Leu Gly Glu Phe Ala Gly Gly Pro
            260                 265                 270
Asn Ser Val Cys Lys Ser Ala Val Thr Gly Met Leu Asp Tyr Leu Gln
            275                 280                 285
Ala Asn Ser Asp Val Trp Leu Gly Ala Ser Trp Trp Ser Ala Gly Pro
            290                 295                 300
Trp Trp Gly Asn Tyr Met Tyr Ser Phe Glu Pro Pro Ser Gly Thr Ala
 305                 310                 315                 320
Tyr Thr Tyr Tyr Met Ser Leu Leu Lys Asn Tyr Phe Pro Gly Ser Gly
            325                 330                 335
Ser Pro Gly Thr Thr Thr Ser Val Thr Ser Thr Thr Thr Ala Ala
            340                 345                 350
Thr Thr Lys Thr Thr Thr Thr Gly Pro Thr Ile Thr Gly Ala Pro His
            355                 360                 365
Tyr Ala Gln Cys Gly Gly Asp Ser Trp Thr Gly Pro Thr Thr Cys Ala
            370                 375                 380
Ser Pro Tyr Thr Cys Gln Lys Gly Asn Asp Tyr Tyr Ser Gln Cys Leu
 385                 390                 395                 400

<210> SEQ ID NO 77
<211> LENGTH: 1193
<212> TYPE: DNA
<213> ORGANISM: Fusarium cf. equiseti
```

```
<220> FEATURE:
<221> NAME/KEY: Intron
<222> LOCATION: (346)..(407)

<400> SEQUENCE: 77
atgaagtcct tcctcgccct cagcctcttc actggcctct cagtcgccca aagcgccgct      60
tgggcccaat gcggtggtca aggcttctcc ggtgacaagt cctgcgtctc tggctacaag     120
tgcaccgtcg tcaacgagtg gtaccaccaa tgccagcccg gcaccgcaga gcctccttcc     180
actaccctca agaccaccac aggcagtggt tcccaaccca ctggtactcc cgatggaaag     240
ttcctctggg tcggtaccaa cgaggccggt gctgagtttg gagagaagaa ccttcctggt     300
acttggggaa cgcactttac tttccctgaa cctgctgctg ttgatgtaag tacactccat     360
gaagttacat ggcagatact aacatgtgcc agaccctcat ctctcagggt tacaacactt     420
tccgtgttca gctcaagatg gaacgttcaa accccagcgg aatgaccggc gcgtatgact     480
cagcgtacat gaaaaacctc acttccatcg tgaaccacat caccggcaag ggcgccaccg     540
ttcttctcga ccccacaac tacggccgct acttcgacaa gattatcacc tcgacctctg     600
acttccagac ctggtggaag aactttgcca ctctgttcaa gagcaacagc cgcatcatgt     660
ttgacaccaa caatgagtac cacaccatgg accagaccct gtcctaaac ctcaaccaag     720
ccgccatcaa cggtatccga gctgctggcg ccacgcagta catctttgtc gaaggcaacc     780
aatggtccgg cgcatggtcg tggcccgatg taaacgacaa catgaaggct cttaccgacc     840
cagagaacaa gctcatctac gagatgcacc agtacctcga ctccgactca tccggtactt     900
cacctaactg tgtttccaca accattggtg ttgagcgtct gcaggctgct accaagtggc     960
tccgtgacaa caagaaggtc ggcatgattg gagagtttgc tggcggtcct aacgagactt    1020
gcaagaccgc tgttaagaac atgcttgact ttatgaagaa gaacactgat gtctggaagg    1080
gctttacttg gtgggctgct ggtccttggt ggggtgacta catgtacagc tttgagccta    1140
caagcggtgt tgcttaccag tactacaact ctcttctcaa gacttacatc tag           1193

<210> SEQ ID NO 78
<211> LENGTH: 376
<212> TYPE: PRT
<213> ORGANISM: Fusarium cf. equiseti

<400> SEQUENCE: 78
```

Met Lys Ser Phe Leu Ala Leu Ser Leu Phe Thr Gly Leu Ser Val Ala
1               5                   10                  15

Gln Ser Ala Ala Trp Ala Gln Cys Gly Gly Gln Gly Phe Ser Gly Asp
            20                  25                  30

Lys Ser Cys Val Ser Gly Tyr Lys Cys Thr Val Val Asn Glu Trp Tyr
        35                  40                  45

His Gln Cys Gln Pro Gly Thr Ala Glu Pro Ser Thr Thr Leu Lys
    50                  55                  60

Thr Thr Thr Gly Ser Gly Ser Gln Pro Thr Gly Thr Pro Asp Gly Lys
65                  70                  75                  80

Phe Leu Trp Val Gly Thr Asn Glu Ala Gly Ala Glu Phe Gly Glu Lys
                85                  90                  95

Asn Leu Pro Gly Thr Trp Gly Thr His Phe Thr Phe Pro Glu Pro Ala
            100                 105                 110

Ala Val Asp Gly Tyr Asn Thr Phe Arg Val Gln Leu Lys Met Glu Arg
        115                 120                 125

Ser Asn Pro Ser Gly Met Thr Gly Ala Tyr Asp Ser Ala Tyr Met Lys

```
            130                 135                 140
Asn Leu Thr Ser Ile Val Asn His Ile Thr Gly Lys Gly Ala Thr Val
145                 150                 155                 160

Leu Leu Asp Pro His Asn Tyr Gly Arg Tyr Phe Asp Lys Ile Ile Thr
                165                 170                 175

Ser Thr Ser Asp Phe Gln Thr Trp Trp Lys Asn Phe Ala Thr Leu Phe
            180                 185                 190

Lys Ser Asn Ser Arg Ile Met Phe Asp Thr Asn Glu Tyr His Thr
        195                 200                 205

Met Asp Gln Thr Leu Val Leu Asn Leu Asn Gln Ala Ala Ile Asn Gly
    210                 215                 220

Ile Arg Ala Ala Gly Ala Thr Gln Tyr Ile Phe Val Glu Gly Asn Gln
225                 230                 235                 240

Trp Ser Gly Ala Trp Ser Trp Pro Asp Val Asn Asp Asn Met Lys Ala
                245                 250                 255

Leu Thr Asp Pro Glu Asn Lys Leu Ile Tyr Glu Met His Gln Tyr Leu
                260                 265                 270

Asp Ser Asp Ser Ser Gly Thr Ser Pro Asn Cys Val Ser Thr Thr Ile
        275                 280                 285

Gly Val Glu Arg Leu Gln Ala Ala Thr Lys Trp Leu Arg Asp Asn Lys
    290                 295                 300

Lys Val Gly Met Ile Gly Glu Phe Ala Gly Gly Pro Asn Glu Thr Cys
305                 310                 315                 320

Lys Thr Ala Val Lys Asn Met Leu Asp Phe Met Lys Lys Asn Thr Asp
                325                 330                 335

Val Trp Lys Gly Phe Thr Trp Trp Ala Ala Gly Pro Trp Trp Gly Asp
                340                 345                 350

Tyr Met Tyr Ser Phe Glu Pro Thr Ser Gly Val Ala Tyr Gln Tyr Tyr
        355                 360                 365

Asn Ser Leu Leu Lys Thr Tyr Ile
    370                 375

<210> SEQ ID NO 79
<211> LENGTH: 1095
<212> TYPE: DNA
<213> ORGANISM: Geomyces pannorum
<220> FEATURE:
<221> NAME/KEY: Intron
<222> LOCATION: (180)..(227)
<220> FEATURE:
<221> NAME/KEY: Intron
<222> LOCATION: (657)..(701)

<400> SEQUENCE: 79
atgcatttct cgaaactcgc tgttattgcc agcaccgtgg cgctggccac cgcggccccg      60
tcaaagaagg caaagcgcgc cggaaacttc gaattctttg gcgtcaatga atccggcgct     120
gagttcggca acatgaacct gcctggtgag ctgggaacgg actacatatg ccagtcccg     180 tatgttattt agaatcccct gcgtgacctc gagctaacca tgcaaagagc aaccatcgac     240
acgctcgtcg ctgatggaat gaacatcttc cggattgctt tcatgatgga gcgcctgatc     300
cccgacacgc tgactggaac gcctgacgca acctacctcg ctgacctcaa agagattgtc     360
agctacatca ctggcaaggg agcatacgcg gttatcgacc ccacaacttt cgcacgatac     420
tacggggagg tcatcacaga cacagctggg tttgaggcgt ggtggaagac cgttgccgca     480
gaatttgcgt cggacgcgaa tgtcatcttc gactgtaaca acgagcccca cgacatgcca     540
```

-continued

```
tcaatcgagc tcgttgttga gttgaaccag ggctgcatca acggtatccg tgccgccggt    600
gccactaccc agtccatctt cgtcgaggga acctcctaca gcggtgcctg gacttggtaa    660
gctccccgtt gattcttta gaactgctct aacattctca ggaccacatc cggcaatgac    720
gctctctccg ctctgaccga cccgtcggac aagatcgtct acgagatgca tcaatatctc    780
gacaccgacg gatccggaac gagcgaggat tgtgtctctg ccacgatcgg ccaagagcgc    840
gtccaagctg cgactgaatg gctgcaggcg aacgggaaga agggaatcat tggcgaattc    900
gccggtggcg ccaacgagca gtgcaagtcc gctgttaccg gtatgcttga gtacatggct    960
gccaacaccg acgcgtgggt tggcgccttg tggtggggtg gtggcccatg gtggggagat   1020
tacatgtaca gcatggagcc gccgagtggt attgggtaca cgtactatat cgacaccttg   1080
aagaccctcg gatag                                                    1095
```

<210> SEQ ID NO 80
<211> LENGTH: 333
<212> TYPE: PRT
<213> ORGANISM: Geomyces pannorum

<400> SEQUENCE: 80

Met His Phe Ser Lys Leu Ala Val Ile Ala Ser Thr Val Ala Leu Ala
1               5                   10                  15

Thr Ala Ala Pro Ser Lys Lys Ala Lys Arg Ala Gly Asn Phe Glu Phe
                20                  25                  30

Phe Gly Val Asn Glu Ser Gly Ala Glu Phe Gly Asn Met Asn Leu Pro
            35                  40                  45

Gly Glu Leu Gly Thr Asp Tyr Ile Trp Pro Val Pro Ala Thr Ile Asp
        50                  55                  60

Thr Leu Val Ala Asp Gly Met Asn Ile Phe Arg Ile Ala Phe Met Met
65                  70                  75                  80

Glu Arg Leu Ile Pro Asp Thr Leu Thr Gly Thr Pro Asp Ala Thr Tyr
                85                  90                  95

Leu Ala Asp Leu Lys Glu Ile Val Ser Tyr Ile Thr Gly Lys Gly Ala
                100                 105                 110

Tyr Ala Val Ile Asp Pro His Asn Phe Ala Arg Tyr Tyr Gly Glu Val
            115                 120                 125

Ile Thr Asp Thr Ala Gly Phe Glu Ala Trp Trp Lys Thr Val Ala Ala
        130                 135                 140

Glu Phe Ala Ser Asp Ala Asn Val Ile Phe Asp Cys Asn Asn Glu Pro
145                 150                 155                 160

His Asp Met Pro Ser Ile Glu Leu Val Val Glu Leu Asn Gln Gly Cys
                165                 170                 175

Ile Asn Gly Ile Arg Ala Ala Gly Ala Thr Thr Gln Ser Ile Phe Val
            180                 185                 190

Glu Gly Thr Ser Tyr Ser Gly Ala Trp Thr Trp Thr Thr Ser Gly Asn
        195                 200                 205

Asp Ala Leu Ser Ala Leu Thr Asp Pro Ser Asp Lys Ile Val Tyr Glu
    210                 215                 220

Met His Gln Tyr Leu Asp Thr Asp Gly Ser Gly Thr Ser Glu Asp Cys
225                 230                 235                 240

Val Ser Ala Thr Ile Gly Gln Glu Arg Val Gln Ala Ala Thr Glu Trp
                245                 250                 255

Leu Gln Ala Asn Gly Lys Lys Gly Ile Ile Gly Glu Phe Ala Gly Gly
            260                 265                 270

Ala Asn Glu Gln Cys Lys Ser Ala Val Thr Gly Met Leu Glu Tyr Met
            275                 280                 285

Ala Ala Asn Thr Asp Ala Trp Val Gly Ala Leu Trp Trp Gly Gly Gly
        290                 295                 300

Pro Trp Trp Gly Asp Tyr Met Tyr Ser Met Glu Pro Pro Ser Gly Ile
305                 310                 315                 320

Gly Tyr Thr Tyr Tyr Ile Asp Thr Leu Lys Thr Leu Gly
                325                 330

<210> SEQ ID NO 81
<211> LENGTH: 1283
<212> TYPE: DNA
<213> ORGANISM: Geomyces pannorum
<220> FEATURE:
<221> NAME/KEY: Intron
<222> LOCATION: (373)..(421)
<220> FEATURE:
<221> NAME/KEY: Intron
<222> LOCATION: (686)..(740)

<400> SEQUENCE: 81

| | | | | | |
|---|---|---|---|---|---|
| atgaggttct | accagccttt | gtgcggtgca | ttgctcattg | gtgctgccca | agcacagcag | 60 |
| ggagcatggg | gccaatgtgg | aggaaaaggc | tggactggcc | agacaacatg | cgtgtcaggt | 120 |
| taccattgcg | cctactcgaa | cgactggtac | tctcagtgcg | tccctggtag | tggtggtggt | 180 |
| actactccaa | ccactaccgc | tcctagccaa | ccactaccg | ctcctggtca | aactactaca | 240 |
| tctccaggga | acccttcagc | gacaggcttt | aagtggcttg | tgttgatga | atccggtgct | 300 |
| gagtttggac | agggaagtct | tcctggtgtc | tatggcaagg | acttcatttt | tgcttcgacc | 360 |
| gatgttctcg | gggtatggcc | tccctaaacc | aatacttacc | tcacaactaa | ccgcattata | 420 |
| gtcgcttatg | aaagaaggct | ataacatatt | ccgtgtgcct | ttccttatgg | agcgcatggc | 480 |
| gcccagtggg | gtagggtcgg | cgttctcagc | ggcatatctt | gcgaactaca | ctgttgcaat | 540 |
| caactatatc | actcagaacg | gaggatacgc | tgttattgac | ccccacaact | ttggccgtta | 600 |
| caacggcgct | atcatcacag | atacgaatgc | attcggtatc | ttttttaaga | ccttagcaac | 660 |
| ggcctttaag | aataacgcca | aagttgtaag | tcaacaaccc | cctttccaag | agcttcgtca | 720 |
| ccccaaacta | atacaatcag | attttttgaca | caaacaacga | gtaccatgac | atggaccaaa | 780 |
| ctctggtcct | aaacctaaac | caagctgcca | tcaatgccat | ccgtgccact | ggggccacct | 840 |
| cccaatacat | tttcgtcgag | ggcaactcct | acagcggtgc | ctggacctgg | aacgccgtca | 900 |
| acgacaacct | gaaggcgctc | actgaccctc | agaacaagat | tatctaccag | atgcaccagt | 960 |
| acctcgactc | tgacggatct | gggacgtcgg | caaactgcgt | ctcgtccact | attggcgtcg | 1020 |
| agcgcgtgac | gagcgcgacg | gcatggctgc | gcgcaaatgg | caagattggg | atcattggcg | 1080 |
| agtttgcggg | aggtgccaac | agccagtgca | aggctgctgt | tacggggctg | ctgcagcact | 1140 |
| tgaaggcgaa | ttctgatgtg | tggactggag | ccttgtggtg | gggtggtggt | ccatggtggg | 1200 |
| gtaactacat | ctttgggttt | gagcccccga | gtgggactgg | gtatacctac | tatgattcga | 1260 |
| cccttctgca | gttccgccca | taa | | | | 1283 |

<210> SEQ ID NO 82
<211> LENGTH: 392
<212> TYPE: PRT
<213> ORGANISM: Geomyces pannorum

<400> SEQUENCE: 82

Met Arg Phe Tyr Gln Pro Leu Cys Gly Ala Leu Leu Ile Gly Ala Ala

-continued

```
  1               5                   10                  15
Gln Ala Gln Gln Gly Ala Trp Gly Gln Cys Gly Gly Lys Gly Trp Thr
                 20                  25                  30
Gly Gln Thr Thr Cys Val Ser Gly Tyr His Cys Ala Tyr Ser Asn Asp
                 35                  40                  45
Trp Tyr Ser Gln Cys Val Pro Gly Ser Gly Gly Thr Thr Pro Thr
         50                  55                  60
Thr Thr Ala Pro Ser Gln Thr Thr Thr Ala Pro Gly Gln Thr Thr Thr
 65              70                  75                  80
Ser Pro Gly Asn Pro Ser Ala Thr Gly Phe Lys Trp Leu Gly Val Asp
                 85                  90                  95
Glu Ser Gly Ala Glu Phe Gly Gln Gly Ser Leu Pro Gly Val Tyr Gly
                100                 105                 110
Lys Asp Phe Ile Phe Ala Ser Thr Asp Val Leu Gly Ser Leu Met Lys
                115                 120                 125
Glu Gly Tyr Asn Ile Phe Arg Val Pro Phe Leu Met Glu Arg Met Ala
                130                 135                 140
Pro Ser Gly Val Gly Ser Ala Phe Ser Ala Ala Tyr Leu Ala Asn Tyr
145                 150                 155                 160
Thr Val Ala Ile Asn Tyr Ile Thr Gln Asn Gly Gly Tyr Ala Val Ile
                165                 170                 175
Asp Pro His Asn Phe Gly Arg Tyr Asn Gly Ala Ile Ile Thr Asp Thr
                180                 185                 190
Asn Ala Phe Gly Ile Phe Phe Lys Thr Leu Ala Thr Ala Phe Lys Asn
                195                 200                 205
Asn Ala Lys Val Ile Phe Asp Thr Asn Asn Glu Tyr His Asp Met Asp
210                 215                 220
Gln Thr Leu Val Leu Asn Leu Asn Gln Ala Ala Ile Asn Ala Ile Arg
225                 230                 235                 240
Ala Thr Gly Ala Thr Ser Gln Tyr Ile Phe Val Glu Gly Asn Ser Tyr
                245                 250                 255
Ser Gly Ala Trp Thr Trp Asn Ala Val Asn Asp Asn Leu Lys Ala Leu
                260                 265                 270
Thr Asp Pro Gln Asn Lys Ile Ile Tyr Gln Met His Gln Tyr Leu Asp
                275                 280                 285
Ser Asp Gly Ser Gly Thr Ser Ala Asn Cys Val Ser Ser Thr Ile Gly
                290                 295                 300
Val Glu Arg Val Thr Ser Ala Thr Ala Trp Leu Arg Ala Asn Gly Lys
305                 310                 315                 320
Ile Gly Ile Ile Gly Glu Phe Ala Gly Ala Asn Ser Gln Cys Lys
                325                 330                 335
Ala Ala Val Thr Gly Leu Leu Gln His Leu Lys Ala Asn Ser Asp Val
                340                 345                 350
Trp Thr Gly Ala Leu Trp Trp Gly Gly Pro Trp Trp Gly Asn Tyr
                355                 360                 365
Ile Phe Gly Phe Glu Pro Pro Ser Gly Thr Gly Tyr Thr Tyr Tyr Asp
                370                 375                 380
Ser Thr Leu Leu Gln Phe Arg Pro
385                 390
```

FUNGAL ENDOGLUCANASES, THEIR PRODUCTION AND USE

RELATED APPLICATIONS

This application is a divisional of U.S. application Ser. No. 13/142,630 filed Jun. 29, 2011, which is a continuation-in-part of International application PCT/FI2009/051042, filed Dec. 28, 2009, which claims the benefit of FI patent application number 200860250 filed Dec. 30, 2008, all of which are hereby incorporated herein by reference in their entireties.

FIELD OF THE INVENTION

The invention relates to novel fungal endoglucanases, their production and means for their production. The invention further relates to enzyme preparations comprising at least one novel endoglucanase, as well as to processes for treating cellulosic material therewith. Still further the invention relates to detergent compositions and animal feed comprising the endoglucanases.

BACKGROUND OF THE INVENTION

Cellulases are amongst the most widely used enzymes in industry. They are generally applied in textile industry, detergent industry, pulp and paper industry, feed and food industry, including baking, and in hydrolysis of lignocellulosic material for, e.g. bioethanol production etc. The practical use of cellulases is hampered by the nature of the cellulase compositions, which are often enzyme mixtures having a variety of activities and substrate specificities. For this reason, efforts have been made to obtain cellulases having only the desired activities. The unique properties of each cellulase make some more suitable for certain purposes than others.

In fabric treatment cellulases attack the chains of cellulose molecules that form the cotton fibers, thereby affecting the characteristics of the fabric.

In textile industry a "stone washed" or abraded look has been denim producers' interest in recent years. Traditional stone washing with pumice stones reduces the strength of fabric and burdens the laundering apparatuses. The trend has been towards enzymatic denim finishing processes and cellulases have replaced or are being used together with pumice stones to give the fabric its desired "worn" look. Controlled enzyme treatments result in less damage to the garments and machines and eliminate the need for disposal of stones.

Additionally, textile industry uses cellulases in biofinishing, i.e. to create permanent improvement of depilling, and to improve pilling resistance, clear surface structure by reduced fuzz, improve textile handle, such as softness, smoothness and a silkier feel, improve drapability and brighter colors of the textile and improve moisture absorbability.

Cellulases comprise a catalytic domain/core (CD) expressing cellulase activity. In addition to the catalytic domain the cellulase molecule may comprise one or more cellulose binding domains (CBDs), also named as carbohydrate binding do-mains/modules (CBD/CBM), which can be located either at the N- or C-terminus of the catalytic domain. CBDs have carbohydrate-binding activity and they facilitate the enzymatic action on solid substrates. The catalytic core and the CBD are typically connected via a flexible and highly glycosylated linker region.

Cellulases that attack primarily on the surface of the fiber are especially useful in stone washing of denim dyed with Indigo dye, as the dye is located on the surface of the fiber. Cellulases applied in denim treatment are usually divided into two main groups: acid and neutral cellulases. Acid cellulases typically operate at pH 4.5-5.5 and the neutral cellulases in the range of pH 6-8. When used to treat cotton fabric, acid cellulases generally require a shorter washing time than neutral cellulases. Acid cellulases are especially used in biofinishing (depilling) and also in denim treatment (biostoning). Acid cellulases used in biostoning mainly originate from *Trichoderma reesei* (sexual form *Hypocrea jecorina*) and the neutral cellulases come from a variety of fungi, including genera of *Melanocarpus, Humicola, Thielavia, Myceliophthora, Fusarium, Acremonium*, and *Chrysosporium* (Haakana et al. 2004). *T. reesei* enzymes include, e.g., cellulases from the glycoside family 5 (endoglucanase II, EGII), family 7 (cellobiohydrolase I, CBHI) and family 12 (endoglucanase III, EGIII; Ward et al. 1993), and the neutral cellulases, most often endoglucanases, from family 45 and family 7 (Henrissat, 1991; Henrissat and Bairoch, 1993).

The wide spectrum of industrial uses for endoglucanases has established a need for commercial endoglucanase products showing desired performance at desired conditions such as pH and temperature ranges. Acid cellulases classified as EGII and EGIII have been described for use in i.a. textile treatment. For example WO2007/118935 describes the use of Cel5 (EGII) enzymes in textile finishing. EP 586,375 B1 discloses detergent compositions comprising a thoroughly characterized *Trichoderma* spp. EGIII enzyme with a pH-optimum of 5.5-6.0, pI of 7.2-8.0, and MW of 23-28 kDa. US2007/0026420 describes a method for obtaining genes for novel enzymes, which share certain conserved sequences with EGIII from *Trichoderma reesei*. Properties of the EGIII like cellulases are not exemplified but a temperature in the range of 35° C. to 65° C. is expected to be suitable for these enzymes.

The majority of the industrially used enzymes work better at elevated temperatures, usually about >50° C., but for energy saving reasons, better color fastness and reduction of shrinkage of garments there is a need for enzymes with good performance at lower temperature levels i.e. <50° C., for example about 30 to 40° C., or even 20 to 40° C. Such cold active enzymes have been described e.g. in bacteria, especially in *Bacillus*. However, production of bacterial enzymes for industrial applications is complicated and laborious compared to the production of fungal enzymes. Still there is very little knowledge about possible cold active fungal endoglucanases.

Thus there is a continuous need for new and advantageous endoglucanases having desired properties and thermal profiles. The present invention meets this need.

BRIEF DESCRIPTION OF THE INVENTION

The present invention now provides novel endoglucanases with a unique thermal or pH profile. Unique thermal properties mean that no remarkable decrease in performance can be seen when the temperature is below 50° C. e.g. about 40° C., about 30° C. or even lower. The endoglucanases are useful in different cellulase applications such as fabric treatment, especially denim treatment and depilling. Contrary to previously described Cel5 enzymes, which are typically acid cellulases, we found one novel Cel5 with excellent biostoning effect at neutral pH. This enables biofinishing treatment simultaneously with dyeing, leading to considerable savings. Also the color fastness is often better at neutral conditions.

The present invention provides novel endoglucanases that belong to glycosyl hydrolase family 12 i.e. EGIII polypeptides that may be derived from *Trichoderma* or *Hypocrea*. In particular the invention is directed to a fungal endoglucanase polypeptide, which belongs to glycosyl hydrolase family 12, and which comprises an amino acid sequence having at least 97% sequence identity to SEQ ID NO: 62, at least 60% sequence identity to SEQ ID NO: 64, at least 85% sequence identity to SEQ ID NO: 66, at least 83% sequence identity to SEQ ID NO: 68 or at least 63% sequence identity to SEQ ID NO: 70, or an enzymatically active fragment thereof.

The invention further provides endoglucanases that belong to glycosyl hydrolase family 5 i.e. EGII polypeptides that may be derived from *Trichoderma* or *Hypocrea*. In particular the invention is directed to a fungal endoglucanase polypeptide, which belongs to glycosyl hydrolase family 5, and which comprises an amino acid sequence having at least 77% sequence identity to SEQ ID NO: 42, at least 70% sequence identity to SEQ ID NO: 44, at least 78% sequence identity to SEQ ID NO:46, at least 70% sequence identity to SEQ ID NO: 48, at least 72% sequence identity to SEQ ID NO: 50, at least 78% sequence identity to SEQ ID NO: 52, at least 94% sequence identity to SEQ ID NO: 54, at least 72% sequence identity to SEQ ID NO: 56, at least 82% sequence identity to SEQ ID NO: 58 or at least 73% sequence identity to SEQ ID NO: 60, or an enzymatically active fragment thereof.

Still further the invention provides endoglucanases that belong to glycosyl hydrolase family 5 i.e. EGII polypeptides that may be derived from other fungi than *Trichoderma* or *Hypocrea*, such as *Penicillium, Fusarium* or *Geomyces*. In particular the invention is directed to a fungal endoglucanase polypeptide, which belongs to glycosyl hydrolase family 5, and which comprises an amino acid sequence having at least 70% sequence identity to SEQ ID NO: 72, at least 72% sequence identity to SEQ ID NO: 74, at least 72% sequence identity to SEQ ID NO: 76, at least 91% sequence identity to SEQ ID NO: 78, at least 61% sequence identity to SEQ ID NO: 80 or at least 62% sequence identity to SEQ ID NO: 82, or an enzymatically active fragment thereof.

In addition, the invention is directed to an enzyme preparation comprising said endoglucanase, and detergent compositions and animal feed comprising said enzyme or enzyme preparation.

The invention is further directed to an isolated polynucleotide selected from the group consisting of:
a) a nucleotide sequence having SEQ ID NO: 41, 43, 45, 47, 49, 51, 53, 55, 57, 59, 61, 63, 65, 67, 69, 71, 73, 75, 77, 79, or 81, or a sequence encoding the endoglucanase polypeptide described above,
b) a complementary strand of a), or
c) a sequence that is degenerate as a result of the genetic code to anyone of the sequences of a) or b).

The invention is still further directed to an expression vector comprising said polynucleotide, a host cell comprising said expression vector, and an *E. coli* strain harboring said polynucleotide and having accession number DSM 19418, DSM 18639, DSM 18638, DSM 19963, DSM 18642, DSM 19419, DSM 19894, DSM 19895, DSM 21129, DSM 19898, DSM 18640, DSM 18643, DSM 19420, DSM 19899, DSM 19896, DSM 19960, DSM 19961, DSM 18505, DSM 19172, DSM 18914, or DSM 19962.

Still further the invention provides a method for the production of the endoglucanase polypeptide, comprising the steps of transforming a host cell with an expression vector encoding said polypeptide, and culturing said host cell under conditions enabling expression of said polypeptide, and optionally recovering and purifying said polypeptide.

Finally the invention provides a process for treating cellulosic material, wherein said process comprises contacting the cellulosic material with the endoglucanase polypeptide or enzyme preparation of the invention. An example of such process is a hydrolysis of lignocellulosic biomass for, e.g. bioethanol production.

Specific embodiments of the invention are set forth in the dependent claims. Other objects, details and advantages of the present invention will become apparent from the following drawings, detailed description and examples. It should be understood, however, that the embodiments given in the description, drawings and in the examples are for illustrative purposes only, and that various changes and modifications are possible within the scope of the claims.

DETAILED DESCRIPTION OF THE INVENTION

Figure 1:
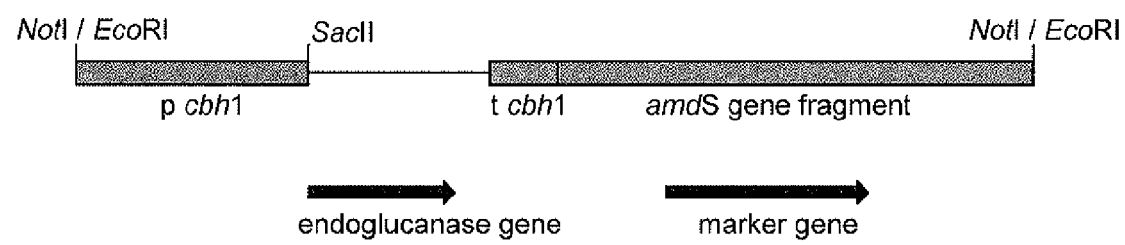
FIG. 1 is a schematic picture of the expression cassettes used in the transformation of *Trichoderma reesei* protoplasts for overproducing the recombinant Cel5 or Cell 2 proteins.

The invention is based on studies, where a fungal culture collection was screened for low-temperature cellulolytic activity. Fungal strains were cultivated at 20° C. for 3-7 days using various production media. Supernatants were recovered and cellulolytic activity against carboxymethylcellulose (CMC) and hydroxyethylcellulase (HEC) at temperatures 30° C. and 50° C. was tested to screen low temperature profiles. The most favorable strains were further tested in small-scale biostoning applications after cultivation at 20° C. for 4-7 days. After preliminary screening 13 strains were selected for construction of genomic libraries, and the libraries were further screened for cel5 and cel12. Positive phage clones were subcloned to bacterial vectors and confirmed by sequencing before deposition at DSMZ. For production of the Cel5 or Cel12 enzymes, the genes encoding desired activities were fused to *Trichoderma reesei* cbh1/cel7A promoter. Transcription termination was ensured by a *T.* reesei cbh1/cel7A terminator, and an amdS marker was used for screening positive clones. Linear expression cassettes were isolated from the vector backbone and transformed into *T. reesei* protoplasts having major cellulases deleted. Purified transformants were cultured for 7 days in cellulase inducing media and endoglucanase activity was tested from the culture supernatant. Thermal and pH properties were also tested. Material for large-scale application was obtained by laboratory bioreactor cultivations at 28° C. lasting for 3-4 days followed by filtration and concentration when needed.

Culture supernatants were tested in denim treatment in different temperatures using one Cel5 and one Cel12 commercial preparations as references in a washing machine. The resulting biostoning effect was evaluated using color reflectance measurement. Most of the enzymes showed excellent performance also at low temperatures in denim application. The enzymes were also found to have an excellent or good depilling effect. Surprisingly a Cel5 enzyme was found to be a neutral cellulase, which is in contrast to the previously described enzymes of this cellulase family, which are known to be acid cellulases.

The present invention provides novel fungal Cel12 endoglucanase polypeptides with substantial performance at low temperatures. The invention further provides novel fungal Cel5 endoglucanase polypeptides with excellent performance at neutral pH. "Polypeptide" and "protein" as used herein are synonyms.

"Fungal" in this context means that the endoglucanase or the polynucleotide encoding it may be derived from a fungus, and especially from a filamentous fungus, such as *Trichoderma, Hypocrea, Penicillium, Geomyces* or *Fusarium*. According to a specific embodiment of the invention the endoglucanase is derived from *T. gamsii, H. rufa/T. viridae, H. atroviridis, T. harzianum, T. fertile, H. koningiopsis, P. spinulosum, P. griseofulvum, G. pannorum* or *F. cf equiseti*. Most preferably the polynucleotide or polypeptide is derived from *Trichoderma* sp. RF6193 (CBS121354), *Trichoderma gamsii* RF6208 (CBS 119563), *Hypocrea rufa/Trichoderma viride* RF6310 (CBS 118970), *Hypocrea atroviridis* RF6323 (CBS 119561), *Trichoderma harzianum* RF6482 (CBS 119562), *Trichoderma harzianum* RF6541 (CBS 119957), *Trichoderma fertile* RF6601 (CBS 121357), *Hypocrea koningiopsis* RF6604 (CBS 119960), *Penicillium spinulosum* RF6286 (CBS 121355), *Penicillium griseofulvum* Dierckx RF6288 (CBS 119565), *Geomyces pannorum* RF6293 (CBS 119567), *Geomyces pannorum* RF6547 (CBS 121356) or *Fusarium cf. equiseti* RF6318 (CBS 119568).

The term "derived from" in connection with a microorganism source means that the polypeptide may naturally be produced by said specific microorganism source, or the polynucleotide encoding the polypeptide may be isolated from said microorganism source, and optionally expressed in a host cell into which the polynucleotide from said microorganism source encoding the polypeptide has been introduced. However, it does not exclude minor modifications of the sequence e.g. by substitution, deletion, and/or insertion of one or a few amino acids/nucleotides as long as the enzymatic activity of the encoded and secreted protein is retained.

"Endoglucanase" ("EG") in connection with the present invention refers to enzymes classified as E.C. 3.2.1.4. They are 1,4-beta-D-glucan 4-glucanohydrolases and catalyze endohydrolysis of 1,4-beta-D-glycosidic linkages in polymers of glucose such as cellulose. Some endoglucanases may also hydrolyse e.g. 1,4-linkages in beta-D-glucans also containing 1,3-linkages. They may therefore also be classified as endo-1,3(4)-beta-glucanases (E.C. 3.2.1.6). Thus, an enzyme may catalyze reactions on several substrates and can belong to multiple classes. The endoglucanases of the invention may optionally contain a signal sequence, and one or more cellulose binding domains (CBDs) linked to the catalytic domain/core (CD).

"Glycosyl hydrolase family 5" and "glycosyl hydrolase family 12" refer to the glycosyl hydrolase families as defined by Henrissat 1991, and Henrissat and Bairoch 1993, 1996, which are incorporated herein by reference. The genes encoding endoglucanases belonging to glycosyl hydrolase family 5 are called cel5 or egl2, and the encoded endoglucanases are called Cel5 or endoglucanase II (EGII). Correspondingly, the genes encoding endoglucanases belonging to glycosyl hydrolase family 12 are called cel12 or egl3, and the encoded endoglucanases are called Cel12 or endoglucanase III (EGIII).

Some of the endoglucanases show substantial performance at low temperature. "Substantial performance" in this context means that the enzymes show excellent performance when applied in at least one type of cellulase application process such as e.g. biostoning and/or biofinishing of textiles, or in washing. "Cold active" or "low temperature" as used herein refers to a temperature of ≤50° C., especially ≤45° C., preferably ≤40° C., including ≤30° C.

According to one embodiment of the invention, the endoglucanase comprises an amino acid sequence having at least 77% sequence identity to SEQ ID NO: 42, at least 70% sequence identity to SEQ ID NO: 44, at least 78% sequence identity to SEQ ID NO: 46, at least 70% sequence identity to SEQ ID NO: 48, at least 72% sequence identity to SEQ ID NO: 50, at least 78% sequence identity to SEQ ID NO: 52, at least 94% sequence identity to SEQ ID NO: 54, at least 72% sequence identity to SEQ ID NO: 56, at least 82% sequence identity to SEQ ID NO:58, at least 73% sequence identity to SEQ ID NO: 60, at least 97% sequence identity to SEQ ID NO: 62, at least 60% sequence identity to SEQ ID NO:64, at least 85% sequence identity to SEQ ID NO: 66, at least 83% sequence identity to SEQ ID NO: 68, at least 63% sequence identity to SEQ ID NO: 70, at least 70% sequence identity to SEQ ID NO: 72, at least 72% sequence identity to SEQ ID NO: 74, at least 72% sequence identity to SEQ ID NO: 76, at least 91% sequence identity to SEQ ID NO: 78, at least 61% sequence identity to SEQ ID NO: 80, or at least 62% sequence identity to SEQ ID NO: 82, or an enzymatically active fragment thereof. Preferably the endoglucanase comprises an amino acid sequence having at least 90%, preferably at least 95% and most preferably at least 98% or 99% sequence identity to SEQ ID NO: 42, 44, 46, 48, 50, 52, 56, 58, 60, 64, 66, 68, 70, 72, 74, 76, 80 or 82, or an enzymatically active fragment thereof, or at least 95% sequence identity to SEQ ID NO: 54 or 78, or at least 98 or 99% sequence identity to SEQ ID NO: 54, 62 or 78, or an enzymatically active fragment thereof.

As used in the present context the term "identity" refers to the global identity between two amino acid sequences compared to each other from the first amino acid encoded by the corresponding gene to the last amino acid. For the purposes of the present invention identity is preferably determined by means of known computer programmes using standard algorithms. An example of such a programme is Clone Manager Suite, a programme that includes the programme part Align Part and is sold by Scientific & Educational Software, Durham, N.C., USA. According to present invention, the programme version "Clone Manager 7 Align Plus 5" including the functions "Compare Two Sequences/Global/Compare DNA sequences" was especially used for determining the degree of identity. In this case algorithms available from the following sources were used: Hirschberg, D. S. (1975) A linear space algorithm for computing longest common subsequences, Commun. Assoc. Comput. Mach. 18: 341-343; Myers, E. W. and W. Miller. (1988) Optimal alignments in linear space, CABIOS 4:1, 11-17; Chao, K-M, W. R. Pearson and W. Miller. (1992) Aligning two sequences within a specified diagonal band, CA-BIOS 8:5, 481-487. The man skilled in the art is aware of the fact that results are comparative only when aligning corresponding domains of the sequence. Consequently comparison of e.g. cellulase sequences including CBD or signal sequences with sequences lacking those elements are excluded as not being meaningful.

"Enzymatically active fragment" refers to part of a specific amino acid sequence that is long enough to have the desired enzymatic activity. In other words a fragment may be e.g. only the mature part of the polypeptide or even a subsequence of the mature part. It may or may not contain a linker and CBD domain. More specifically enzymatic activity refers to cellulase activity that has catalytic ability to hydrolyse cellulose or derivatives thereof, such as endoglucanase or beta-glucanase activity. In addition to endoglucanase and/or beta-glucanase activity, some of the cellulases may further have hemicellulase and/or xylanase activity. The enzymatic activity may be determined as described in Example 1.

The polynucleotides of the invention may be either DNA or RNA. According to one embodiment of the invention the endoglucanases are encoded by a polynucleotide having SEQ ID NO: 41, 43, 45, 47, 49, 51, 53, 55, 57, 59, 61, 63, 65, 67, 69, 71, 73, 75, 77, 79 or 81, or a fragment thereof long enough to encode an enzymatically active endoglucanase. Preferably the endoglucanases are encoded by a polynucleotide similar to that carried by *E. coli* DSM 19418, DSM 18639, DSM 18638, DSM 19963, DSM 18642, DSM 19419, DSM 19894, DSM 19895, DSM 21129, DSM 19898, DSM 18640, DSM 18643, DSM 19420, DSM 19899, DSM 19896, DSM 19960, DSM 19961, DSM 18505, DSM 19172, DSM 18914, or DSM 19962.

The endoglucanases of the invention are preferably recombinant proteins. They are conveniently prepared by generally known recombinant DNA technology in a heterologous or homologous host. Preferably the endoglucanase is overexpressed in a fungal host. Briefly the polynucleotide encoding the endoglucanase is cloned and inserted into an expression vector, transformed into a host cell and expressed.

An "expression vector" is a cloning plasmid or vector capable of expressing DNA encoding the endoglucanase proteins after transformation into a desired host. When a fungal host is used, the gene of interest is preferably provided to a fungal host as part of a cloning or expression vehicle that integrates into the fungal chromosome, or allows the gene of interest to integrate into the host chromosome. Other sequences that are part of the cloning vehicle or expression vehicle may also be integrated with said DNA during the integration process. In addition, in fungi the expression vector or parts thereof can be targeted into predetermined loci. Alternatively, the desired gene can be provided as an autonomously replicating plasmid.

The DNA encoding the endoglucanase proteins is preferably placed under the control of (i.e., operably linked to) certain control sequences such as promoter sequences provided by the vector. Upon transformation these control sequences integrate into the host genome with the gene of interest. Alternatively, the control sequences can be those at the integration site.

The expression control sequences of an expression vector will vary depending on whether the vector is designed to express a certain gene in a prokaryotic or in a eukaryotic host. Expression control sequences can contain transcriptional regulatory elements such as promoters, enhancer elements, and transcriptional termination sequences, and/or translational regulatory elements, such as translational initiation and termination sites.

A polynucleotide molecule, such as DNA, is said to be capable of expressing a polypeptide, if it contains expression control sequences, which contain transcriptional regulatory information and such sequences are operably linked to the nucleotide sequence, which encodes the polypeptide.

An operable linkage is a linkage in which a sequence is connected to a regulatory sequence (or sequences) in such a way as to place expression of the sequence under the influence or control of the regulatory sequence. Two DNA sequences (such as a promoter region sequence linked to the 5' end of the protein encoding sequence) are said to be operably linked if function of the promoter results in transcription.

The vectors of the invention may further comprise other operably linked regulatory elements, such as enhancer sequences.

In a preferred embodiment, genetically stable transformants are constructed, whereby the DNA encoding the proteins is integrated into the host chromosome by transformation with a vector, which may harbor sequences promoting integration of said vector into the chromosome.

Cells that have stably integrated DNA encoding the endoglucanase proteins into their chromosomes may be selected e.g. by introduced marker(s), homologous or heterologous, which allow for selection of host cells which contain the expression vector in the chromosome, for example the marker may provide biocide resistance, e.g., resistance to antibiotics, or heavy metals, such as copper, or markers complementing an auxotrophic mutation in the host chromosome, and the like. The selectable marker can for example be a selection gene directly linked to the DNA gene sequences to be expressed, or introduced into the same cell by co-transformation. Also other selection systems can be used.

Once the expression vector containing the DNA encoding the endoglucanase is prepared, it is introduced into an appropriate host cell by any of a variety of suitable means, including transformation as known in the art. After transformation, recipient cells are usually grown in an appropriate selective medium, which selects for the growth of transformed cells.

Suitable expression and production host systems are for example the production system developed for fungal hosts *Trichoderma* (EP 244 234), or *Aspergillus*, such as *A. oryzae* or *A. niger* (WO 97/08325 and WO 95/33386, U.S. Pat. No. 5,843,745, U.S. Pat. No. 5,770,418), or the production system developed for *Fusarium*, such as *F. oxysporum* (Malardier et al., 1989) or *Chrysosporium luckowense*. According to a preferred embodiment of the invention partially cellulase and/or hemicellulase and/or protease deficient host strains can be used. Suitable production systems developed for bacteria include a production system developed for *Bacillus*, for example *B. subtilis, B. licheniformis, B. amyloliquefaciens* or for *E. coli*, or for an actinomycete *Streptomyces*. Suitable production systems developed for yeasts are systems developed for *Saccharomyces, Shizosaccharomyces, Pichia pastoris* or *Hansenula*. Production systems in other microbes including consolidated fermentative microbes for bioethanol production or in mammalian cells or in plants are also possible.

Expression of the cloned gene sequence(s) results in the production of the desired protein, or in the production of a fragment of this protein. This expression can take place in a continuous manner in the transformed cells, or in a controlled manner.

To obtain the enzyme preparations of the invention, the hosts having the desired properties (that is, hosts capable of expressing economically feasible quantities of the endoglucanase proteins) are cultivated under suitable conditions, and the desired enzymes are preferably secreted from the hosts into the culture medium, and optionally recovered from said culture medium by methods known in the art. Preferably the host for such production is a filamentous fungus, such as *Trichoderma* or *Aspergillus*, and especially *T. reesei*.

As used in the present context the "enzyme preparation" refers to any enzyme product, which contains at least one of the novel endoglucanases described herein. Thus, such an enzyme preparation may be a spent culture medium or filtrate. Spent culture medium means the culture medium of the host comprising the produced enzymes. Preferably the host cells are separated from said medium after the production. If desired, such preparations may be lyophilized or the enzymatic activity otherwise concentrated and/or stabilized for storage. If required, a desired enzyme may be isolated and further purified in accordance with conventional methods, such as filtration, extraction, precipitation, chromatography, affinity chromatography, electrophoresis, or the like.

However, it is an advantage of the invention that the culture medium with or without host cells may be utilized as an enzyme preparation as such without further purification, because the endoglucanase proteins can be secreted into the culture medium, and they display activity in the ambient conditions of the spent culture medium. The enzyme preparations are very economical to provide and use, because isolation of a specific enzyme from the culture medium is unnecessary.

In addition to one or more endoglucanase proteins, the enzyme preparations may comprise one or more other enzymes, which may be for example other cellulases, amylases, lipases, proteases, hemicellulases, xylanases, pectinases and/or oxidases such as laccases, peroxidases and catalases. Alternatively, before, during or after the treatment with the endoglucanase protein another enzyme treatment may be carried out. The enzyme treatment may comprise, for example, one or more amylase treatments (e.g. for desizing of denim), one or more cellulase treatments and/or one or more peroxidase and/or laccase treatments. It depends on the application what other enzymes are included in the enzyme preparation or used in the enzyme treatment.

In addition to the endoglucanase protein, the enzyme preparation may contain additives, such as stabilizers, buffers, preservatives, surfactants and/or culture medium components. Preferred additives are such, which are commonly used in enzyme preparations intended for the application, where the enzyme preparation is used.

The enzyme preparations may be provided as a liquid or as a solid, for example, as a dried powder or granular, especially non-dusting granules, or a stabilized liquid. It is envisioned that the enzyme preparations can be further enriched to satisfy the requirements of a specific utility in various applications e.g. in the textile industry. A mixture of enzyme activities secreted by a host can be advantageous in a particular industrial application, for example in biofinishing and biostoning.

The endoglucanase proteins and the preparations thereof are useful e.g. in textile, feed and food, e.g. baking applications, in biomass hydrolysis, e.g. in bioethanol production, and in plant oil, detergent, and pulp and paper industry. They may be used for treating any cellulosic material, such as textile material, plants or material of plant origin used in food or animal feed, plant material for oil extraction, or wood-derived mechanical or chemical pulp or secondary fiber. They may also be added into detergents e.g. to improve fabric care properties by antipilling, antigreying, color clarification and softening, and to improve the textile cleaning effect, for instance soil removal. The detergent compositions further normally contain auxiliaries, such as surface active agents (anionic, non-ionic, cationic and ampholytic surfactants), builders and other optional ingredients such as antiredeposition and soil suspension agents, optical brighteners, bleaching agents, dyes and pigments and hydrolases.

In the present context "cellulosic material" refers to any material comprising cellulose or derivatives thereof as a significant component. The cellulosic material is contacted with an effective amount of the protein under suitable conditions, such as appropriate pH, and temperature, and the reaction is allowed to continue for a time sufficient for the enzymatic reaction to take place. The described Cel 2 endoglucanases are preferably used at a temperature range of about 20-60° C., and more preferably about 30-50° C. depending on the particular enzyme used. Useful temperatures can be ≤50° C., for example ≤45° C., or ≤40° C., or even ≤30° C. A suitable pH range is about 2-8, preferably about 3-6.5, and especially about 4-6. According to one specific embodiment the pH is about 4.5-5.5, or about 5.0-5.5. The described Cel5 endoglucanases are used at a temperature of about 30-70° C., preferably about 50-60° C., and at a pH range of about 2-7, preferably about 4-6, and especially about 5-6, except for the endoglucanase derived from *Fusarium*, which is preferably used in application at a pH range of about 4-10, more preferably 5-8, even more preferably 6-7, especially about 6.5, and a temperature of 50-60° C.

The endoglucanases are especially useful in the treatment of textile materials, such as fabrics and garments or yarn. The textile material may be manufactured of natural cellulose containing fibers or man-made cellulose containing fibers or mixtures thereof, or a blend of synthetic fibers and cellulose containing fibers. Preferably the cellulose containing material is cotton, especially denim. By "denim" is meant, in connection of this invention, denim fabric, usually denim garments, particularly jeans. Advantageously the denim is Indigo dyed denim. Denim can also be treated with derivatives of Indigo or with Indigo together with some other dye, for example Indigo-dyed denim with sulphur bottom.

The described endoglucanases are especially useful in textile industry preferably in biostoning and biofinishing.

Stone washing has three steps: desizing, abrasion and after-treatment. The first step, the desizing process is normally the first wet treatment of jeans and means removal of starch or other sizing agents usually applied to the warp yarns to prevent damage during the weaving process. Alpha-amylases are used to remove starch-based sizing agents for improved and uniform wet processing. After desizing the jeans are normally rinsed with water or passed directly to the abrasion step.

The second step, abrasion, can be performed with enzymes or pumice stones or both. In all cases mechanical action is needed to remove the dye, and the treatment is usually carried out in washing machines, like drum washers. The term "abraded" means the appearance of denim fabric, when it has been treated by cellulase enzymes or stones, or both. Synonymous expressions are "stone washed look" or "worn look". As a result of uneven dye removal there are contrasts between dyed areas and areas from which dye has been removed.

Abrasion is generally followed by the third step, after-treatment that includes washing and rinsing steps during which detergents, optical brighteners, bleaching agents or softeners may be used. After the enzymatic treatment the reaction should be stopped in order to prevent damage of the treated materials, for example by temperature and/or pH inactivation, the latter comprising a thorough rinsing and/or detergent wash-off. This ensures that the mechanical strength of the fiber is not further compromised by the continued presence of the enzyme.

As used in the present context the expression "biostoning" of fabric or garment means the use of enzymes in place of, or in addition to, pumice stones for the treatment of fabric or garment, especially denim.

As stated above, treatment with cellulase can completely replace treatment with pumice stones. However, cellulase treatment can also be combined with pumice stone treatment, when it is desired to produce a heavily abraded finish.

Further, the endoglucanases are useful in biofinishing of fabrics and garments. "Biofinishing" (also called depilling, defuzzing, dehairing or biopolishing) refers to the use of enzymes in a controlled hydrolysis of cellulosic fibers in order to modify the fabric or yarn surface in a manner that permanently prevents tendency for pilling, improves fabric handle like softness and smoothness, clears the surface structure by reducing fuzzing, which results in clarification of colors and may also improve the drapability, moisture absorbency and the dyeability of the fabric.

Additional uses include the use in detergent compositions to improve fabric care properties by antipilling, antigraying, color clarification and softening, and to improve textile-cleaning effect, for instance soil removal.

Enzymatic depilling can be carried out at any stage during textile wet processing, preferably after optional desizing and/or bleaching, and similar conditions as in biostoning can be used. Also textiles in garment form can be treated.

The liquor ratio (the ratio of the volume of liquid per weight of fabric) in both biostoning and biofinishing may range from about 3:1 to 20:1, preferably 5:1 to 10:1. The treatment time can range between 15 min to 90 min and preferably 30 min to 60 min. It should be emphasized that the enzyme dosage greatly depends on the type of the fabrics, machinery, process conditions (pH, temperature, liquor ratio, treatment time, denim load, process scale) and type of enzyme preparation and like. A person skilled in art is capable of defining suitable dosages and conditions.

The process of the invention for treating cellulosic material also encompasses hydrolysis of lignocellulosic material for e.g. bioethanol production. One example of use of consolidated bioprocessing (CBP) in hydrolysis of lignocellulosic material is described e.g. by van Zyl et al. in Adv Biochem Eng Biotechnol. 2007; 108:205-35.

The invention is further illustrated by the following non-limiting examples.

Example 1

Screening for Strains Expressing Low-Temperature Cellulolytic Activity

About 180 fungal strains in the Roal Oy culture collection were tested for their ability to produce low-temperature cellulolytic activity. The fungal strains were cultivated in a volume of 100 ml on a rotary shaker (200 rpm) at a temperature of 20° C. for 3-7 d. Several production media were tested containing Solka Floc cellulose as a carbon source. After the cultivation the cells and other solids were collected by centrifugation and the supernatant was recovered. If not used immediately, the preparation was stored in aliquots at −20° C.

For the estimation of the enzyme activity at lower temperatures, assays were performed of the shake flask cultivation preparation at 30° C. and 50° C. for 1 h. All shake flask supernatants were assayed for the following activities:

The endoglucanase (CMCase) activity:

This was assayed with 3% (w/v) carboxymethylcellulose (CMC) as the substrate in 50 mM citrate buffer essentially as described by Bailey and Nevalainen 1981; Haakana et al., 2004. Reducing sugars were measured with the DNS reagent. The assay was performed both at pH 5.0 and 7.0.

The endoglucanase (ECU) activity:

This was assayed with 1% (w/v) hydroxyethylcellulose (HEC) as the substrate in 50 mM citrate buffer essentially as described by Bailey and Nevalainen 1981. Reducing sugars were measured with the DNS reagent. The assay was performed both at pH 5.0 and 7.0.

Culture supernatant preparations of the strains were tested in a small scale biostoning application in an LP-2 Launder Ometer as follows. About 7.2 g of desized denim swatches (12×12 cm) were loaded with steel balls into 1.2 liter containers containing 100 ml Mc Ilvaine's buffer and 100 ml culture supernatant, and the Launder Ometer was run at 30° C. for 120 min. After alkaline and detergent wash, the fabric samples were rinsed carefully with warm water and air dried. The results were evaluated both visually and by measuring the colour as reflectance values (data not shown).

After preliminary screening, 13 strains (*Trichoderma* sp. RF6193, *Trichoderma gamsii* RF6208, *Hypocrea rufa/Trichoderma viride* RF6310, *Hypocrea atroviridis* RF6323, *Trichoderma harzianum* RF6482 and RF6541, *Trichoderma fertile* RF6601, *Hypocrea koningiopsis* RF6604, *Penicillium spinulosum* RF6286, *Penicillium griseofulvum* Dierckx RF6288, *Geomyces pannorum* RF6293 and RF6547, and *Fusarium cf. equiseti* RF6318) were chosen for additional application studies. For that purpose the strain RF6193 was cultivated in a volume of 200 ml on a rotary shaker (200 rpm) at a temperature of 20° C. for 7 d in a complex lactose-based cellulase-inducing medium (Joutsjoki et al. 1993) buffered with 5% $KH_2PO_4$. The strains RF6208, RF6310, RF6547, RF6601 and RF6604 were cultivated in a volume of 200 ml on a rotary shaker (200 rpm) at a temperature of 20° C. for 4-7 d in a medium, which contains g/liter: Solka Floc cellulose 6.0, wheat bran 4.0, xylan from birchwood 2.0, corn steep powder 1.0, soybean meal 1.0, locust bean gum 2.0, $CaCO_3$ 2.0, $(NH_4)_2HPO_4$ 1.5, $KH_2PO_4$ 0.5, $MgSO_4.H_2O$ 0.5, NaCl 0.5, trace element solution #1 0.5, trace element solution #2 0.5, paraffin oil 0.5; the pH was adjusted to 6.4. Trace element solution #1 (mg/liter): $MnSO_4$ 1.6, $ZnSO_4.H_2O$ 3.45, $CoCl_2.H_2O$ 2.0; Trace element solution #2 (mg/liter): $FeSO_4.H_2O$ 5.0. The strains RF6323, RF6482 and RF6541 were cultivated in a volume of 200 ml on a rotary shaker (200 rpm) at a temperature of 20° C. for 7 d in a medium, which contains g/liter: Solka Floc cellulose 10.0, corn steep powder 1.5, soybean meal 0.5, CaCO$_3$ 0.5, (NH$_4$)$_2$HPO$_4$ 1.5, KH$_2$PO$_4$ 2.0, MgSO$_4$.H$_2$O 0.5, NaCl 0.5, NH$_4$NO$_3$ 0.5, Tween-80 0.5, trace element solution #1 0.5, trace element solution #2 0.5, paraffin oil 0.5; the pH was adjusted to 6.4. Trace element solution #1 (mg/liter): MnSO$_4$ 1.6, ZnSO$_4$.H$_2$O 3.45, CoCl$_2$H$_2$O 2.0; Trace element solution #2 (mg/liter): FeSO$_4$.H$_2$O 5.0. The strains RF6288, RF6293 and RF6318 were cultivated in a volume of 200 ml on a rotary shaker (200 rpm) at a temperature of 20° C. for 4-6 d in a medium, which contains g/liter: Solka Floc cellulose 30.0, corn steep powder 9.0, soybean meal 1.5, CaCO$_3$ 1.5, (NH$_4$)$_2$HPO$_4$ 4.5, KH$_2$PO$_4$ 6.0, MgSO$_4$.H$_2$O 1.5, NaCl 0.5, NH$_4$NO$_3$ 1.5, Tween-80 0.5, trace element solution #1 0.5, trace element solution #2 0.5, paraffin oil 0.5; the pH was adjusted to 6.4. Trace element solution #1 (mg/liter): MnSO$_4$ 1.6, ZnSO$_4$.H$_2$O 3.45, CoCl$_2$.H$_2$O 2.0; Trace element solution #2 (mg/liter): FeSO$_4$.H$_2$O 5.0. The strain RF6286 was cultivated in a volume of 200 ml on a rotary shaker (200 rpm) at a temperature of 20° C. for 4-6 d in the medium, which contains g/liter: Solka Floc cellulose 18.0, wheat bran 12.0, xylan from birchwood 6.0, corn steep powder 3.0, soybean meal 3.0, locust bean gum 6.0, CaCO$_3$ 6.0, (NH$_4$)$_2$HPO$_4$ 4.5, KH$_2$PO$_4$ 1.5, MgSO$_4$.H$_2$O 1.5, NaCl 0.5, trace element solution #1 0.5, trace element solution #2 0.5, paraffin oil 0.5; the pH was adjusted to 6.4. Trace element solution #1 (mg/liter): MnSO$_4$ 1.6, ZnSO$_4$.H$_2$O 3.45, CoCl$_2$.H$_2$O 2.0; Trace element solution #2 (mg/liter): FeSO$_4$.H$_2$O 5.0.

Example 2

Cloning of Endoglucanase Genes from
Trichoderma sp. RF6193, Trichoderma gamsii
RF6208, Hypocrea rufa/Trichoderma viride
RF6310, Hypocrea atroviridis RF6323,
Trichoderma harzianum RF6482 and RF6541,
Trichoderma fertile RF6601, Hypocrea koningiopsis
RF6604, Penicillium spinulosum RF6286,
Penicillium griseofulvum Dierckx RF6288,
Geomyces pannorum RF6293 and RF6547, and
Fusarium cf. equiseti RF6318

Standard molecular biology methods were used in the isolation and enzyme treatments of DNA (plasmids, DNA fragments), in *E. coli* transformations, etc. The basic methods used are described in the standard molecular biology handbooks, e.g. Sambrook et al. (1989) and Sambrook and Russell (2001).

Genomic libraries of *Trichoderma* sp. RF6193, *Trichoderma gamsii* RF6208, *Hypocrea rufa/Trichoderma viride* RF6310, *Hypocrea atroviridis* RF6323, *Trichoderma harzianum* RF6482 and RF6541, *Trichoderma fertile* RF6601, *Hypocrea koningiopsis* RF6604 and *Penicillium griseofulvum* Dierckx RF6288 were made to Lambda FIX® II/Xho I Partial Fill-in Vector kit (Stratagene, USA) according to the instructions from the supplier. The chromosomal DNAs, isolated by the method of Raeder and Broda (1985), were partially digested with Sau3A. The digested DNAs were size-fractionated and the fragments of the chosen size (6-23 kb) were filled-in and ligated to the XhoI digested Lambda FIX® II vector arms. The ligation mixtures were packaged using Gigapack III Gold packaging extracts according to the manufacturer's instructions (Stratagene, USA).

Lambda DASH®II/BamHI vector (Stratagene, USA) was used in the construction of the genomic libraries for *Penicillium spinulosum* RF6286, *Geomyces pannorum* RF6293 and RF6547, and *Fusarium* cf. *equiseti* RF6318 according to the instructions from the supplier. The chromosomal DNAs, isolated by the method of Raeder and Broda (1985), were partially digested with Sau3A. he digested DNAs were size-fractionated and the fragments of the chosen size (5-20 kb) were ligated to the BamHI digested lambda vector arms. The ligation mixtures were packaged using Gigapack III Gold packaging extracts according to the manufacturer's instructions (Stratagene, USA).

The titers of the constructed genomic libraries are presented in Table 1.

TABLE 1

Titers of the constructed genomic libraries

| Strain | Titer of the genomic library pfu/ml (×10$^6$) | Titer of the amplified genomic library pfu/ml (×10$^8$) |
| --- | --- | --- |
| Trichoderma sp. RF6193 | 0.20 | 1.2 |
| Trichoderma gamsii RF6208 | 1.84 | 163.0 |
| Hypocrea rufa/ Trichoderma viride RF6310 | 0.08 | 18.0 |
| Hypocrea atroviridis RF6323 | 0.30 | 119.0 |
| Trichoderma harzianum RF6482 | 0.02 | 2.0 |
| Trichoderma harzianum RF6541 | 0.97 | 50.0 |
| Trichoderma fertile RF6601 | 2.30 | 120.0 |
| Hypocrea koningiopsis RF6604 | 1.10 | 110.0 |
| Penicillium spinulosum RF6286 | 1.10 | 4.4 |
| Penicillium griseofulvum Dierckx RF6288 | 0.07 | 2.3 |
| Geomyces pannorum RF6293 | 0.38 | 100.0 |
| Geomyces pannorum RF6547 | 0.15 | 5.5 |
| Fusarium cf. equiseti RF6318 | 0.46 | 60.0 |

Several different approaches were used to obtain the probes for screening the genomic libraries which were constructed as described above. First heterologous probes of *T. reesei* egl2/cel5A and egl3/cel12A were used to screen the genomic libraries of *Trichoderma gamsii* RF6208, *Hypocrea rufa/Trichoderma viride* RF6310, *Hypocrea atroviridis* RF6323, *Trichoderma harzianum* RF6482 and RF6541, and *Hypocrea koningiopsis* RF6604. DIG-labeled *T. reesei* egl2/cel5A probe was amplified using 5"-GAGCTCTGGGGTC-CGATT-3' (SEQ ID NO: 1) and 5"-CGATGCAGTAT-GCGCCCA-3' (SEQ ID NO: 2) primers in the PCR reaction containing 50 mM Tris-HCl, pH 9.0, 15 mM (NH$_4$)$_2$SO$_4$, 0.1% Triton X-100, 1.5 mM MgCl$_2$, 0.2 mM dNTPs (PCR DIG labelling mix, Roche), 2 µM each primer and 1-2 units of Dynazyme EXT DNA polymerase (Finnzymes, Finland) and ≈0.4 µg of the pALK433 plasmid DNA containing partial *T. reesei* egl2/cel5A gene fragment. The conditions for the PCR reactions were the following: 5 min initial denaturation at 95° C., followed by 30 cycles of 1 min at 95° C., 1 min annealing at 55° C. (±5° C. gradient), 2 min extension at 72° C. and a final extension at 72° C. for 10 min. *T. reesei* egl3/cel12A probe was amplified correspondingly by using primers 5'-ATGAAGTTCCTTCAAGTC-3' (SEQ ID NO: 3) and 5'-TTAGTTGATAGATGCGG-3' (SEQ ID NO: 4), and pALK1976 plasmid DNA template containing *T. reesei* egl3/cel12a gene fragment.

Homologous probes for screening of the genomic libraries of *Trichoderma* sp. RF6193 and *Trichoderma fertile* RF6601 were amplified by PCR using the corresponding genomic DNA as template in the reactions. First, several primers (degenerate oligos) were planned and tested in PCR reactions (Table 3, SEQ ID NO: 10-18). The heterologous primers were planned by aligning egl2/cel5A and egl3/cel12A gene sequences from *Trichoderma gamsii* RF6208, Hypocrea rufa/Trichoderma viride RF6310, and Trichoderma harzianum RF6482 which were cloned first phase in the project. The PCR reaction mixtures contained 50 mM Tris-HCl, pH 9.0, 15 mM $(NH_4)_2SO_4$, 0.1% Triton X-100, 15 mM $MgCl_2$, 0.2 mM dNTPs, 1 µM each primer and 1-2 units of Dynazyme EXT DNA polymerase (Finnzymes, Finland) and 0.5-1 µg of the genomic DNA. The conditions for the PCR reactions were the following: 5 min initial denaturation at 95° C., followed by 30 cycles of 1 min at 95° C., 1 min annealing at 45° C. (±5° C. gradient), 2 min extension at 72° C. and a final extension at 72° C. for 10 min.

The genomic libraries of Penicillium spinulosum RF6286, Geomyces pannorum RF6547, and Fusarium cf. equiseti RF6318 were screened with the probes which were amplified by PCR using degenerate primers and the corresponding genomic DNA as a template. The sequences of the heterologous primers based on the conserved endoglucanase sequences (Table 3, SEQ ID NO: 19-22). The conserved sequences were identified by aligning the previously published amino acid sequences of Talaromyces emersonii AAL33639, Thermoascus aurantiacus AAL88714, Aspergillus oryzae BAD72778, Aspergillus niger CAA11965, Emericella nidulans BAA82592, Chaetomium globosum EAQ92953, Humicola insolens Q12624, Aspergillus aculeatus BAA29030, Aspergillus terreus AAW68436, Aspergillus fumigatus XP_755286, Volvariella volvacea AAG59832, Aspergillus kawachii BAB62317, Macrophomina phaseolina AAB51451 and Humicola grosea var. thermoidea BAA12676. The PCR reaction mixtures contained 10 mM Tris-HCl, pH 8.8, 50 mM KCl, 0.1% Triton X-100, 1.5 mM $MgCl_2$, 0.1 mM dNTPs, 1 µM each primer and 1-2 units of Dynazyme II DNA polymerase (Finnzymes, Finland) and 0.5-1 µg of the genomic DNA. The conditions for the PCR reactions were the following: 5 min initial denaturation at 95° C., followed by 30 cycles of 1 min at 95° C., 30 s annealing at 52.5° C. (±7.5° C. gradient), 1 min extension at 72° C. and a final extension at 72° C. for 5 min.

A homologous probe for screening of the Penicillium griseofulvum Dierckx RF6288 genomic library was obtained by using sequences of homologous primers based on the amino acid sequences of peptides of the Penicillium griseofulvum Dierckx RF6288 CCE2 protein. The CCE2 protein was detected from the culture supernatant Penicillium griseofulvum Dierckx RF6288 strain by SDS-PAGE. For peptide mass fingerprinting and for determination of internal peptides, the CCE2 protein band was cut from the SDS-PAGE, and the protein was reduced with dithiothreitol and alkylated with iodoacetamide before digestion with trypsin. Electrospray ionization quadrupole time-of-flight tandem mass spectra for de novo sequencing were generated using a Q-TOF (Micromass) instrument.

The internal peptide sequences of the Penicillium griseofulvum Dierckx RF6288 CCE2 protein are shown in Table 2 (SEQ ID NO: 5-9). The internal peptides were further used for planning of the homologous primers presented in Table 3 (SEQ ID NO: 23-28). The probe was synthesised in the PCR reaction mixtures containing 10 mM Tris-HCl, pH 8.8, 50 mM KCl, 0.1% Triton X-100, 1.5 mM $MgCl_2$, 0.1 mM dNTPs, 1 µM each primer and 1-2 units of Dynazyme II DNA polymerase (Finnzymes, Finland) and 0.5-1 µg of the genomic DNA. The conditions for the PCR reactions were the following: 5 min initial denaturation at 95° C., followed by 30 cycles of 1 min at 95° C., 30 s annealing at 52.5° C. (±7.5° C. gradient), 1 min extension at 72° C. and a final extension at 72° C. for 5 min

TABLE 2

Internal peptide sequences determined from CCE2 protein of the Penicillium griseofulvum Dierckx RF6288

| Peptide | Sequence | SEQ ID NO. |
|---|---|---|
| Peptide 1 | V V A A T Q/K W L/I K/Q | 5 |
| Peptide 2 | L/I L/I T S T T D F A A F W K/Q | 6 |
| Peptide 3 | S G A Y A V L/I D P H N F G R | 7 |
| Peptide 4 | V P F A M E R | 8 |
| Peptide 5 | L/I G E F A G P F E G E N K | 9 |

I/L = leucine and isoleucine have the same molecular mass and cannot be distinguished in ESI-MS/MS analysis
Q/K = the molecular mass of glutamine and lysine differs only 0.036 Da and cannot be distinguished in ESI-MS/MS analysis The probe for screening of the Geomyces pannorum RF6293 genomic library was synthesised with the primers based on the amino acid sequences of the peptides of Penicillium griseofulvum Dierckx RF6288 CCE2 protein, as described above. The heterologous probe was synthesised in the PCR reaction with CCE2_1F and CCE2_3R primers (Tables 3 and 4) using Geomyces pannorum RF6289 genomic DNA as a template. The PCR mixtures contained 10 mM Tris-HCl, pH 8.8, 50 mM KCl, 0.1% Triton X-100, 1.5 mM $MgCl_2$, 0.1 mM dNTPs, 1 µM each primer and 1-2 units of Dynazyme II DNA polymerase (Finnzymes, Finland) and 0.5-1 µg of the genomic DNA. The conditions for the PCR reactions were the following: 5 min initial denaturation at 95° C., followed by 30 cycles of 1 min at 95° C., 30 s annealing at 52.5° C. (±7.5° C. gradient), 1 min extension at 72° C. and a final extension at 72° C. for 5 min.

TABLE 3

Degenerate oligonucleotides tested as PCR primers to amplify probes for screening of endoglucanase genes from Trichoderma sp. RF6193, Trichoderma fertile RF6601, Penicillium spinulosum RF6286, Geomyces pannorum RF6547 and RF6293, and Fusarium cf. equiseti RF6318 and Penicillium griseofulvum Dierckx RF6288

| Oligonucleotide | Length (bp) | Sequence[a] | SEQ ID NO. |
|---|---|---|---|
| Cel5_cons_A_1 | 20 | CCYGTYGGHTGGCARTAYYT (s) | 10 |
| Cel5_cons_A_2 | 20 | GGHCCTACWAAYGCYCARTT (s) | 11 |

TABLE 3-continued

Degenerate oligonucleotides tested as PCR primers to amplify probes for screening of endoglucanase genes from *Trichoderma* sp. RF6193, *Trichoderma fertile* RF6601, *Penicillium spinulosum* RF6286, *Geomyces pannorum* RF6547 and RF6293, and *Fusarium* cf. *equiseti* RF6318 and *Penicillium griseofulvum* Dierckx RF6288

| Oligonucleotide | Length (bp) | Sequence[a] | SEQ ID NO. |
|---|---|---|---|
| Cel5_cons_A_3 | 17 | GAYATHCAYAAYTAYGC (s)[e] | 12 |
| Cel5_cons_B_1 | 20 | GTRCCRGAGTTRTCNGARTC (as) | 13 |
| Cel5_cons_B_2 | 17 | SWRTCNARRTAYTTRTG (as) | 14 |
| Cel12_cons_A_1 | 20 | GGAGACTWYGARCTYATGAT (s)[e] | 15 |
| Cel12_cons_A_2 | 20 | GGNGAYTWYGARYTNATGAT (s) | 16 |
| Cel12_cons_B_1 | 20 | GSCTCRGTDCCRAAYTGGTA (as) | 17 |
| Cel12_cons_B_2 | 18 | YTCNGTNCCRAAYTGRTA (as) | 18 |
| Cel5_S1 | 17 | TTYGAYACNAAYAAYGA (s) | 19 |
| Cel5_S2 | 17 | ATGCAYCARTAYCTNGA (s) | 20 |
| Cel5_AS1 | 17 | TCNAGRTAYTGRTGCAT (as) | 21 |
| Cel5_AS2 | 24 | CCACCASGGSCCSGCSGCCCACCA (as) | 22 |
| CCE2_1F | 20 | GTNCCNTTYGCNATGGARCG (s, peptide 4) | 23 |
| CCE2_2F | 17 | GAYCCNCAYAAYTTYGG (s, peptide 3) | 24 |
| CCE2_3R | 17 | CCRAARTTRTGNGGRTC (as, peptide 3) | 25 |
| CCE2_4F | 20 | GAYTTYGCNGCNTTYTGGAA (s, peptide 2) | 26 |
| CCE2_5R | 20 | TTCCARAANGCNGCRAARTC (as, peptide 2) | 27 |
| CCE2_6R | 20 | TCRAASGGSCCSGCRAAYTC (as, peptide 5) | 28 |

[a] D = A or G or T,
H = A or C or T,
R = A or G,
S = C or G,
W = A or T,
N = A or G or T or C,
Y = T or C;
"s" in the parenthesis = sense strand,
"as" in the parenthesis = antisense strand.
"peptide" in the parenthesis = primer is based on the internal peptide described in Table 2.

DNA products having the expected sizes (calculated from the published endoglucanase sequences) were obtained from several reactions. The DNA fragments of the expected sizes were isolated from the most specific PCR reactions and they were cloned to pCR® 4-TOPO® vector (Invitrogen, USA). The inserts were characterized by sequencing and by performing Southern blot hybridizations to the genomic DNAs digested with several restriction enzymes. The PCR fragments, which were chosen to be used as probes for screening of the *Trichoderma* sp. RF6193, *Trichoderma fertile* RF6601, *Penicillium* spinulosum RF6286, *Geomyces pannorum* RF6547 and RF6293, *Fusarium* cf. *equiseti* RF6318 and *Penicillium griseofulvum* Dierckx RF6288 genomic libraries are presented in Table 4.

TABLE 4

Primers used in the PCR reactions and probes chosen for screening of the endoglucanase genes from *Trichoderma* sp. RF6193, *Trichoderma fertile* RF6601, *Penicillium spinulosum* RF6286, *Geomyces pannorum* RF6547 and RF6293, *Fusarium* cf. *equiseti* RF6318 genomic libraries and *Penicillium griseofulvum* Dierckx RF6288. The genomic template DNA and the name of the plasmid containing the probe fragment are shown.

| Gene | Forward primer | Reverse primer | Genomic DNA used as a template in PCR reaction | Fragment obtained (kb) | SEQ ID NO: | Insert in plasmid |
|---|---|---|---|---|---|---|
| RF6193_cel5A | Cel5_cons_A_1 | Cel5_cons_B_1 | RF6193 | 0.5 kb | 29 | pALK2319 |
| RF6193_cel5B | Cel5_cons_A_3 | Cel5_cons_B_1 | RF6193 | 0.5 kb | 30 | pALK2321 |
| RF6193_cel12A | Cel12_cons_A_1 | Cel12_cons_B_1 | RF6193 | 0.4 kb | 31 | pALK2323 |
| RF6601_cel5A | Cel5_cons_A_1 | Cel5_cons_B_1 | RF6601 | 0.4 kb | 32 | pALK2320 |
| RF6601_cel5B | Cel5_cons_A_3 | Cel5_cons_B_1 | RF6601 | 0.5 kb | 33 | pALK2322 |
| RF6601_cel12A | Cel12_cons_A_1 | Cel12_cons_B_1 | RF6601 | 0.5 kb | 34 | pALK2324 |
| RF6286_cel5A | Cel5_S2 | Cel5_AS2 | RF6286 | 0.3 kb | 35 | pALK2239 |
| RF6286_cel5B | Cel5_S2 | Cel5_AS2 | RF6286 | 0.3 kb | 36 | pALK2240 |
| RF6318_cel5A | Cel5_S2 | Cel5_AS2 | RF6318 | 0.3 kb | 37 | pALK2048 |
| RF6547_cel5A | Cel5_S2 | Cel5_AS2 | RF6547 | 0.3 kb | 38 | pALK2242 |
| RF6288_cel5A | CCE2_1F | CCE2_5R | RF6288 | 0.3 kb | 39 | pALK2029 |
| RF6293_cel5A | CCE2_1F | CCE2_3R | RF6289 | 0.2 kb | 40 | pALK2033 |

The deduced amino acid sequences from all these probes had homology to several published EGII/Cel5A and/or EGII/Cel12A sequences (BLAST program, version 2.2.9 at NCBI, National Center for Biotechnology Information; Altschul et al., 1990).

The inserts from the plasmids listed in Table 4 were labeled with digoxigenin according to the supplier's instructions (Roche, Germany). Correspondingly, *T. reesei* egl2/cel5A and egl3/cel12A gene fragments were digoxigenin-labeled to be used for screening of the genomic libraries of *Trichoderma gamsii* RF6208, *Hypocrea rufa/Trichoderma viride* RF6310, *Hypocrea atroviridis* RF6323, *Hypocrea viridescens* RF6331 and RF6603, *Trichoderma harzianum* RF6482 and RF6541, and *Hypocrea koningiopsis* RF6604. The amplified genomic libraries (1×10⁵-6×10⁵ plaques) were screened with labeled probe fragments. The hybridization temperature for the filters was 63-68° C. and the filters were washed 2×5 min at RT using 2×SSC-0.1% SDS followed by 2×15 min at 63-68° C. using 0.1-1×SSC-0.1% SDS. Several positive plaques were obtained from each of the hybridizations. From two to five strongly hybridizing plaques were purified from each screening. The phage DNAs were isolated and characterized by Southern blot hybridizations. The chosen restriction fragments hybridizing to the probe were subcloned to pBluescript II KS+ vector and the relevant regions of the clones were sequenced.

In total, 16 egl2/cel5 genes were cloned; one from *Hypocrea rufa/Trichoderma viride* RF6310, *Hypocrea atroviridis* RF6323, *Trichoderma harzianum* RF6482, *Hypocrea koningiopsis* RF6604, *Penicillium griseofulvum* Dierckx RF6288, *Geomyces pannorum* RF6293 and RF6547, and *Fusarium* cf. *equiseti* RF6318 strains, and two egl2/cel5 genes from *Trichoderma* sp. RF6193, *Trichoderma gamsii* RF6208, *Trichoderma fertile* RF6601 and *Penicillium spinulosum* RF6286 strains. In addition, five egl3/cel12 genes were cloned from *Trichoderma* sp. RF6193, *Trichoderma gamsii* RF6208, *Trichoderma harzianum* RF6482 and RF6541, and *Trichoderma fertile* RF6601 strains. Table 5 summarized the information on the probes used for the screening the genes, the phage clones from which the genes were isolated, the chosen restriction fragments containing the full-length genes with their promoter and terminator regions, the plasmid names, and the DSM deposit numbers for the *E. coli* strains carrying these plasmids.

TABLE 5

Probes used for cloning of endoglucanase genes, the phage clone and the subclones chosen, the plasmid number and the number of the deposit of the corresponding *E. coli* strain

| Gene | Probe used in screening | Phage clone | The fragment subcloned to pBluescript II KS+ | Plasmid no | E. coli deposit no |
|---|---|---|---|---|---|
| Tg_RF6208_cel5A | *T. reesei* cel5A | F15 | 6.7 kb SalI | pALK2121 | DSM 19418 |
| Tg_RF6208_cel5B | *T. reesei* cel5A | F11 | 4.7 kb XhoI | pALK2120 | DSM 18639 |
| Hr_RF6310_cel5A | *T. reesei* cel5A | F2 | 4.0 kb EcoRI | pALK2118 | DSM 18638 |
| Ha_RF6323_cel5A | *T. reesei* cel5A | F22 | 4.3 kb BamHI | pALK2123 | DSM 19963 |
| Th_RF6482_cel5A | *T. reesei* cel5A | F42 | 2.5 kb EcoRI | pALK2128 | DSM 18642 |
| Hk_RF6604_cel5A | *T. reesei* cel5A | F65A | 4.5 kb XhoI | pALK2158 | DSM 19419 |
| Ts_RF6193_cel5A | pALK2319 | F81 | 2.8 kb BamHI | pALK2330 | DSM 19894 |
| Ts_RF6193_cel5B | pALK2321 | F91A | 3.0 kb XbaI | pALK2331 | DSM 19895 |
| Tf_RF6601_cel5A | pALK2320 | F101A | 7.0 kb XbaI | pALK2359 | DSM 21129 |
| Tf_RF6601_cel5B | pALK2322 | F107 | 5.6 kb KpnI | pALK2366 | DSM 19898 |

TABLE 5-continued

Probes used for cloning of endoglucanase genes, the phage clone and the subclones chosen, the plasmid number and the number of the deposit of the corresponding E. coli strain

| Gene | Probe used in screening | Phage clone | The fragment subcloned to pBluescript II KS+ | Plasmid no | E. coli deposit no |
|---|---|---|---|---|---|
| Tg_RF6208_cel12A | T. reesei cel12A | F16 | 2.7 kb EcoRI | pALK2122 | DSM 18640 |
| Th_RF6482_cel12A | T. reesei cel12A | F46 | 2.5 kb XbaI | pALK2129 | DSM 18643 |
| Th_RF6541_cel12A | T. reesei cel12A | F80 | 2.2 kb HindIII | pALK2165 | DSM 19420 |
| Ts_RF6193_cel12A | pALK2323 | F128 | 4.0 kb XbaI | pALK2367 | DSM 19899 |
| Tf_RF6601_cel12A | pALK2324 | F113 | 4.0 kb XbaI | pALK2333 | DSM 19896 |
| Ps_RF6286_cel5A | pALK2239 | F125 | 3.0 kb PstI | pALK2248 | DSM 19960 |
| Ps_RF6286_cel5B | pALK2240 | F132 | 5.4 kb EcoRI | pALK2249 | DSM 19961 |
| Pg_RF6288_cel5A | pALK2029 | F61 | 4.4. kb XbaI | pALK2031 | DSM 18505 |
| Fe_RF6318_cel5A | pALK2048 | F114 | 5.0 kb EcoRI | pALK2225 | DSM 19172 |
| Gp_RF6293_cel5A | pALK2033 | F73 | 4.4 kb HindIII | pALK2044 | DSM 18914 |
| Gp_RF6547_cel5A | pALK2242 | F137 | 3.0 kb HindIII | pALK2250 | DSM 19962 |

The relevant information on the genes and the deduced protein sequences (SEQ ID NO: 41-82) are summarized in Table 6 and Table 7, respectively.

TABLE 6

Summary of the endoglucanase genes isolated from Trichoderma sp. RF6193, Trichoderma gamsii RF6208, Hypocrea rufa/Trichoderma viride RF6310, Hypocrea atroviridis RF6323, Trichoderma harzianum RF6482 and RF6541, Trichoderma fertile RF6601, Hypocrea koningiopsis RF6604, Penicillium spinulosum RF6286, Penicillium griseofulvum Dierckx RF6288, Geomyces pannorum RF6293 and RF6547, and Fusarium cf. equiseti RF6318

| Gene | Length with introns (bp)[a] | Coding Region (bp)[b] | No of introns | Lengths of introns (bp) | SEQ ID NO: |
|---|---|---|---|---|---|
| Tg_RF6208_cel5A | 1257 | 1254 | — | | 41 |
| Tg_RF6208_cel5B | 1269 | 1266 | — | | 43 |
| Hr_RF6310_cel5A | 1257 | 1254 | — | | 45 |
| Ha_RF6323_cel5A | 1269 | 1266 | — | | 47 |
| Th_RF6482_cel5A | 1278 | 1275 | — | | 49 |
| Hk_RF6604_cel5A | 1257 | 1254 | — | | 51 |
| Ts_RF6193_cel5A | 1260 | 1257 | — | | 53 |
| Ts_RF6193_cel5B | 1275 | 1272 | — | | 55 |
| Tf_RF6601_cel5A | 1311 | 1308 | — | | 57 |
| Tf_RF6601_cel5B | 1272 | 1269 | — | | 59 |
| Tg_RF6208_cel12A | 825 | 699 | 2 | 58, 65 | 61 |
| Th_RF6482_cel12A | 820 | 711 | 2 | 53, 53 | 63 |
| Th_RF6541_cel12A | 831 | 705 | 2 | 56, 67 | 65 |
| Ts_RF6193_cel12A | 834 | 705 | 2 | 58, 68 | 67 |
| Tf_RF6601_cel12A | 817 | 705 | 2 | 53, 56 | 69 |
| Ps_RF6286_cel5A | 1282 | 993 | 5 | 55, 62, 57, 64, 49 | 71 |
| Ps_RF6286_cel5B | 1444 | 1239 | 4 | 50, 47, 54, 51 | 73 |
| Pg_RF6288_cel5A | 1408 | 1200 | 4 | 55, 52, 50, 48 | 75 |
| Fe_RF6318_cel5A | 1193 | 1128 | 1 | 62 | 77 |
| Gp_RF6293_cel5A | 1095 | 999 | 2 | 48, 45 | 79 |
| Gp_RF6547_cel5A | 1284 | 1158 | 2 | 59, 54 | 81 |

[a]The STOP codon is included.
[b]The STOP codon is not included.

TABLE 7

Summary of the amino acid sequences deduced from the endoglucanase gene sequences from Trichoderma sp. RF6193, Trichoderma gamsii RF6208, Hypocrea rufa/Trichoderma viride RF6310, Hypocrea atroviridis RF6323, Trichoderma harzianum RF6482 and RF6541, Trichoderma fertile RF6601, Hypocrea koningiopsis RF6604, Penicillium spinulosum RF6286, Penicillium griseofulvum Dierckx RF6288, Geomyces pannorum RF6293 and RF6547, and Fusarium cf. equiseti RF6318

| Endoglucanase protein | No of aas | Length of ss NN[a] | CBD[b] | Predicted MW (Da), ss not incl[c] | Predicted pI (ss not incl) | SEQ ID NO: |
|---|---|---|---|---|---|---|
| Tg_RF6208_cel5A | 418 | 21 | T23 to I58 | 42142 | 4.88 | 42 |
| Tg_RF6208_cel5B | 422 | 21 | Q23 to V58 | 42200 | 4.43 | 44 |
| Hr_RF6310_cel5A | 418 | 21 | T23 to I58 | 42085 | 4.86 | 46 |

TABLE 7-continued

Summary of the amino acid sequences deduced from the endoglucanase gene sequences from *Trichoderma* sp. RF6193, *Trichoderma gamsii* RF6208, *Hypocrea rufa/Trichoderma viride* RF6310, *Hypocrea atroviridis* RF6323, *Trichoderma harzianum* RF6482 and RF6541, *Trichoderma fertile* RF6601, *Hypocrea koningiopsis* RF6604, *Penicillium spinulosum* RF6286, *Penicillium griseofulvum* Dierckx RF6288, *Geomyces pannorum* RF6293 and RF6547, and *Fusarium* cf. *equiseti* RF6318

| Endoglucanase protein | No of aas | Length of ss NN[a] | CBD[b] | Predicted MW (Da), ss not incl[c] | Predicted pI (ss not incl) | SEQ ID NO: |
|---|---|---|---|---|---|---|
| Ha_RF6323_cel5A | 422 | 21 | Q23 to I58 | 42424 | 4.29 | 48 |
| Th_RF6482_cel5A | 425 | 23 | Q23 to I60 | 42604 | 4.54 | 50 |
| Hk_RF6604_cel5A | 418 | 21 | T23 to V58 | 42133 | 4.85 | 52 |
| Ts_RF6193_cel5A | 419 | 21 | Q22 to I57 | 42261 | 5.08 | 54 |
| Ts_RF6193_cel5B | 424 | 23 | Q25 to I60 | 42440 | 4.54 | 56 |
| Tf_RF6601_cel5A | 436 | 17 | Q18 to I53 | 44368 | 5.29 | 58 |
| Tf_RF6601_cel5B | 423 | 21 | Q22 to V57 | 42237 | 4.59 | 60 |
| Tg_RF6208_cel12A | 233 | 16 | | 23374 | 5.49 | 62 |
| Th_RF6482_cel12A | 237 | 16 | | 25003 | 4.18 | 64 |
| Th_RF6541_cel12A | 235 | 16 | | 23810 | 5.39 | 66 |
| Ts_RF6193_cel12A | 235 | 16 | | 23793 | 6.06 | 68 |
| Tf_RF6601_cel12A | 235 | 16 | | 24826 | 4.12 | 70 |
| Ps_RF6286_cel5A | 331 | 17 | | 34762 | 3.92 | 72 |
| Ps_RF6286_cel5B | 414 | 16 | T379 to L414 | 42630 | 4.13 | 74 |
| Pg_RF6288_cel5A | 400 | 18 | G365 to L400 | 40921 | 4.64 | 76 |
| Fe_RF6318_cel5A | 376 | 16 | Q17 to Q52 | 40030 | 5.86 | 78 |
| Gp_RF6293_cel5A | 333 | 18 | | 34114 | 4.03 | 80 |
| Gp_RF6547_cel5A | 392 | 18 | Q19 to V54 | 39927 | 5.40 | 82 |

[a]The prediction on the signal sequence was made using the program SignalP V3.0 (Nielsen et al., 1997; Bendtsen et al., 2004); the NN value was obtained using neural networks.
[b]The cellulose-binding domain (CBD), the amino acids of the CBD region are indicated [M1(Met #1) included in numbering].
[c]The predicted signal sequence was not included. The prediction was made using the Compute pI/MW tool at ExPASy server (Gasteiger et al., 2003).

Comparison of the deduced EGII/Cel5 sequences from *Trichoderma/Hypocrea* to each other is presented in Table 8. Both the full-length amino acid sequences and the core proteins without the CBD region of the deduced EGII/Cel5 sequences from *Penicillium spinulosum* RF6286, *Penicillium griseofulvum* Dierckx RF6288, *Geomyces pannorum* RF6293 and RF6547, and *Fusarium* cf. *equiseti* RF6318 strains were compared to each other in Tables 9 and 10. Correspondingly, comparison of the deduced Cel12/EGIII sequences from *Trichoderma* sp. RF6193, *Trichoderma gamsii* RF6208, *Trichoderma harzianum* RF6482 and RF6541, and *Trichoderma fertile* RF6601 strains was performed (Table 11). A programme of Clone Manager (version 9) including the functions "Compare Two Sequences/Global/Compare sequences as amino acids/BLOSUM62 scoring matrix" was used for determining the degree of identity.

TABLE 8

Identity values (%) obtained from alignment of the deduced EGII/Cel5 amino acid sequences from *Trichoderma* sp. RF6193, *Trichoderma gamsii* RF6208, *Hypocrea rufa/Trichoderma viride* RF6310, *Hypocrea atroviridis* RF6323, *Trichoderma harzianum* RF6482, *Trichoderma fertile* RF6601 and *Hypocrea koningiopsis* RF6604. The full-length amino acid sequences including the signal sequences were aligned. A programme of Clone Manager 9 (Compare Two Sequences/Global/Compare sequences as amino acids/BLOSUM62 scoring matrix) was used for determining the degree of identity.

| | RF6208 Cel5A | RF6310 Cel5A | RF6604 Cel5A | RF6208 Cel5B | RF6323 Cel5A | RF6482 Cel5A | RF6193 Cel5A | RF6193 Cel5B | RF6601 Cel5A | RF6601 Cel5B |
|---|---|---|---|---|---|---|---|---|---|---|
| RF6208_Cel5A | 100 | 95 | 90 | 67 | 66 | 68 | 78 | 66 | 73 | 70 |
| RF6310_Cel5A | | 100 | 90 | 68 | 67 | 69 | 78 | 67 | 73 | 70 |
| RF6604_Cel5A | | | 100 | 71 | 69 | 70 | 78 | 69 | 72 | 72 |
| RF6208_Cel5B | | | | 100 | 95 | 83 | 70 | 81 | 67 | 80 |
| RF6323_Cel5A | | | | | 100 | 84 | 70 | 82 | 67 | 80 |
| RF6482_Cel5A | | | | | | 100 | 72 | 92 | 68 | 79 |
| RF6193_Cel5A | | | | | | | 100 | 72 | 84 | 74 |
| RF6193_Cel5B | | | | | | | | 100 | 68 | 79 |
| RF6601_Cel5A | | | | | | | | | 100 | 72 |
| RF6601_Cel5B | | | | | | | | | | 100 |

TABLE 9

Identity values (%) obtained from alignment of the deduced EGII/Cel5 amino acid sequences from *Penicillium spinulosum* RF6286, *Penicillium griseofulvum* Dierckx RF6288, *Geomyces pannorum* RF6293 and RF6547, and *Fusarium* cf. *equiseti* RF6318. The full-length amino acid sequences including the signal sequences were aligned. A programme of Clone Manager 9 (Compare Two Sequences/Global/Compare sequences as amino acids/BLOSUM62 scoring matrix) was used for determining the degree of identity.

|  | RF6286_Cel5A | RF6286_Cel5B | RF6288_Cel5A | RF6293_Cel5A | RF6318_Cel5A | RF6547_Cel5A |
|---|---|---|---|---|---|---|
| RF6286_Cel5A | 100 | 56 | 55 | 58 | 52 | 50 |
| RF6286_Cel5B |  | 100 | 71 | 49 | 39 | 42 |
| RF6288_Cel5A |  |  | 100 | 52 | 43 | 44 |
| RF6293_Cel5A |  |  |  | 100 | 46 | 48 |
| RF6318_Cel5A |  |  |  |  | 100 | 54 |
| RF6547_Cel5A2 |  |  |  |  |  | 100 |

TABLE 10

Identity values (%) obtained from alignment of the deduced EGII/Cel5 amino acid sequences from *Penicillium spinulosum* RF6286, *Penicillium griseofulvum* Dierckx RF6288, *Geomyces pannorum* RF6293 and RF6547, and *Fusarium* cf. *equiseti* RF6318. The core sequences excluding the signal sequence and linker-CBD regions were aligned. A programme of Clone Manager 9 (Compare Two Sequences/Global/Compare sequences as amino acids/BLOSUM62 scoring matrix) was used for determining the degree of identity.

|  | RF6286_Cel5A | RF6286_Cel5B | RF6288_Cel5A | RF6293_Cel5A | RF6318_Cel5A | RF6547_Cel5A |
|---|---|---|---|---|---|---|
| RF6286_Cel5A | 100 | 71 | 68 | 59 | 60 | 60 |
| RF6286_Cel5B |  | 100 | 77 | 63 | 55 | 61 |
| RF6288_Cel5A |  |  | 100 | 64 | 59 | 62 |
| RF6293_Cel5A |  |  |  | 100 | 54 | 58 |
| RF6318_Cel5A |  |  |  |  | 100 | 57 |
| RF6547_Cel5A |  |  |  |  |  | 100 |

TABLE 11

Identity values (%) obtained from alignment of the deduced Cel12/EGIII amino acid sequences from *Trichoderma* sp. RF6193, *Trichoderma gamsii* RF6208, *Trichoderma harzianum* RF6482 and RF6541, and *Trichoderma fertile* RF6601. The full-length amino acid sequences including the signal sequences were aligned. A programme of Clone Manager 9 (Compare Two Sequences/Global/Compare sequences as amino acids/BLOSUM62 scoring matrix) was used for determining the degree of identity.

|  | RF6208 Cel12A | RF6482 Cel12A | RF6541 Cel12A | RF6193 Cel12A | RF6601 Cel12A |
|---|---|---|---|---|---|
| RF6208_Cel12A | 100 | 55 | 76 | 73 | 57 |
| RF6482_Cel12A |  | 100 | 62 | 60 | 89 |
| RF6541_Cel12A |  |  | 100 | 89 | 63 |
| RF6193_Cel12A |  |  |  | 100 | 63 |
| RF6601_Cel12A |  |  |  |  | 100 |

Comparison of the deduced endoglucanase sequences from *Trichoderma* sp. RF6193, *Trichoderma gamsii* RF6208, *Hypocrea rufa/Trichoderma viride* RF6310, *Hypocrea atroviridis* RF6323, *Trichoderma harzianum* RF6482 and RF6541, *Trichoderma fertile* RF6601, *Hypocrea koningiopsis* RF6604, *Penicillium spinulosum* RF6286, *Penicillium griseofulvum* Dierckx RF6288, *Geomyces pannorum* RF6293 and RF6547, and *Fusarium* cf. *equiseti* RF6318 to the sequences found from the databases are shown in Table 12.

TABLE 12

The highest identity sequences to the deduced endoglucanase sequences of the *Trichoderma* sp. RF6193, *Trichoderma gamsii* RF6208, *Hypocrea rufa/Trichoderma viride* RF6310, *Hypocrea atroviridis* RF6323, *Trichoderma harzianum* RF6482 and RF6541, *Trichoderma fertile* RF6601, *Hypocrea koningiopsis* RF6604, *Penicillium spinulosum* RF6286, *Penicillium griseofulvum* Dierckx RF6288, *Geomyces pannorum* RF6293 and RF6547, and *Fusarium* cf. *equiseti* RF6318. The full-length amino acid sequences including the signal sequences were aligned. The database search was performed using BLAST (tblastn, nr/nt database), and Clone Manager 9 programme (Compare Two Sequences/Global/ Compare sequences as amino acids/BLOSUM62 scoring matrix) was used for determining the degree of identity.

| Organism and accession number | Identity (%) |
|---|---|
| Tg_RF6208_Cel5A | 100 |
| *Trichoderma viride*, AY343987 | 76 |
| *Trichoderma* sp., AY466436 | 76 |
| Tg_RF6208_Cel5B | 100 |
| *Trichoderma viride*, AY343987 | 69 |
| Hr_RF6310_Cel5A | 100 |
| *Trichoderma* sp., AY466436 | 77 |
| Ha_RF6323_Cel5A | 100 |
| *Trichoderma viride*, AY343987 | 69 |
| Th_RF6482_Cel5A | 100 |
| *Trichoderma viride*, AY343987 | 71 |
| Hk_RF6604_Cel5A | 100 |
| *Trichoderma viride*, AY343987 | 77 |
| *Trichoderma* sp., AY466436 | 77 |
| Ts_RF6193_Cel5A | 100 |
| *Trichoderma* sp., AY466436 | 93 |
| Ts_RF6193_Cel5B | 100 |
| *Trichoderma viride*, AY343987 | 71 |
| Tf_RF6601_Cel5A | 100 |
| *Trichoderma viride*, AY343987 | 81 |
| *Trichoderma* sp., AY466436 | 81 |
| Tf_RF6601_Cel5B | 100 |

TABLE 12-continued

The highest identity sequences to the deduced endoglucanase sequences of the *Trichoderma* sp. RF6193, *Trichoderma gamsii* RF6208, *Hypocrea rufa*/*Trichoderma viride* RF6310, *Hypocrea atroviridis* RF6323, *Trichoderma harzianum* RF6482 and RF6541, *Trichoderma fertile* RF6601, *Hypocrea koningiopsis* RF6604, *Penicillium spinulosum* RF6286, *Penicillium griseofulvum* Dierckx RF6288, *Geomyces pannorum* RF6293 and RF6547, and *Fusarium* cf. *equiseti* RF6318. The full-length amino acid sequences including the signal sequences were aligned. The database search was performed using BLAST (tblastn, nr/nt database), and Clone Manager 9 programme (Compare Two Sequences/Global/Compare sequences as amino acids/BLOSUM62 scoring matrix) was used for determining the degree of identity.

| Organism and accession number | Identity (%) |
|---|---|
| *Trichoderma viride*, AY343987 | 72 |
| Tg_RF6208_Cel12A | 100 |
| *Trichoderma viride*, AF435070 | 96 |
| Th_RF6482_Cel12A | 100 |
| *Hypocrea schweinitzii*, AF435068 | 59 |
| Th_RF6541_Cel12A | 100 |
| *Hypocrea schweinitzii*, AF435068 | 84 |
| Ts_RF6193_Cel12A | 100 |
| *Hypocrea schweinitzii*, AF435068 | 82 |
| Tf_RF6601_Cel12A | 100 |
| *Trichoderma reesei*, AB003694 | 61 |
| Ps_RF6286_Cel5A | 100 |
| *Aspergillus niger*, AF331518 | 69 |
| Ps_RF6286_Cel5B | 100 |
| *Neosartorya fischeri*, XM_001261833 | 71 |
| Pg_RF6288_Cel5A | 100 |
| *Aspergillus clavatus*, XM_001268255 | 71 |
| *Aspergillus fumigatus*, XM_745950 | 71 |
| Fe_RF6318_Cel5A | 100 |
| *Gibberella zeae*, XM_383971 | 90 |
| Gp_RF6293_Cel5A | 100 |
| *Thermoascus aurantiacus* var. *levisporus*, AY847014 | 60 |
| *Macrophomina phaseolina*, U14948 | 60 |
| Gp_RF6547_Cel5A | 100 |
| *Neurospora crassa*, XM_959066 | 61 |
| *Chaetomium globosum*, XM_001220408 | 61 |

TABLE 13

The highest identity of patent publication sequences to the deduced endoglucanase sequences of the *Trichoderma* sp. RF6193, *Trichoderma harzianum* RF6482 and RF6541, *Trichoderma fertile* RF6601, *Geomyces pannorum* RF6293, and *Fusarium* cf. *equiseti* RF6318. The full-length amino acid sequences including the signal sequences were aligned. The Chemical Abstracts Service (CAS) Registry System, DGEGE and Patended Protein Sequences NCBI database searches were performed using BLAST, and Clone Manager 9 programme (Compare Two Sequences/Global/ompare sequences as amino acids/LOSUM62 scoring matrix) was used for determining the degree of identity.

| Organism and accession number | Identity (%) |
|---|---|
| Gp_RF6293_Cel5A | 100 |
| JP2928265 B2, SEQ ID: 1 | 21 |
| Fe_RF6318_Cel5A | 100 |
| U.S. Pat. No. 7,314,974 B2, SEQ ID: 3197 | 57 |
| Th_RF6482_Cel12A | 100 |
| US20070026420 A1, SEQ ID: 9 | 59 |
| Th_RF6541_Cel12A | 100 |
| US20070026420 A1, SEQ ID: 8 | 82 |
| Ts_RF6193_Cel12A | 100 |
| US20070026420 A1, SEQ ID: 8 | 81 |
| Tf_RF6601_Cel12A | 100 |
| US20070026420 A1, SEQ ID: 9 | 62 |

Example 3

Production of Recombinant Endoglucanase Proteins in *Trichoderma reesei*

Expression plasmids were constructed for overexpression of recombinant endoglucanase proteins from *Trichoderma* sp. RF6193, *Trichoderma gamsii* RF6208, *Hypocrea rufa*/*Trichoderma viride* RF6310, *Hypocrea atroviridis* RF6323, *Trichoderma harzianum* RF6482 and RF6541, *Trichoderma fertile* RF6601, *Hypocrea koningiopsis* RF6604, *Penicillium spinulosum* RF6286, *Penicillium griseofulvum* Dierckx RF6288, *Geomyces pannorum* RF6293 and RF6547, and *Fusarium* cf. *equiseti* RF6318 in *Trichoderma reesei*. The expression plasmids constructed are listed in Table 14. The recombinant egl2/cel5 and egl3/cel12 genes, including their own signal sequences, were exactly fused to the *T. reesei* cbh1/cel7A promoter. The transcription termination was ensured by the *T. reesei* cbh1/cel7A terminator and the *A. nidulans* amdS marker gene was used for selection of the transformants as described in Paloheimo et al. (2003). The linear expression cassettes (FIG. 1) were isolated from the vector backbones after EcoRI or NotI digestion and were transformed into *T. reesei* A47 and/or A51 protoplasts (both strains have the genes encoding the four major cellulases CBHI/Cel7A, CBHII/Cel6A, EGI/Cel7B and EGII/Cel5A deleted). The transformations were performed as in Penttilä et al. (1987) with the modifications described in Karhunen et al. (1993), selecting with acetamide as a sole nitrogen source (amdS marker gene). The transformants were purified on selection plates through single conidia prior to sporulating them on PD.

TABLE 14

Expression cassettes constructed to overproduce endoglucanase proteins from *Trichoderma* sp. RF6193, *Trichoderma gamsii* RF6208, *Hypocrea rufa*/*Trichoderma viride* RF6310, *Hypocrea atroviridis* RF6323, *Trichoderma harzianum* RF6482 and RF6541, *Trichoderma fertile* RF6601, *Hypocrea koningiopsis* RF6604, *Penicillium spinulosum* RF6286, *Penicillium griseofulvum* Dierckx RF6288, *Geomyces pannorum* RF6293 and RF6547, and *Fusarium* cf. *equiseti* RF6318 in *Trichoderma reesei*. The overall structure of the expression cassettes was as described in FIG. 1. The cloned egl2/cel5 and egl3/cel12 genes were exactly fused to the *T. reesei* cbh1/cel7A promoter.

| Endoglucanase protein | Expression plasmid | Expression cassette[a] | Terminator[b] |
|---|---|---|---|
| Tg_RF6208_cel5A | pALK2302 | 9.1 kb EcoRI | 451 bp (PvuII) |
| Tg_RF6208_cel5B | pALK2144 | 9.3 kb EcoRI | 614 bp (XbaI) |
| Hr_RF6310_cel5A | pALK2142 | 9.1 kb EcoRI | 504 bp (PvuII) |
| Ha_RF6323_cel5A | pALK2146 | 8.8 kb EcoRI | 216 bp (BamHI) |
| Th_RF6482_cel5A | pALK2138 | 8.9 kb EcoRI | 263 bp (SpeI) |
| Hk_RF6604_cel5A | pALK2318 | 8.9 kb EcoRI | 275 bp (XbaI) |
| Ts_RF6193_cel5A | pALK2361 | 8.8 kb EcoRI | 123 bp (HindIII) |
| Ts_RF6193_cel5B | pALK2363 | 9.3 kb NotI | 633 bp (XbaI) |
| Tf_RF6601_cel5A | pALK2365 | 9.2 kb EcoRI | 502 bp (HindIII) |
| Tf_RF6601_cel5B | pALK2369 | 8.7 kb NotI | 47 bp (ClaI) |
| Tg_RF6208_cel12A | pALK2148 | 8.6 kb NotI | 390 bp (NruI) |
| Th_RF6482_cel12A | pALK2140 | 8.7 kb EcoRI | 480 bp (SpeI) |
| Th_RF6541_cel12A | pALK2314 | 8.3 kb EcoRI | 90 bp (SpeI) |
| Ts_RF6193_cel12A | pALK2376 | 8.3 kb EcoRI | 123 bp (HindIII) |
| Tf_RF6601_cel12A | pALK2371 | 8.2 kb EcoRI | 43 bp (SapI) |
| Ps_RF6286_cel5A | pALK2455 | 8.6 kb NotI | 187 bp (StuI) |
| Ps_RF6286_cel5B | pALK2458 | 9.2 kb NotI | 409 bp (BamHI) |
| Pg_RF6288_cel5A | pALK2037 | 8.9 kb NotI | 145 bp (XhoI) |
| Fe_RF6318_cel5A | pALK2233 | 9.0 kb NotI | 409 bp (SapI) |

TABLE 14-continued

Expression cassettes constructed to overproduce endoglucanase proteins from *Trichoderma* sp. RF6193, *Trichoderma gamsii* RF6208, *Hypocrea rufa/Trichoderma viride* RF6310, *Hypocrea atroviridis* RF6323, *Trichoderma harzianum* RF6482 and RF6541, *Trichoderma fertile* RF6601, *Hypocrea koningiopsis* RF6604, *Penicillium spinulosum* RF6286, *Penicillium griseofulvum* Dierckx RF6288, *Geomyces pannorum* RF6293 and RF6547, and *Fusarium* cf. *equiseti* RF6318 in *Trichoderma reesei*. The overall structure of the expression cassettes was as described in FIG. 1. The cloned egl2/cel5 and egl3/cel12 genes were exactly fused to the *T. reesei* cbh1/cel7A promoter.

| Endoglucanase protein | Expression plasmid | Expression cassette[a] | Terminator[b] |
|---|---|---|---|
| Gp_RF6293_cel5A | pALK2212 | 9.0 kb NotI | 539 bp (PstI) |
| Gp_RF6547_cel5A | pALK2461 | 8.9 kb NotI | 182 bp (EcoRV) |

[a] The expression cassette for *T. reesei* transformation was isolated from the vector backbone by using EcoRI or NotI digestion.
[b] The number of the nucleotides after the STOP codon of the cloned recombinant gene that was included in the expression cassette. The restriction site at the 3'-end of the genomic gene fragment that was used in the construction of the expression cassette is indicated in parenthesis.

The endoglucanase production of the transformants was analysed from the culture supernatants of the shake flask cultivations (50 ml). The transformants were grown for 7 days in a complex lactose-based cellulase-inducing medium (Joutsjoki et al. 1993) buffered with 5% $KH_2PO_4$. The endoglucanase activity was assayed with 3% (w/v) carboxymethylcellulose (CMC) as the substrate in 50 mM citrate buffer according to Bailey and Nevalainen 1981 and Haakana et al., 2004, or alternatively, using 1% (w/v) hydroxyethylcellulose (HEC) substrate as described by Bailey and Nevalainen 1981. The genotypes of the chosen transformants were confirmed by using Southern blots in which several genomic digests were included and the respective expression cassette was used as a probe. Heterologous production of recombinant endoglunase proteins was analyzed by SDS-PAGE with subsequent Coomassive staining.

Figure 2:
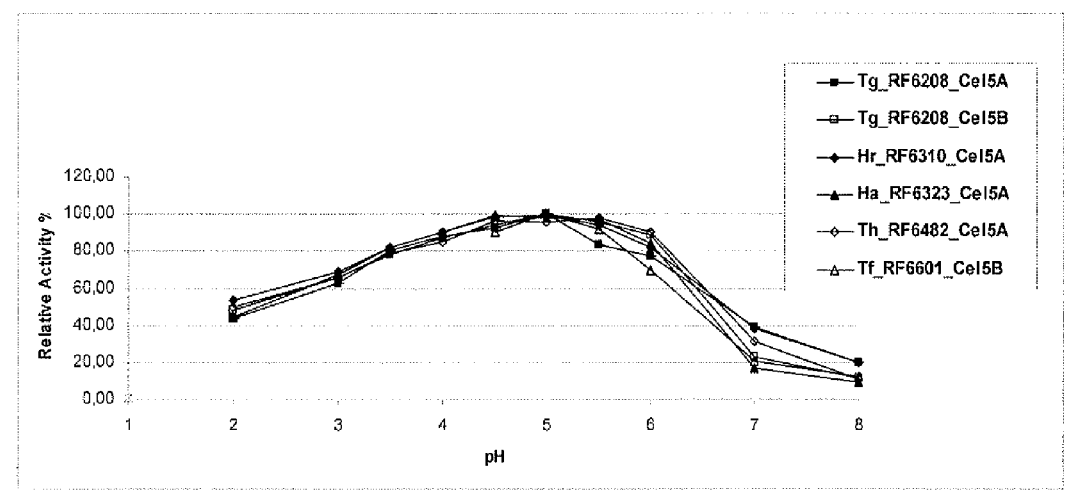
FIG. 2 A) shows pH optima of recombinant Cel5A/EGII protein preparations from *Trichoderma* or *Hypocrea*, B) shows pH optima of recombinant Cell 2A/EGIII protein preparations from *Trichoderma*, and C) shows pH optima of recombinant Cel5A/EGII protein preparations from fungi other than *Trichoderma*, D) shows thermal stability of recombinant Cel5A/EGII protein preparations from *Trichoderma* or *Hypocrea*, E) shows thermal stability of recombinant Cell 2A/EGIII protein preparations from *Trichoderma*, and F) shows thermal stability of recombinant EGII/Cel5 protein preparations from fungi other than *Trichoderma*.
Figure 2:
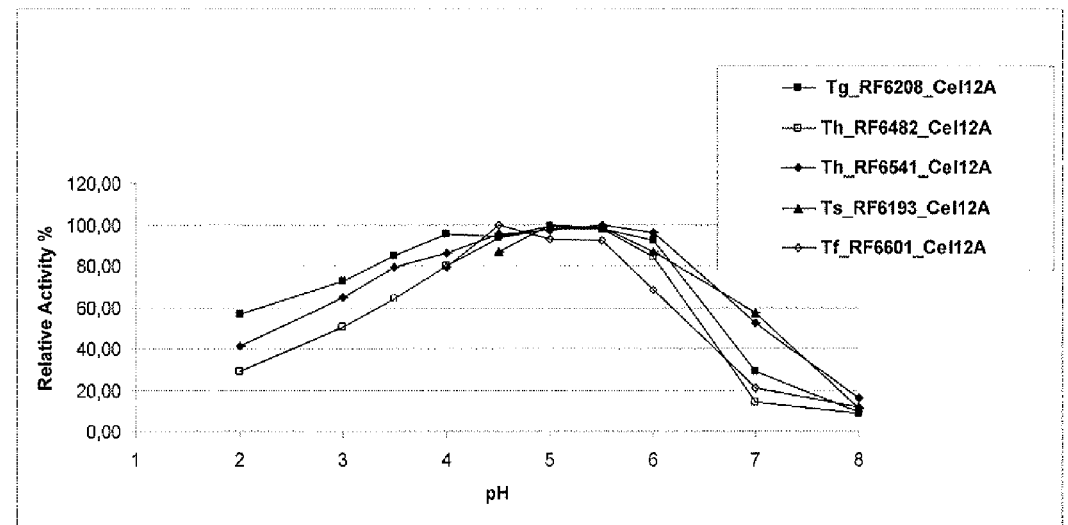
Figure 2:
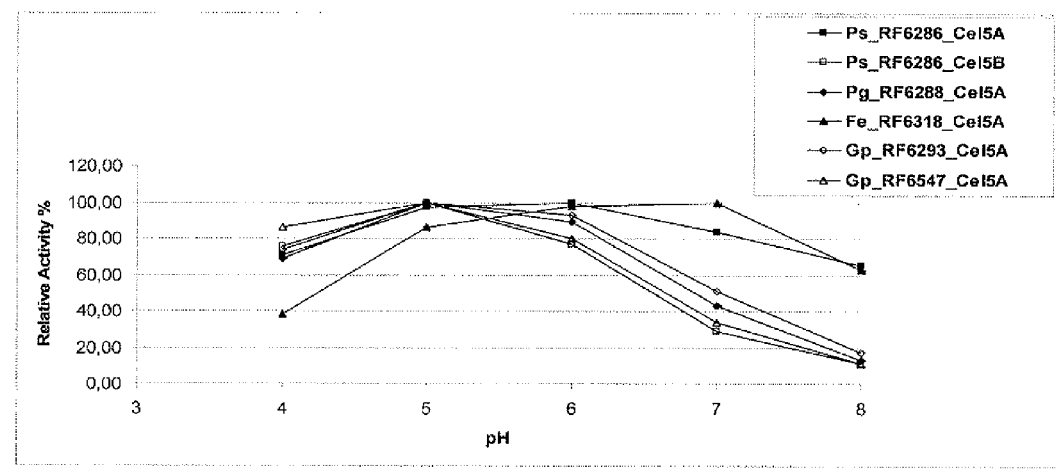
Figure 2:
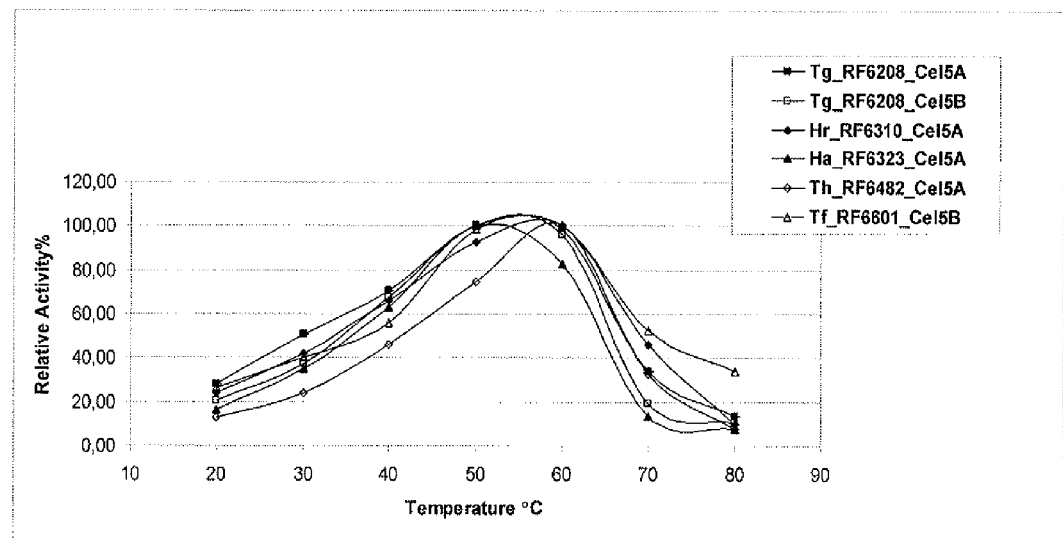
Figure 2:
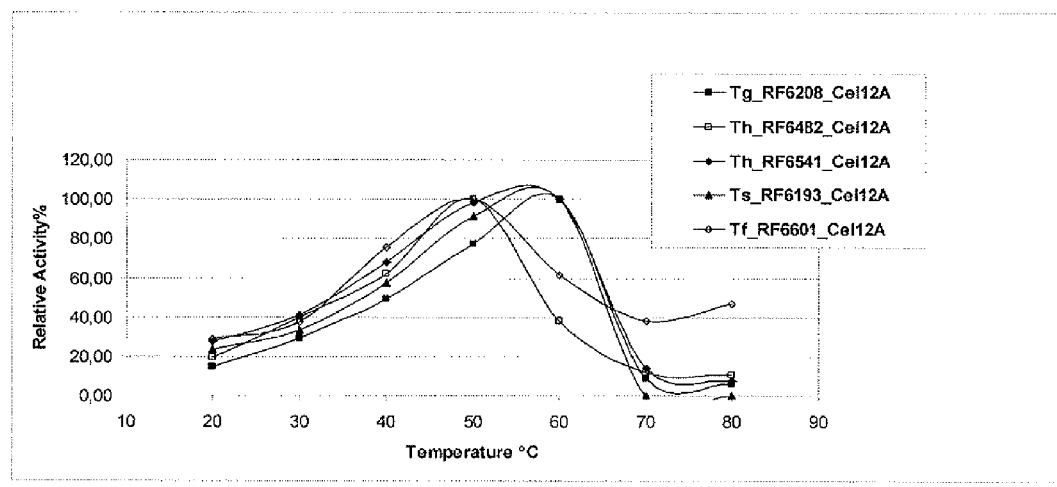
Figure 2:
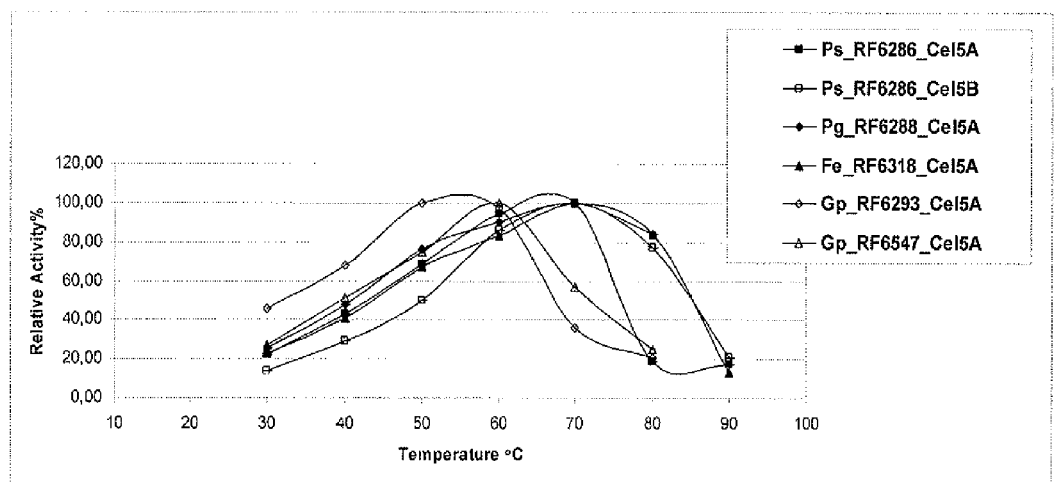

The recombinant endoglucanase enzyme preparations were characterized in terms of pH optimum and thermal stability. The pH optima of the overproduced endoglucanase proteins were determined in universal McIlvaine buffer within a pH range of 2.0-8.0 using 3% (w/v) carboxymethylcellulose (CMC) as substrate (FIG. 2 A-C). Thermal stability of the recombinant endoglucanase proteins was determined by measuring the CMCase activity in universal McIlvaine buffer at the optimum pH with reaction time of 1 h (FIG. 2D-F).

The chosen endoglucanase producing transformants were cultivated in lab bioreactors at 28° C. in the medium indicated above for 3-4 days with pH control 4.4±0.2 ($NH_3/H_3PO_4$) to obtain material for the application tests. The supernatants were recovered by centrifugation and filtering through Seitz-K 150 and EK filters (Pall Seitz-Schenk Filtersystems GmbH, Bad Kreuznach, Germany).

Example 4

Performance of Recombinant Cel12A Proteins in Denim Treatment at Different Temperatures Recombinant Cel12A proteins produced as described in Example 3 using *Trichoderma* as host were tested for their ability in biostoning of denim at different temperatures to create an abraded look similar to that provided by pumice stones. Commercial cellulase ECOSTONE® L900 (Roal Oy, Finland), which is an Cel5 enriched *Trichoderma reesei* cellulase preparation and Cel5 cellulase IndiAge® Super L (Genencor International), which is an Cel12 preparation, were used for comparison.

One pair of jeans made of Indigo dyed denim twill obtained from an English supplier was used as main test material after desizing with ECOSTONE® A200 alpha-amylase and 2 pairs of desized Apache jeans (Labels Fashion Limited, U.K.) as filler material. The cellulase treatments were performed with Electrolux's Wascator FOM 71 CLS washer extractor under conditions described in Table 15.

TABLE 15

The test conditions/process parameters used in cellulase treatments

| Process parameter | |
|---|---|
| Denim load | 1.6 kg |
| Water | 17 liter |
| Buffer/pH control (pH 5/6) | pH 5 adjusted with acetic acid pH 6 with $Na_2HPO_4\ H_2O$ and Citric acid |
| Time | 55 min |
| Temperature | 30, 40, 50 or 60° C. |
| Cellulase dosage | According to Table 16 |

Acid enzymes were dosed as endoglucanase activity (ECU), except IndiAge® Super L having an optimal pH range of 5.5-6.5 based on the manufacturer's information, as neutral cellulase activity units (NCU) per the weight of the fabric. Neutral cellulase activity was measured as the release of reducing sugars from carboxymethyl-cellulose (3% CMC) at 50° C. in 50 mM Hepes buffer pH 7.0 (Haakana et al. 2004). The endoglucanase (ECU activity) was measured at pH 4.8 with 1% (w/v) hydroxyethylcellulose (HEC) as described in Example 1. Dosing of IndiAge® Super L corresponds to 1.6-2.4% enzyme on the weight of the garment, the recommended dosage for the enzyme is 0.5-3% based on the manufacturer's information. The cellulase enzyme was inactivated after draining by raising the pH above 11 by adding 4.2 g of NaOH (10 min, 40° C.) and rinsing three times. The jeans were dried in a tumbler.

The biostoning effect/abrasion level of the main test material was evaluated by measuring the colour as reflectance values with Minolta CM 2500 spectrophotometer using L*a*b*colour space coordinates (illuminant D65/2°). The colour from the face side and the reverse side of denim was measured after desizing (i.e. before cellulase treatment) and after the cellulase treatment. Each measurement on the face side of the denim was the average of approximate 40 measurements. The results are shown in Table 16 and FIGS. 3-5.

One of the Cel45 enzyme preparations, Th_6482_Cel12, had already been tested earlier at different temperatures using ECOSTONE® L900 for comparison. The test system for biostoning was similar to that described above, except that two pieces (legs) of Atlanta and Nostalgy denim from Ukos Sport (Belgium) were used in addition to one pair of jeans made of Indigo dyed denim twill obtained from an English supplier (total 1.1 kg). In addition, the effect of the cellulase treatment was evaluated as described above, except that the final results shown in table 17, which are based on the average measurements of three different denims

TABLE 16

Colour measurements of the face side of denim treated with recombinant Cel12 preparations at different temperatures. Treatment with commercial enzyme preparations was used for comparison. L* indicates the lightness.

| Enzyme | Activity/ g garment | Conditions | Before cellulase treatment L* | After cellulase treatment L* | Increase of L* |
|---|---|---|---|---|---|
| Jeans batch 03/08 | | | | | |
| Th_RF6541_Cel12A | 75 ECU/g | 60° C., pH 5 | 16.76 | 20.02 | 3.26 |
| Th_RF6541_Cel12A | 75 ECU/g | 50° C., pH 5 | 16.96 | 21.83 | 4.87 |
| Th_RF6541_Cel12A | 75 ECU/g | 40° C., pH 5 | 16.86 | 20.8 | 3.94 |
| Th_RF6541_Cel12A | 75 ECU/g | 30° C., pH 5 | 16.85 | 19.6 | 2.75 |
| Ts_6193_Cel12A | 150 ECU/g | 60° C., pH 5 | 16.79 | 19.16 | 2.37 |
| Ts_6193_Cel12A | 150 ECU/g | 50° C., pH 5 | 16.83 | 21.52 | 4.69 |
| Ts_6193_Cel12A | 150 ECU/g | 40° C., pH 5 | 16.85 | 22.99 | 6.14 |
| Ts_6193_Cel12A | 150 ECU/g | 30° C., pH 5 | 16.91 | 22.28 | 5.37 |
| Th_6482_Cel12A | 375 ECU/g | 50° C., pH 5 | 16.5 | 23.42 | 6.92 |
| Th_6482_Cel12A | 375 ECU/g | 30° C., pH 5 | 16.42 | 20.8 | 4.38 |
| ECOSTONE ® L900 | 750 ECU/g | 50° C., pH 5 | 17.09 | 21.94 | 4.85 |
| ECOSTONE ® L900 | 750 ECU/g | 40° C., pH 5 | 16.69 | 20.46 | 3.77 |
| IndiAge ® Super L | 500 NCU/g | 30° C., pH 6 | 16.88 | 20.25 | 3.37 |
| IndiAge ® Super L | 750 NCU/g | 40° C., pH 6 | 16.77 | 21.65 | 4.88 |
| IndiAge ® Super L | 750 NCU/g | 30° C., pH 6 | 16.71 | 20.83 | 4.12 |
| Jeans batch 06/08 | | | | | |
| Tf_RF6601_Cel12A | 250 ECU/g | 60° C., pH 5 | 16.85 | 19.97 | 3.12 |
| Tf_RF6601_Cel12A | 250 ECU/g | 50° C., pH 5 | 16.84 | 20.94 | 4.10 |
| Tf_RF6601_Cel12A | 250 ECU/g | 40° C., pH 5 | 16.97 | 20.58 | 3.61 |
| Tf_RF6601_Cel12A | 250 ECU/g | 30° C., pH 5 | 16.94 | 20.06 | 3.12 |
| ECOSTONE ® L900 | 750 ECU/g | 40° C., pH 5 | 16.74 | 21.67 | 4.93 |

TABLE 17

Temperature profiles of Th_6482_Cel12A and ECOSTONE ® L900 in denim treatments (55 min, pH 5)

| Enzyme | Temperature (° C.) | Relative increase of L* (%) |
|---|---|---|
| Th_6482_Cel12A | 60 | 94 |
| | 50 | 100 |
| | 40 | 85 |
| | 30 | 88 |
| ECOSTONE ® L900 | 60 | 100 |
| | 50 | 76 |
| | 40 | 61 |
| | 30 | 58 |

Figure 3:
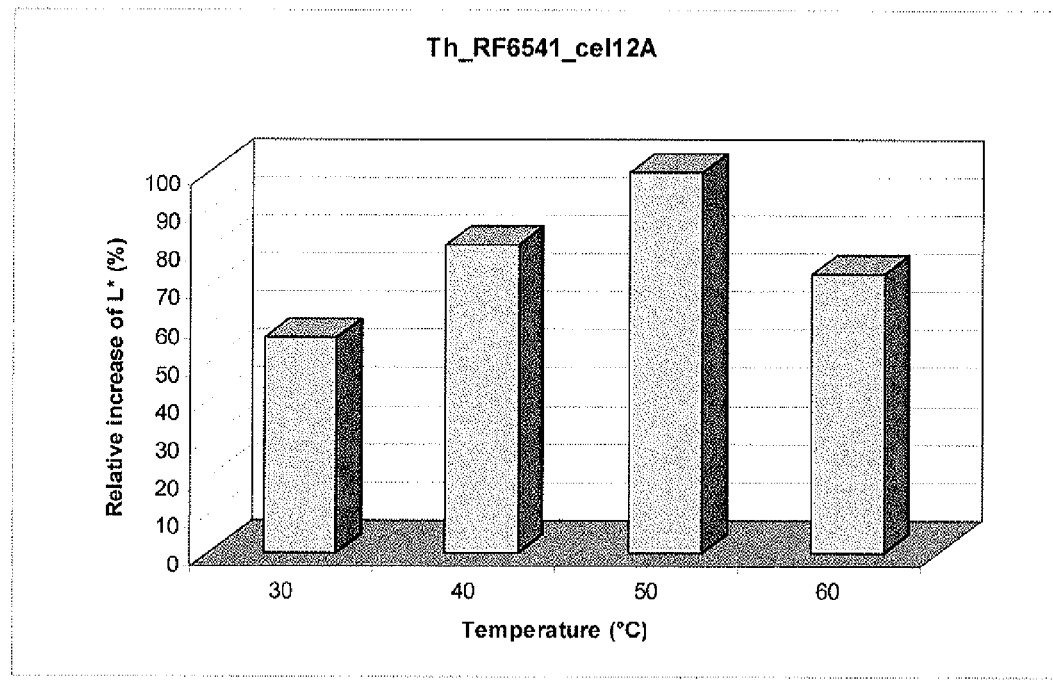
FIGS. 3-5 show temperature profiles of recombinant Cell 2A/EGIII protein preparations from *Trichoderma* in denim treatment.
Figure 4:
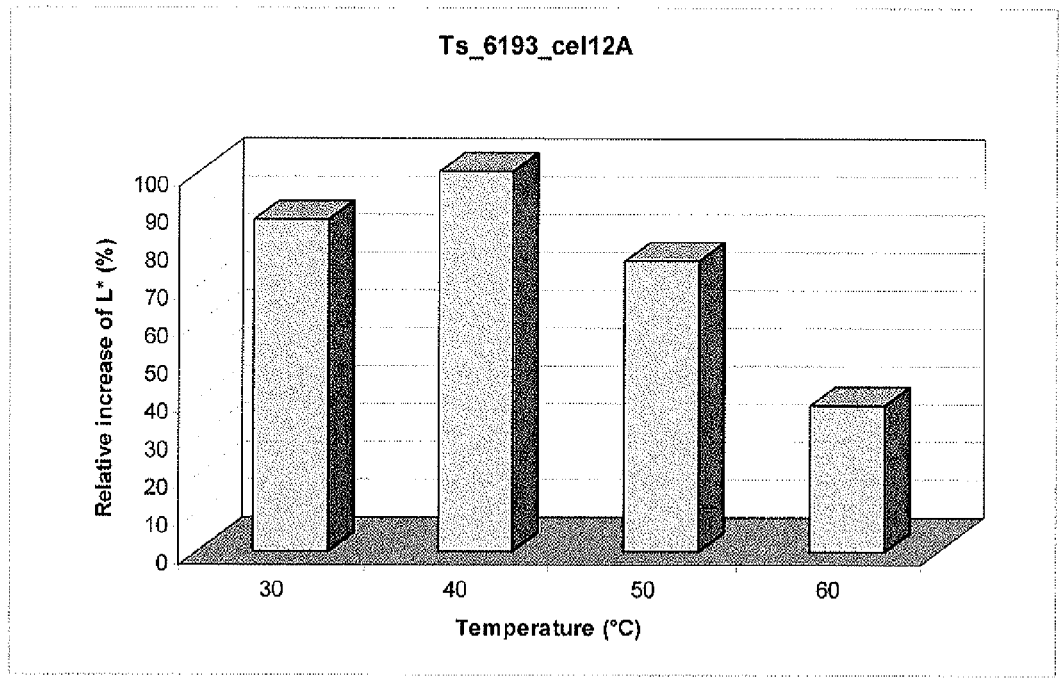
Figure 5:
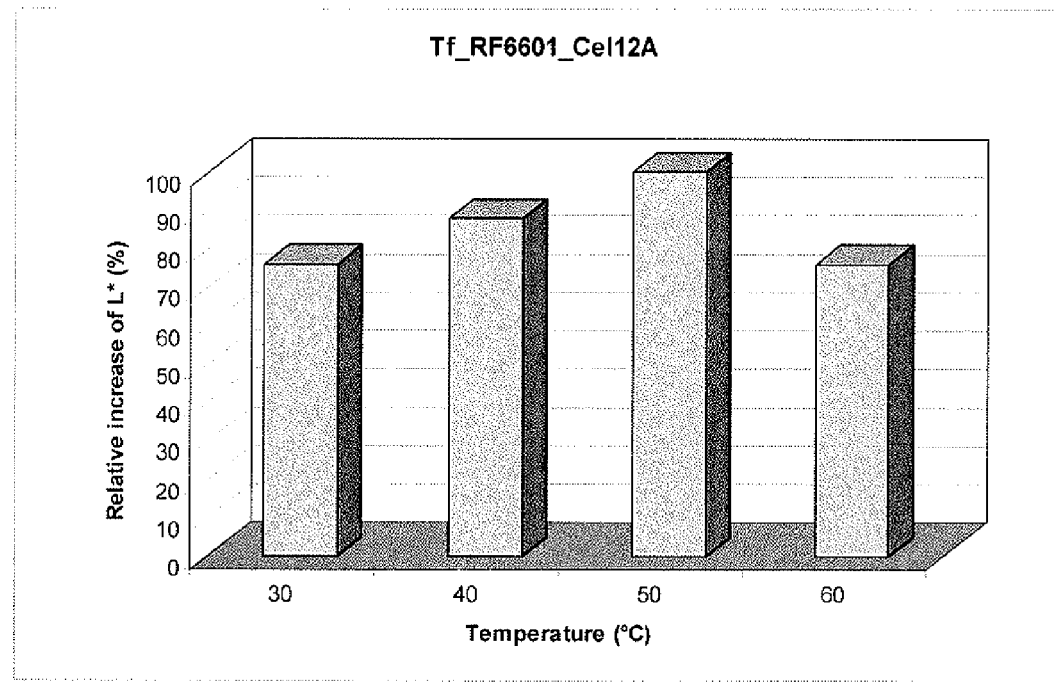

The results in Tables 16 and 17, and FIG. 3-5, show that with the recombinant Cel12 enzymes a biostoning effect similar to or even better than with the commercial denim enzymes was obtained. Th_RF6541_Cel12A shows optimal performance at 50° C., The optimal range for Ts_6193_cel12A is 30-40° C. and for Th_6601_cel12A 40-50° C. Th_6482_Cel12A performs well at a broad range from 30° C. to 60° C., (optimum 50° C.). All of the recombinant Cel12 enzymes had a lower temperature profile than the commercial ECOSTONE® L900 having optimal performance at 60° C.

Ts_6193_cel12A had a better performance relation 30° C./40° C. (87%) compared to IndiAge® Super L (84%), which contrary to the other cellulases tested here is a cellulase having an optimal pH range of 5.5-6.5 and optimal temperature range of 40-45° C. according to the manufacturer's product information.

Example 5

Performance of Fe_6318_Cel5A Protein in Denim Treatment at Different pH

Recombinant protein Fe_6318_cel5A protein produced using *Trichoderma* as host as described in Example 3 was tested for its ability in biostoning of denim at different pH to create an abraded look similar to that provided by pumice stones.

The denim (Jeans batch 03/2008) and test system for biostoning were as in Example 4, except that the temperature was 50° C. and pH 5-7 (adjusted with buffer). Also the effect of the cellulase treatment was evaluated as in Example 4.

Figure 6:
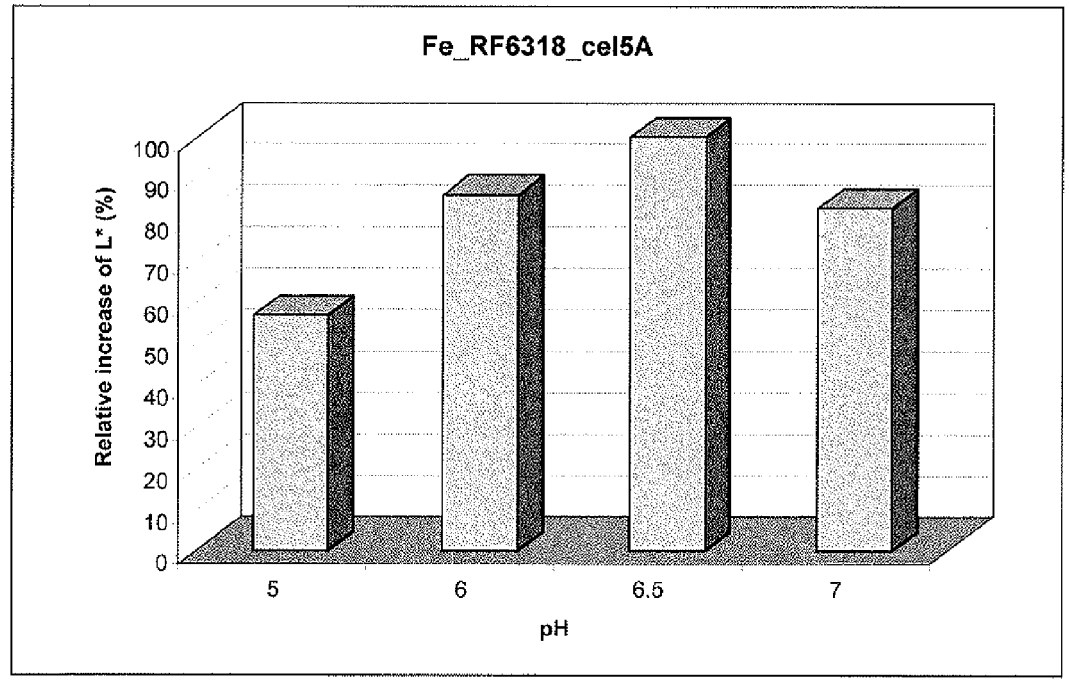
FIG. 6 shows the pH profile of a recombinant Cel5A/EGII protein preparation from *Fusarium* in denim treatment.
Figure 7:
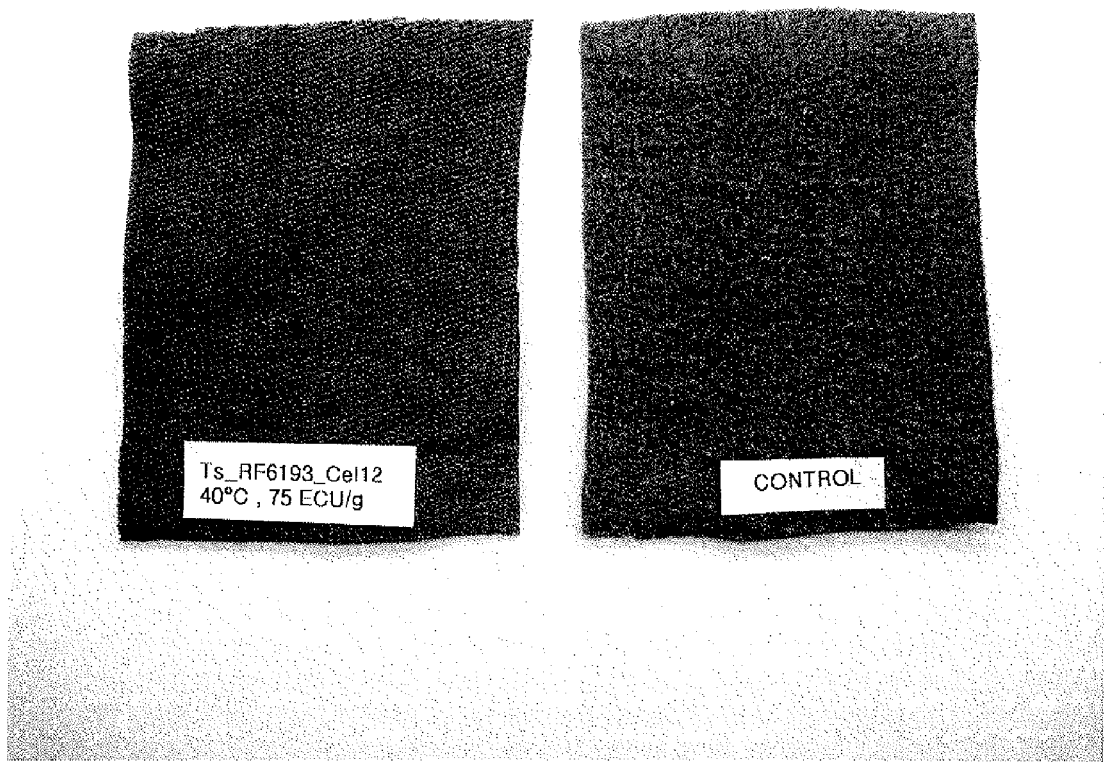
FIG. 7 shows the performance of a recombinant Cel12 preparation Ts_RF6193_Cel12) in biofinishing (defuzzing) treatment at 40° C. compared to control sample without enzyme.

The results are shown in Table 18 and FIG. 6, which show that Fe_6318_cel5 has an excellent biostoning effect and it works best at a pH range of 6-7 (optimum pH 6.5), and at pH 5 the performance is considerably reduced. This is unique compared to other family 5 enzymes that are typically acid cellulases.

TABLE 18

Colour measurements of the face side of denim treated with recombinant protein Fe_6318_cel5A at different pH at 50° C. L* indicates the lightness.

| pH | Before cellulase Treatment L* | After cellulase Treatment L* | Increase of L* |
|---|---|---|---|
| 5 | 16.57 | 19.66 | 3.09 |
| 6 | 16.74 | 21.41 | 4.67 |
| 6.5 | 16.42 | 21.85 | 5.43 |
| 7 | 16.6 | 21.11 | 4.51 |

Example 6

Performance of Fe_6318_Cel5A Protein in Denim Finishing at Different Temperatures Recombinant protein Fe_6318_Cel5A protein produced using *Trichoderma* as host as described in Example 3 was tested for its ability in biostoning of denim at different temperatures to create an abraded look similar to that provided by pumice stones and compared to a commercial neutral Cel45 cellulase ECOSTONE® N400.

The test system for biostoning was as in Example 4, except that two pairs of jeans made of Indigo dyed denim twill obtained from an English supplier (1.3 kg) were used as test material after desizing with ECOSTONE® A200 alpha-amylase and the test pH was 6. Also the effect of the cellulase treatment was evaluated as in Example 4.

The results are set forth in Table 19 and FIG. 6, which show that Fe_6318_Cel5A had as good effect as the commercial neutral cellulase ECOSTONE® N400.

TABLE 19

Colour measurements of the face side of denim treated with recombinant protein Fe_6318_Cel5A at different temperatures (55 min, pH 6.5). L* indicates the lightness.

| Enzyme | Activity/ g garment | Temp. ° C. | Before cellulase treatment/L* | After cellulase treatment/L* | Increase of L* |
|---|---|---|---|---|---|
| ECOSTONE ® N400 | 1500 NCU/g | 50 | 17.53 | 23.31 | 5.79 |
| Fe_6318_Cel5A | 750 NCU/g | 60 | 17.58 | 24.73 | 7.16 |
| Fe_6318_Cel5A | 750 NCU/g | 50 | 17.48 | 23.63 | 6.16 |
| Fe_6318_Cel5A | 750 NCU/g | 40 | 17.60 | 22.23 | 4.64 |
| Fe_6318_Cel5A | 750 NCU/g | 30 | 17.16 | 21.01 | 3.85 |

Example 7

Performance of Recombinant Cel12 and Cel5 Proteins in Biofinishing (Depilling/Defuzzing)

The ability of selected recombinant Cel12 and Cel5 proteins produced using *Trichoderma* as host as described in Example 3, was tested in depilling/defuzzing of cotton knitwear and compared to a commercial preparation ECOSTONE® L900, which is an Cel5 enriched *Trichoderma reesei* cellulase preparation typically used in biofinishing formulations. The cellulase treatments were performed with a Electrolux's Wascator FOM 71 CLS washer extractor under conditions described in Table 20.

Three-yarn fleece made of 100% cotton (Type 9761, Orneule, Finland) were used as test material with filling material. The fabric was first prewashed for 10 min at 50° C. and rinsed 3 times. After that the cotton knit fabric was treated with cellulase at 50° C. for 60 minutes. The enzymes were dosed as acid endoglucanase activity (ECU), except for Fe_6318_Cel5A, which was dosed as neutral cellulase activity units (NCU) per the weight of the fabric, as described in Examples 1 and 4. After draining the enzyme was inactivated (for 10 min at 40/50° C.) by raising the pH above 11 with sodium hydroxide. The fabric was then rinsed three times and dried in a tumbler.

TABLE 20

Test conditions/process parameters used in biofinishing treatments.

| Process parameter | |
|---|---|
| Fabric load | 1.0 kg |
| Water | 15 liter |
| pH control pH 5/6 | with acetic acid (80%) |
| Time | 60 min |
| Temperature | 40/50° C. |
| Cellulase dosage | According to Table 21 |

The fabric samples were evaluated visually according to how much surface fibrils and fuzz was detected. The result of each evaluation was quantified by indicating the result relative to a scale consisting of standards. These standards were pieces of the same fabric washed with different amounts of cellulase and they had a range of intensity of surface fibrils/fuzz from number 1 to 5 with half unit's intervals. Number 0 was a control sample treated without enzyme. The higher the number, the better the depilling/dehairing effect. Number 5 means that the surface fibrils/fuzz were/was removed.

The results are shown in Table 21. Ts_6193_cel12A and Th_6482_cel12A had an excellent and Th_RF6541_cel12A and Fe_6318_cel5A a good depilling/dehairing effect with the same activity dosage as used in denim treatment in the previous Examples. Ts_6193_cel12A had as good performance at 40° C. as at 50° C.

TABLE 21

Results of biofinishing treatments

| Enzyme | Activity/g fabric | T, pH | Evaluation |
|---|---|---|---|
| Control | 0 | 50° C., pH 5 | 0 |
| ECOSTONE ® L900 | 612 ECU/g | 50° C., pH 5 | 4 |
| Th_RF6541_Cel12A | 61 ECU/g | 50° C., pH 5 | 3.5 |
| Th_6482_Cel12A | 375 ECU/g | 50° C., pH 5 | 4.5 |
| Ts_6193_Cel12A | 150 ECU/g | 50° C., pH 5 | 5 |
| Ts_6193_Cel12A | 150 ECU/g | 40° C., pH 5 | 5 |
| Ts_6193_Cel12A | 75 ECU/g | 40° C., pH 5 | 4.5 |
| Fe_6318_Cel5A | 750 NCU/g | 50° C., pH 6 | 3 |
| Fe_6318_Cel5A | 1500 NCU/g | 50° C., pH 6 | 4 |

4-5 indicates an excellent depilling/defuzzing effect, 3 a good depilling/defuzzing effect, and 0 no depilling/defuzzing effect (control treatment without enzyme)

REFERENCES

Altschul S F, W Gish, W Miller, E W Myers and D J Lipman. 1990. Basic local alignment search tool. J. Mol. Biol. 215:403-410.

Bailey M and Nevalainen H. 1981. Induction, isolation and testing of stable *Trichoderma reesei* mutants with improved production of solubilizing cellulase. Enzyme Microb. Technol. 3:153-157.

Bendtsen J D, H Nielsen, G von Heijne and S Brunak. 2004. Improved prediction of signal peptides: SignalP 3.0. J. Mol. Biol. 340:783-795.

Gasteiger E, A Gattiker, C Hoogland, I Ivanyi, R D Appel and A Bairoch. 2003. ExPASy: the proteiomics server for in-depth protein knowledge and analysis. Nucleic Acids Res. 31:3784-3788.

Haakana H, Miettinen-Oinonen A, Joutsjoki V, Mäntylä A, Suominen P and Vehmaanperä J. 2004. Cloning of cellulase genes from *Melanocarpus albomyces* and their efficient expression in *Trichoderma reesei*. Enzyme Microb. Technol. 34:159-167.

Henrissat B. (1991) A classification of glycosyl hydrolases based on amino acid sequence similarities. Biochem. J. 280: 309-316.

Henrissat B. and Bairoch A. (1993) New families in the classification of glycosyl hydrolases based on amino acid sequence similarities. Biochem. J. 293: 781-788.

Henrissat B. and Bairoch A. (1996). Updating the sequence-based classification of glycosyl hydrolases. Biochem. J. 316: 695-696.

Joutsjoki, V V, T K Torkkeli and K M H Nevalainen. 1993. Transformation of Trichoderma reesei with the Hormoconis resinae glucoamylase P (gamP) gene: production of a heterologous glucoamylase by Trichoderma reesei. Curr. Genet. 24:223-228.

Karhunen T, A Mäntylä, K M H Nevalainen and P L Suominen. 1993. High frequency one-step gene replacement in Trichoderma reesei. I. Endoglucanase I overproduction. Mol. Gen. Genet. 241:515-522.

Malardier L, Daboussi M J, Julien J, Roussel F, Scazzocchio C and Brygoo Y. 1989. Cloning of the nitrate reductase gene (niaD) of Aspergillus nidulans and its use for transformation of Fusarium oxysporum. Gene 15:147-156.

Needleman S. and Wunsch C. (1970) A general method applicable to the search for similarities in the amino acid sequence of two proteins. Journal of Molecular Biology 48, 443-453.

Nielsen H, J Engelbrecht, S Brunak and G von Heijne. 1997. Identification of prokaryotic and eykaryotic signal peptides and prediction of their cleavage sites. Protein Engineering 10:1-6.

Nierstrasz V. A. and Warmoeskerken M. M. C. G. (2003) Process engineering and industrial enzyme applications. In: Textile processing with enzymes. A. Cavaco-Paulo and G. M. Gübitz (eds.) Woodhead Publishing Ltd, Cambridge. pp. 120-157.

Paloheimo M, A Mäntylä, J Kallio, and P Suominen 2003. High-yield production of a bacterial xylanase in the filamentous fungus Trichoderma reesei requires a carrier polypeptide with an intact domain structure. Appl. Env. Microbiol. 69:7073-7082.

Penttilä M, H Nevalainen, M Rättö, E Salminen and J Knowles. 1987. A versatile transformation system for the cellulolytic filamentous fungus Trichoderma reesei. Gene 61:155-164.

Raeder U and P Broda. 1985. Rapid preparation of DNA from filamentous fungi. Lett. Appl. Microbiol. 1:17-20.

Rice P, Longden I and Bleasby A. (2000). EMBOSS: The European Molecular Biology Open Software Suite. Trends in Genetics 16:276-277.

Sambrook J, E F Fritsch and T Maniatis. 1989. Molecular cloning, a laboratory manual. Cold Spring Harbor Laboratory, New York, U S.

Sambrook J and D W Russell. 2001. Molecular cloning, a laboratory manual. Cold Spring Harbor Laboratory, New York, U S.

Ward M, Wu S, Dauberman G W, Larenas E, Bower B, Rey M, Clarkson K and Bott R. 1992 Proceedings of the 2$^{nd}$ TRICEL symposium on Trichoderma reesei cellulases and other hybdrolases, Espoo, Finland, 1993 ed. Suominen P and Reinikainen T. Foundation for Biotechonological and industrual fermentation Research 8 (1993): 153-158.

van Zyl W H, Lynd L R, den Haan R, McBride J E. 2007 Consolidated bioprocessing for bioethanol production using Saccharomyces cerevisiae. Adv Biochem Eng Biotechnol.; 108:205-35.

| Sequences | |
|---|---|
| SEQ ID NO: | Sequence |
| 1 | Oligonucleotide primer used for amplifying T. reesei egl2/cel5A gene fragment |
| 2 | Oligonucleotide primer used for amplifying T. reesei egl2/cel5A gene fragment |
| 3 | Oligonucleotide primer used for amplifying T. reesei egl3/cel12A gene fragment |
| 4 | Oligonucleotide primer used for amplifying T. reesei egl3/cel12A gene fragment |
| 5 | Peptide 1 from P. griseofulvum Dierckx RF6288 CCE2 protein |
| 6 | Peptide 2 from P. griseofulvum Dierckx RF6288 CCE2 protein |
| 7 | Peptide 3 from P. griseofulvum Dierckx RF6288 CCE2 protein |
| 8 | Peptide 4 from P. griseofulvum Dierckx RF6288 CCE2 protein |
| 9 | Peptide 5 from P.m griseofulvum Dierckx RF6288 CCE2 protein |
| 10 | Oligonucleotide primer Cel5_cons_A_1 |
| 11 | Oligonucleotide primer Cel5_cons_A_2 |
| 12 | Oligonucleotide primer Cel5_cons_A_3 |
| 13 | Oligonucleotide primer Cel5_cons_B_1 |
| 14 | Oligonucleotide primer Cel5_cons_B_2 |
| 15 | Oligonucleotide primer Cel12_cons_A_1 |
| 16 | Oligonucleotide primer Cel12_cons_A_2 |
| 17 | Oligonucleotide primer Cel12_cons_B_1 |
| 18 | Oligonucleotide primer Cel12_cons_B_2 |
| 19 | Oligonucleotide primer Cel5_S1 |
| 20 | Oligonucleotide primer Cel5_S2 |
| 21 | Oligonucleotide primer Cel5_AS1 |
| 22 | Oligonucleotide primer Cel5_AS2 |
| 23 | Oligonucleotide primer CCE2_1F |
| 24 | Oligonucleotide primer CCE2_2F |
| 25 | Oligonucleotide primer CCE2_3R |
| 26 | Oligonucleotide primer CCE2_4F |
| 27 | Oligonucleotide primer CCE2_5R |
| 28 | Oligonucleotide primer CCE2_6R |
| 29 | PCR fragment obtained from Trichoderma sp. RF6193 using the primers Cel5_cons_A_1 and Cel5_cons_B_1 |
| 30 | PCR fragment obtained from Trichoderma sp. RF6193 using the primers Cel5_cons_A_3 and Cel5_cons_B_1 |
| 31 | PCR fragment obtained from Trichoderma sp. RF6193 using the primers Cel12_cons_A_1 and Cel12_cons_B_1 |
| 32 | PCR fragment obtained from Trichoderma fertile RF6601 using the primers Cel5_cons_A_1 and Cel5_cons_B_1 |
| 33 | PCR fragment obtained from Trichoderma fertile RF6601 using the primers Cel5_cons_A_3 and Cel5_cons_B_1 |
| 34 | PCR fragment obtained from Trichoderma fertile RF6601 using the primers Cel12_cons_A_1 and Cel12_cons_B_1 |
| 35 | PCR fragment obtained from Penicillium spinulosum RF6286 using the primers Cel5_S2 and Cel5_AS2 |
| 36 | PCR fragment obtained from Penicillium spinulosum RF6286 using the primers Cel5_S2 and Cel5_AS2 |
| 37 | PCR fragment obtained from Fusarium cf. equiseti RF6318 using the primers Cel5_S2 and Cel5_AS2 |
| 38 | PCR fragment obtained from Geomyces pannorum RF6547 using the primers Cel5_S2 and Cel5_AS2 |
| 39 | PCR fragment obtained from Penicillium griseofulvum Dierckx RF6288 using the primers CCE2_1F and CCE2_5R |
| 40 | PCR fragment obtained from Geomyces pannorum RF6289 using the primers CCE2_1F and CCE2_3R |
| 41 | Nucleotide sequence of the Trichoderma gamsii RF6208 cel5A gene |
| 42 | Deduced amino acid sequence of the Trichoderma gamsii RF6208 Cel5A |
| 43 | Nucleotide sequence of the Trichoderma gamsii RF6208 cel5B gene |
| 44 | Deduced amino acid sequence of the Trichoderma gamsii RF6208 Cel5B |
| 45 | Nucleotide sequence of the Hypocrea rufa/Trichoderma viride RF6310 cel5A gene |
| 46 | Deduced amino acid sequence of the Hypocrea rufa/ Trichoderma viride RF6310 Cel5A |
| 47 | Nucleotide sequence of the Hypocrea atroviridis RF6323 cel5A gene |
| 48 | Deduced amino acid sequence of the Hypocrea atroviridis RF6323 Cel5A |

Sequences

| SEQ ID NO: | Sequence |
|---|---|
| 49 | Nucleotide sequence of the *Trichoderma harzianum* RF6482 cel5A gene |
| 50 | Deduced amino acid sequence of the *Trichoderma harzianum* RF6482 Cel5A |
| 51 | Nucleotide sequence of the *Hypocrea koningiopsis* RF6604 cel5A gene |
| 52 | Deduced amino acid sequence of the *Hypocrea koningiopsis* RF6604 Cel5A |
| 53 | Nucleotide sequence of the *Trichoderma sp.* RF6193 cel5A gene |
| 54 | Deduced amino acid sequence of the *Trichoderma sp.* RF6193 Cel5A |
| 55 | Nucleotide sequence of the *Trichoderma sp.* RF6193 cel5B gene |
| 56 | Deduced amino acid sequence of the *Trichoderma sp.* RF6193 Cel5B |
| 57 | Nucleotide sequence of the *Trichoderma fertile* RF6601 cel5A gene |
| 58 | Deduced amino acid sequence of the *Trichoderma fertile* RF6601 Cel5A |
| 59 | Nucleotide sequence of the *Trichoderma fertile* RF6601 cel5B gene |
| 60 | Deduced amino acid sequence of the *Trichoderma fertile* RF6601 Cel5B |
| 61 | Nucleotide sequence of the *Trichoderma gamsii* RF6208 cel12A gene |
| 62 | Deduced amino acid sequence of the *Trichoderma gamsii* RF6208 Cel12A |
| 63 | Nucleotide sequence of the *Trichoderma harzianum* RF6482 cel12A gene |
| 64 | Deduced amino acid sequence of the *Trichoderma harzianum* RF6482 Cel12A |
| 65 | Nucleotide sequence of the *Trichoderma harzianum* RF6541 cel12A gene |
| 66 | Deduced amino acid sequence of the *Trichoderma harzianum* RF6541 Cel12A |
| 67 | Nucleotide sequence of the *Trichoderma sp.* RF6193 cel12A gene |
| 68 | Deduced amino acid sequence of the *Trichoderma sp.* RF6193 Cel12A |
| 69 | Nucleotide sequence of the *Trichoderma fertile* RF6601 cel12A gene |
| 70 | Deduced amino acid sequence of the *Trichoderma fertile* RF6601 Cel12A |
| 71 | Nucleotide sequence of the *Penicillium spinulosum* RF6286 cel5A gene |
| 72 | Deduced amino acid sequence of the *Penicillium spinulosum* RF6286 Cel5A |
| 73 | Nucleotide sequence of the *Penicillium spinulosum* RF6286 cel5B gene |
| 74 | Deduced amino acid sequence of the *Penicillium spinulosum* RF6286 Cel5B |
| 75 | Nucleotide sequence of the *Penicillium griseofulvum* Dierckx RF6288 cel5A gene |
| 76 | Deduced amino acid sequence of the *Penicillium griseofulvum* Dierckx RF6288 Cel5A |
| 77 | Nucleotide sequence of the *Fusarium* cf. *equiseti* RF6318 cel5A gene |
| 78 | Deduced amino acid sequence of the *Fusarium* cf. *equiseti* RF6318 Cel5A |
| 79 | Nucleotide sequence of the *Geomyces pannorum* RF6293 cel5A gene |
| 80 | Deduced amino acid sequence of the *Geomyces pannorum* RF6293 Cel5A |
| 81 | Nucleotide sequence of the *Geomyces pannorum* RF6547 cel5A gene |
| 82 | Deduced amino acid sequence of the *Geomyces pannorum* RF6547 Cel5A |

Deposited Microorganisms

| Deposited strain | Culture collection | Deposition date | Accession number |
|---|---|---|---|
| *Trichoderma sp.* RF6193 | 1) | 7 Jun. 2007 | CBS 121354 |
| *Trichoderma gamsii* RF6208 | 1) | 7 Apr. 2006 | CBS 119563 |
| *Hypocrea rufa/Trichoderma viride* RF6310 | 1) | 8 Dec. 2005 | CBS 118970 |
| *Hypocrea atroviridis* RF6323 | 1) | 7 Apr. 2006 | CBS 119561 |
| *Trichoderma harzianum* RF6482 | 1) | 7 Apr. 2006 | CBS 119562 |
| *Trichoderma harzianum* RF6541 | 1) | 16 Jun. 2006 | CBS 119957 |
| *Trichoderma fertile* RF6601 | 1) | 7 Jun. 2007 | CBS 121357 |
| *Hypocrea koningiopsis* RF6604 | 1) | 16 Jun. 2006 | CBS 119960 |
| *Penicillium spinulosum* RF6286 | 1) | 7 Jun. 2007 | CBS 121355 |
| *Penicillium griseofulvum* Dierckx RF6288 | 1) | 7 Apr. 2006 | CBS 119565 |
| *Geomyces pannorum* RF6293 | 1) | 7 Apr. 2006 | CBS 119567 |
| *Geomyces pannorum* RF6547 | 1) | 7 Jun. 2007 | CBS 121356 |
| *Fusarium* cf. *equiseti* RF6318 | 1) | 7 Apr. 2006 | CBS 119568 |
| *E. coli* including pALK2121 | 2) | 7 Jun. 2007 | DSM 19418 |
| *E. coli* including pALK2120 | 2) | 21 Sep. 2006 | DSM 18639 |
| *E. coli* including pALK2118 | 2) | 21 Sep. 2006 | DSM 18638 |
| *E. coli* including pALK2123 | 2) | 5 Dec. 2007 | DSM 19963 |
| *E. coli* including pALK2128 | 2) | 21 Sep. 2006 | DSM 18642 |
| *E. coli* including pALK2158 | 2) | 7 Jun. 2007 | DSM 19419 |
| *E. coli* including pALK2330 | 2) | 15 Nov. 2007 | DSM 19894 |
| *E. coli* including pALK2331 | 2) | 15 Nov. 2007 | DSM 19895 |
| *E. coli* including pALK2359 | 2) | 4 Feb. 2008 | DSM 21129 |
| *E. coli* including pALK2366 | 2) | 15 Nov. 2007 | DSM 19898 |
| *E. coli* including pALK2122 | 2) | 21 Sep. 2006 | DSM 18640 |
| *E. coli* including pALK2129 | 2) | 21 Sep. 2006 | DSM 18643 |
| *E. coli* including pALK2165 | 2) | 7 Jun. 2007 | DSM 19420 |
| *E. coli* including pALK2367 | 2) | 15 Nov. 2007 | DSM 19899 |
| *E. coli* including pALK2333 | 2) | 15 Nov. 2007 | DSM 19896 |
| *E. coli* including pALK2248 | 2) | 5 Dec. 2007 | DSM 19960 |
| *E. coli* including pALK2249 | 2) | 5 Dec. 2007 | DSM 19961 |
| *E. coli* including pALK2031 | 2) | 2 Aug. 2006 | DSM 18505 |
| *E. coli* including pALK2225 | 2) | 16 Mar. 2007 | DSM 19172 |
| *E. coli* including pALK2044 | 2) | 10 Jan. 2007 | DSM 18914 |
| *E. coli* including pALK2250 | 2) | 5 Dec. 2007 | DSM 19962 |

1) Centraalbureau Voor Schimmelcultures at Upsalalaan 8, 3508 AD, Utrecht, the Netherlands
2) Deutsche Sammlung von Mikroorganismen and Zellkulturen GmbH (DSMZ), Inhoffenstrasse 7B, D-38124 Braunschweig, Germany

The invention claimed is:

1. An enzyme preparation comprising a fungal endoglucanase polypeptide, which belongs to glycosyl hydrolase family 12, and which comprises an amino acid sequence having between 90% to 99% sequence identity to SEQ ID NO: 68, and has cellulose activity at a temperature below 50° C. in a spent culture medium from which the host cells are separated, wherein the enzyme preparation further comprises additives.

2. The enzyme preparation of claim 1, wherein the endoglucanase polypeptide is derived from *Trichoderma*.

3. The enzyme preparation of claim 1, wherein the endoglucanase polypeptide has between 95% to 99% sequence identity to SEQ ID NO: 68.

4. The enzyme preparation of claim 1, wherein the endoglucanase polypeptide has between 98% to 99% sequence identity to SEQ ID NO: 68.

5. The enzyme preparation of claim 1, wherein the endoglucanase polypeptide is derived from *Trichoderma* sp. RF6193 (CBS 121354).

6. A detergent composition comprising the enzyme preparation of claim 1.

7. Animal feed comprising the enzyme preparation of claim 1.

8. A process for treating cellulosic material, wherein said process comprises contacting the cellulosic material with the enzyme preparation of claim 1.

9. The process of claim 8, wherein the treatment is carried out at a temperature of ≤50° C., preferably ≤40° C.

10. The process of claim 9, which is carried out at a pH of about 4-6, preferably 4.5-5.5, and more preferably at 5.0-5.5.

11. The process of claim 8, which is biostoning or biofinishing.

12. The process of claim 8, which is hydrolysis of lignocellulosic material or a food application.

13. A method for the production of an enzyme preparation of claim 1 comprising the steps of transforming a host cell with an expression vector encoding the endoglucanase polypeptide of claim 1, and culturing said host cell under conditions enabling expression of said polypeptide, and recovering said polypeptide in culture supernatant.

* * * * *